United States Patent
Chung et al.

(10) Patent No.: US 11,319,533 B2
(45) Date of Patent: May 3, 2022

(54) CRISPR NANOCOMPLEX FOR NONVIRAL GENOME EDITING AND METHOD FOR PREPARING THE SAME

(71) Applicant: KOREA ADVANCED INSTITUTE OF SCIENCE AND TECHNOLOGY, Daejeon (KR)

(72) Inventors: Hyun Jung Chung, Daejeon (KR); Yoo Kyung Kang, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 359 days.

(21) Appl. No.: 16/068,161

(22) PCT Filed: Nov. 27, 2017

(86) PCT No.: PCT/KR2017/013623
§ 371 (c)(1),
(2) Date: Jul. 5, 2018

(87) PCT Pub. No.: WO2018/230785
PCT Pub. Date: Dec. 20, 2018

(65) Prior Publication Data
US 2020/0140844 A1    May 7, 2020

(30) Foreign Application Priority Data
Jun. 14, 2017   (KR) .................. 10-2017-0075053

(51) Int. Cl.
  *C12N 11/02*    (2006.01)
  *C12N 9/22*     (2006.01)
  *C12N 15/11*    (2006.01)

(52) U.S. Cl.
  CPC ............. *C12N 11/02* (2013.01); *C12N 9/22* (2013.01); *C12N 15/11* (2013.01); *C12N 2310/20* (2017.05); *C12N 2800/80* (2013.01)

(58) Field of Classification Search
None
See application file for complete search history.

(56) References Cited

U.S. PATENT DOCUMENTS

2015/0071903 A1*  3/2015  Liu ................... C12N 9/1241
                                                    424/94.3
2017/0100486 A1    4/2017  Ziv

FOREIGN PATENT DOCUMENTS

KR   10-2016-0089526 A    7/2016
KR      10-1796036 B1    11/2017

OTHER PUBLICATIONS

Alexis, F., et al. 2006 Cold Spring Harbor Protoc: pdb.prot4451 (4 pages). (Year: 2006).*
Sigma-Aldrich "polyethylenimine" product sheets: 25 pages, (obtained from the internet Jul. 20, 22, 2021). (Year: 2021).*
Polysciences "polyethylenimine" product sheets: 7 pages, (obtained from the internet Jul. 20, 2021). (Year: 2021).*
Haft, D.H., et al. 2005 PLoS Comput Biol 1(6): e60 (pp. 0474-0483). (Year: 2005).*
Marakova, K.S., et al. 2011 Nat Rev Microbiol 9(6): 467-477. (NIH Public Access copy, 23 pages total). (Year: 2011).*
Office Action from corresponding Canadian Patent Application No. 3,009,389, dated May 7, 2019.
International Search Report from corresponding PCT Application No. PCT/KR2017/013623, dated Mar. 21, 2018.
Li, L., et al.; Challenges in CRISPR/CAS9 Delivery: Potential Roles of Nonviral Vectors:, Human Gene Therapy, 2015, vol. 26, No. 7, pp. 452-462.
Ljubimova, J. Y., et al.; "Covalent Nano Delivery Systems for Selective Imaging and Treatment of Brain Tumors", Advanced Drug Delivery Review, Apr. 2017, vol. 113, pp. 177-200.
Wang, L., et al.; "In Vivo Delivery Systems for Therapeutic Genome Editing", International Journal of Molecular Sciences, 2016, 17, 626.
Xiaong, M.P. et al., "PEGylation of yeast cytosine deaminase for pretargeting", Journal of Pharmaceutical Sciences, vol. 94, No. 6, pp. 1249-1258, 2005; Abstract only; from PubMed; PMID: 15858841.
Ramakrishna, S. et al., "Gene disruption by cell-penetrating peptide-mediated delivery of Cas9 protein and guide RNA.", Genome Res., 24, pp. 1020-1027, 2014.
Office Action from corresponding Australian Patent Application No. 2017390080, dated Jul. 3, 2020.
Yan, M., et al.; "Modulation of Gene Expression by Polymer Nanocapsule Delivery of DNA Cassettes Encoding Small RNAs", PLOS ONE, Jun. 2, 2015, pp. 1-15.
Sun, W., et al.; "Self-Assembled DNA Nanoclews for the Efficient Delivery of CRISPR-Cas9 for Genome Editing", Angew. Chem. 2015, 127, 12197-12201.
Mout, R., et al.; "Direct Cytosolic Delivery of CRISPR/Cas9-Ribonucleoprotein for Efficient Gene Editing", ACS Nano, 11, 2017, pp. 2452-2458.
Futami, J., et al.; "Intracellular Delivery of Proteins into Mammalian Living Cells by Polyethylenimine-Cationization", Journal of Bioscience and Bioengineering, vol. 99, No. 2, 2005, pp. 95-103.

(Continued)

*Primary Examiner* — Marsha Tsay
(74) *Attorney, Agent, or Firm* — Harness, Dickey & Pierce, P.L.C.

(57) ABSTRACT

The present invention relates to a CRISPR nanocomplex for nonviral genome editing, a method for preparing the same, and the like. The CRISPR nanocomplex for nonviral genome editing of the present invention has a size of several nanometers to several microns, enables intracellular delivery without external physical stimulation, and can be utilized for genome editing through nonviral routes with respect to target genes of cells. As a result, when used for preparation of animal model, microbiological engineering, cell engineering for disease treatment, or formulations for biological administration, the CRISPR Nanocomplex shows high intracellular delivery and gene editing efficiency, and can minimize problems, such as nonspecific editing, gene mutation, and induction of cytotoxicity and biotoxicity.

16 Claims, 43 Drawing Sheets
Specification includes a Sequence Listing.

(56) References Cited

OTHER PUBLICATIONS

Office Action from corresponding Korean Patent Application No. 10-2017-0075053, dated Jun. 26, 2020.
Li, et al. (2015) "Challenges in CRISPR/CAS9 Delivery: Potential Roles of Nonviral Vectors.", *Human Gene Therapy*, 26(7):452-462.
Korean Notice of Allowance dated Jan. 14, 2021, issued in Korean Patent Application No. KR Application No. 10-2017-0075053.
Kang, Y. K., et al., "Nonviral Genome Editing Based on a CRISPR Nanocomplex System for Target-Specific Treatment of Multidrug-Resistant Bacterial Infections", Poster from 2016 MRS Fall Meeting & Exhibit, Nov. 27-Dec. 2, 2016, Boston, Massachusetts, "Symposium BM1: Spatiotemporally and Morphologically-Controlled Biomaterials for Medical Applications".
Kang, Y. K., et al.; "Nonviral Genome Editing Based on a Polymer-Derivatized CRISPR Nanocomplex for Targeting Bacterial Pathogens and Antibiotic Resistance", American Chemical Society, Bioconjugate Chemistry, 2017; vol. 28, pp. 957-967.
Kang, Y. K., et al.; "Nonviral genome editing based on a polymer-derivatized CRISPR nanocomplex for targeting bacterial pathogens and antibiotic resistance", Poster from KSBM —2017 Spring Meeting of The Korean Society for Biomaterials, Mar. 31, 2017.
Kang, Y. K., et al.; "Nonviral genome editing based on a CRISPR nanocomplex for target-specific treatment of multidrug-resistant bacterial infections", BIOT: Division of Biochemical Technology, Poster from 253rd American Chemical Society National Meetings & Expositions, Apr. 2-6, 2017, San Francisco, California.

\* cited by examiner

His_flag_NLS_Cas9_GFPuv sequence

```
  1 ATGGGCAGCA GCCATCACCA TCATCACCAC GATTACAAAG ACGATGACGA
 51 TAAGATGGCC CCAAAGAAGA AGCGGAAGGT CGGTATCCAC GGAGTCCCAG
101 CAGCCGACAA GAAGTACAGC ATCGGCCTGG ACATCGGCAC CAACTCTGTG
151 GGCTGGGCCG TGATCACCGA CGAGTACAAG GTGCCCAGCA AGAAATTCAA
201 GGTGCTGGGC AACACCGACC GGCACAGCAT CAAGAAGAAC CTGATCGGAG
251 CCCTGCTGTT CGACAGCGGC GAAACAGCCG AGGCCACCCG GCTGAAGAGA
301 ACCGCCAGAA GAAGATACAC CAGACGGAAG AACCGGATCT GCTATCTGCA
351 AGAGATCTTC AGCAACGAGA TGGCCAAGGT GGACGACAGC TTCTTCCACA
401 GACTGGAAGA GTCCTTCCTG GTGGAAGAGG ATAAGAAGCA CGAGCGGCAC
451 CCCATCTTCG GCAACATCGT GGACGAGGTG GCCTACCACG AGAAGTACCC
501 CACCATCTAC CACCTGAGAA AGAAACTGGT GGACAGCACC GACAAGGCCG
551 ACCTGCGGCT GATCTATCTG GCCCTGGCCC ACATGATCAA GTTCCGGGGC
601 CACTTCCTGA TCGAGGGCGA CCTGAACCCC GACAACAGCG ACGTGGACAA
651 GCTGTTCATC CAGCTGGTGC AGACCTACAA CCAGCTGTTC GAGGAAAACC
701 CCATCAACGC CAGCGGCGTG GACGCCAAGG CCATCCTGTC TGCCAGACTG
751 AGCAAGAGCA GACGGCTGGA AAATCTGATC GCCCAGCTGC CCGGCGAGAA
801 GAAGAATGGC CTGTTCGGAA ACCTGATTGC CCTGAGCCTG GGCCTGACCC
851 CCAACTTCAA GAGCAACTTC GACCTGGCCG AGGATGCCAA ACTGCAGCTG
901 AGCAAGGACA CCTACGACGA CGACCTGGAC AACCTGCTGG CCCAGATCGG
951 CGACCAGTAC GCCGACCTGT TCCTGGCCGC CAAGAACCTG TCCGACGCCA
```

FIG. 1a

His_flag_NLS_Cas9_GFPuv sequence (continued)

```
1001 TCCTGCTGAG CGACATCCTG AGAGTGAACA CCGAGATCAC CAAGGCCCCC
CTGAGCGCCT CTATGATCAA GAGATACGAC GAGCACCACC AGGACCTGAC
1101 CCTGCTGAAA GCTCTCCGTG GGCAGCAGCT GCCTGAGAAG TACAAAGAGA
TTTTCTTCGA CCAGAGCAAG AACGGCTACG CCGGCTACAT TGACGGCGGA
1201 GCCAGCCAGG AAGAGTTCTA CAAGTTCATC AAGCCCATCC TGGAAAAGAT
GGACGGCACC GAGGAACTGC TCGTGAAGCT GAACAGAGAG GACCTGCTGC
1301 GGAAGCAGCG GACCTTCGAC AACGGCAGCA TCCCCCACCA GATCCACCTG
GGAGAGCTGC ACGCCATTCT GCGGCGGGCA GAAGATTTT ACCCATTCCT
1401 GAAGGACAAC CGGGAAAAGA TCGAGAAGAT CCTGACCTTC CGCATCCCCT
ACTACGTGGG CCCTCTGGCC AGGGGAAACA GCAGATTCGC CTGGATGACC
1501 AGAAAGAGCG AGGAAACCAT CACCCCCTGG AACTTCGAGG AAGTGGTGGA
CAAGGGCGCT TCCGCCCAGA GCTTCATCGA GCGGATGACC AACTTCGATA
1601 AGAACCTGCC CAACGAGAAG GTGCTGCCCA AGCACAGCCT GCTGTACGAG
TACTTCACCG TGTATAACGA GCTGACCAAA GTGAAATACG TGACCGAGGG
1701 AATGAGAAAG CCCGCCTTCC TGAGCGGCGA GCAGAAAAAG GCCATCGTGG
ACCTGCTGTT CAAGACCAAC CGGAAAGTGA CCGTGAAGCA GCTGAAAGAG
1801 GACTACTTCA AGAAAATCGA GTGCTTCGAC TCCGTGGAAA TCTCCGGCGT
GGAAGATCGG TTCAACGCCT CCCTGGGCAC ATACCACGAT CTGCTGAAAA
1901 TTATCAAGGA CAAGGACTTC CTGGACAATG AGGAAAACGA GGACATTCTG
GAAGATATCG TGCTGACCCT GACACTGTTT GAGGACAGAG AGATGATCGA
```

FIG. 1b

His_flag_NLS_Cas9_GFPuv sequence (continued)

```
2001 GGAACGGCTG AAAACCTATG CCCACCTGTT CGACGACAAA GTGATGAAGC
AGCTGAAGCG GCGGAGATAC ACCGGCTGG GCAGGCTGAG CCGGAAGCTG
2101 ATCAACGGCA TCCGGGACAA GCAGTCCGGC AAGACAATCC TGGATTTCCT
GAAGTCCGAC GGCTTCGCCA ACAGAAACTT CATGCAGCTG ATCCACGACG
2201 ACAGCCTGAC CTTTAAAGAG GACATCCAGA AAGCCCAGGT GTCCGGCCAG
GGCGATAGCC TGCACGAGCA CATTGCCAAT CTGGCCGGCA GCCCCGCCAT
2301 TAAGAAGGGC ATCCTGCAGA CAGTGAAGGT GGTGGACGAG CTCGTGAAAG
TGATGGGCCG GCACAAGCCC GAGAACATCG TGATCGAAAT GGCCAGAGAG
2401 AACCAGACCA CCCAGAAGGG ACAGAAGAAC AGCCGCGAGA GAATGAAGCG
GATCGAAGAG GGCATCAAAG AGCTGGGCAG CCAGATCCTG AAAGAACACC
2501 CCGTGGAAAA CACCCAGCTG CAGAACGAGA AGCTGTACCT GTACTACCTG
CAGAATGGGC GGGATATGTA CGTGGACCAG GAACTGGACA TCAACCGGCT
2601 GTCCGACTAC GATGTGGACC ATATCGTGCC TCAGAGCTTT CTGAAGGACG
ACTCCATCGA CAACAAGGTG CTGACCAGAA GCGACAAGAA CCGGGGCAAG
2701 AGCGACAACG TGCCCTCCGA AGAGGTCGTG AAGAAGATGA AGAACTACTG
GCGGCAGCTG CTGAACGCCA AGCTGATTAC CCAGAGAAAG TTCGACAATC
2801 TGACCAAGGC CGAGAGAGGC GGCCTGAGCG AACTGGATAA GGCCGGCTTC
ATCAAGAGAC AGCTGGTGGA AACCCGGCAG ATCACAAAGC ACGTGGCACA
2901 GATCCTGGAC TCCCGGATGA ACACTAAGTA CGACGAGAAT GACAAGCTGA
TCCGGGAAGT GAAAGTGATC ACCCTGAAGT CCAAGCTTGT GTCCGATTTC
```

FIG. 1c

His_flag_NLS_Cas9_GFPuv sequence (continued)

```
3001 CGGAAGGATT TCCAGTTTTA CAAAGTGCGC GAGATCAACA ACTACCACCA
CGCCCACGAC GCCTACCTGA ACGCCGTCGT GGGAACCGCC CTGATCAAAA
3101 AGTACCCTAA GCTGGAAAGC GAGTTCGTGT ACGGCGACTA CAAGGTGTAC
GACGTGCGGA AGATGATCGC CAAGAGCGAG CAGGAAATCG GCAAGGCTAC
3201 CGCCAAGTAC TTCTTCTACA GCAACATCAT GAACTTTTTC AAGACCGAGA
TTACCCTGGC CAACGGCGAG ATCCGGAAGC GGCCTCTGAT CGAGACAAAC
3301 GGCGAAACCG GGGAGATCGT GTGGGATAAG GGCGGGGATT TTGCCACCGT
GCGGAAAGTG CTGAGCATGC CCCAAGTGAA TATCGTGAAA AAGACCGAGG
3401 TGCAGACAGG CGGCTTCAGC AAAGAGTCTA TCCTGCCCAA GAGGAACAGC
GATAAGTGA TCGCCAGAA GAAGGACTGG GACCCTAAGA AGTACGGCGG
3501 CTTCGACAGC CCCACCGTGG CCTATTCTGT GCTGGTGGTG GCCAAGTGG
AAAGGGCAA GTCCAAGAAA CTGAAGAGTG TGAAAGAGCT GCTGGGATC
3601 ACCATCATGG AAAGAAGCAG CTTCGAGAAG AATCCCATCG ACTTTCTGGA
AGCCAAGGGC TACAAGGAAG TGAAAAAGGA CCTGATCATC AAGCTGCCTA
3701 AGTACTCCCT GTTCGAGCTG GAAAACGGCC GGAAGAGAAT GCTGGCCTCT
GCCGGCGAAC TGCAGAAGGG AAACGAACTG GCCCTGCCCT CCAAATATGT
3801 GAACTTCCTG TACCTGGCCA GCCACTATGA GAAGCTGAAG GGCTCCCCG
AGGATAATGA GCAGAAACAG CTGTTTGTGG AACAGCACAA GCACTACCTG
3901 GACGAGATCA TCGAGCAGAT CAGCGAGTTC TCCAAGAGAG TGATCCTGGC
CGACGCTAAT CTGGACAAAG TGCTGTCCGC CTACAACAAG CACCGGGATA
```

FIG. 1d

His_flag_NLS_Cas9_GFPuv sequence (continued)

4001 AGCCCATCAG AGAGCAGGCC GAGAATATCA TCCACCTGTT TACCCTGACC
AATCTGGGAG CCCCTGCCGC CTTCAAGTAC TTTGACACCA CCATCGACCG
4101 GAAGAGGTAC ACCAGCACCA AAGAGGTGCT GGACGCCACC CTGATCCACC
AGAGCATCAC CGGCCTGTAC GAGACACGGA TCGACCTGTC TCAGCTGGGA
4201 GGCGACAAAA GCCGGGCGC CACGAAAAAG GCCGGCCAGG CAAAAAGAA
AAAGcttatg agtaaaggag aagaactttt cactggagtt gtcccaattc
4301 ttgttgaatt agatggtgat gttaatgggc acaaattttc tgtcagtgga gagggtgaag gtgatgcaac
atacggaaaa cttacccctta aatttattg
4401 cactactgga aaactacctg ttccatggcc aacactgtc actactttct cttatggtgt tcaatgtcttt tcccgttatc
cggatcatat gaaacggcat
4501 gactttttca agagtgccat gcccgaaggt tatgtacagg aacgcactat atctttcaaa gatgacggga
actacaagac gcgtgctgaa gtcaagtttg
4601 aaggtgatac ccttgttaat cgtatcgagt taaaaggtat tgattttaaa gaagatggaa acattcttgg
acacaaactc gagtacaact ataactcaca
4701 caatgtatac atcacggcag acaaacaaaa gaatggaatc aaagctaact tcaaaattcg ccacaacatt
gaagatggat ccgttcaact agcagaccat
4801 tatcaacaaa atactccaat tggcgatggc cctgtccttt taccagacaa ccattaccctg tcgacacaat ctgccctttc
gaaagatccc aacgaaaagc
4901 gtgaccacat ggtccttctt gagtttgtaa ctgctgctgg gattacacat ggcatggatg agctctacaa ataa

FIG. 1e

Target DNA sequence
t_DNA_mecA

20374 AGTTGTAGTT GTCGGGTTTG GTATATATTT TTATGCTTCA AAAGATAAAG
AAATTAATAA TACTATTGAT GCAGTTATTA ATAAAAATTT CAAACAAGTT
20474 TATAAAGATA GCAGTTATAT TTCTAAAAGC GATAATGGTG AAGTAGAAAT
GACTGAACGT CCGATAAAAA TATATAATAG TTTAGGCGTT AAAGATATAA
20574 ACATTCAGGA TCGTAAAATA AAAAAAGTAT CTAAAAATAA AAAACGAGTA
GATGCTCAAT ATAAAATTAA AACAAACTAC GGTAACATTG ATCGCAACGT
20674 TCAATTTAAT TTTGTTAAAG AAGATGGTAT GTGGAAGTTA GATTGGGATC
ATAGCGTCAT TATTCCAGGA ATGCAGAAAG ACCAAAGCAT ACATATTGAA
20774 AATTTAAAAT CAGAACGTGG TAAAATTTTA GACCGAAACA ATGTGGAATT
GGCCAATACA GGAACAGCAT ATGAGATAGG CATCGTTCCA AAGAATGTAT
20874 CTAAAAAAGA AACAAATTGG TCAAAATTGG GTACAAGATG ATACCTTCGT
TATATCAAAC AACAAATTGA AAATGGATGA ATATTTAAGT GATTTCGGAA
20974 TCCACTTAAA ACCGTTAAAA AATGAAACAG AAAGTCGTAA CTATCCTCTA
AAAAATTTCA TCTTACAACT AATGAAAGAA CTTTACGATA AAAAGCTCCA ACATGAAGAT
21074 GAAAAAGCGA CTTCACATCT ATTAGGTTAT GTTGGTCCCA TTAACTCTGA
AGAATTAAAA CAAAAAGAAT ATAAAGGCTA TAAAGATGAT GCAGTTATTG
21174 GTAAAAAGGG ACTCGAAAAA CTTTACGATA AAAAGCTCCA ACATGAAGAT
GGCTATCGTG TCACAATCGT TGACGATAAT AGCAATACAA TCGCACATAC

FIG. 5a

Target DNA sequence
t_DNA_mecA (continued)

```
21274 ATTAATAGAG AAAAAGAAAA AAGATGGCAA AGATATTCAA CTAACTATTG
ATGCTAAAGT TCAAAAGAGT ATTTATAACA ACATGAAAAA TGATTATGGC
21374 TCAGGTACTG CTATCCACCC TCAAACAGGT GAATTATTAG CACTTGTAAG
CACACCTTCA TATGACGTCT ATCCATTTAT GTATGGCATG AGTAACGAAG
21474 AATATAATAA ATTAACCGAA GATAAAAAAG AACCCTCTGCT CAACAAGTTC
CAGATTACAA CTTCACCAGG TTCAACTCAA AAAATATTAA CAGCAATGAT
21574 TGGGTTAAAT AACAAAAACAT TAGACGATAA AACAAGTTAT AAAATCGATG
GTAAAGGTTG GCAAAAAGAT AAATCTTGGG GTGGTTACAA CGTTACAAGA
21674 TATGAAGTGG TAAATGGTAA TATCGACTTA AAACAAGCAA TAGAATCATC
AGATAACATT TTCTTTGCTA GAGTAGCACT CGAATTAGGC AGTAAGAAAT
21774 TTGAAAAAGG CATGAAAAAA CTAGGTGTTG GTGAAGATAT ACCAAGTGAT
TATCCATTTT ATAATGCTCA AATTCAAAAC AAAAATTTAG ATAATGAAAT
21874 ATTATTAGCT GATTCAGGTT ACGGACAAGG TGAAATACTG ATTAACCCAG
TACAGATCCT TTCAATCTAT AGCGCATTAG AAAATAATGG CAATATTAAC
21974 GCACCTCACT TATTAAAAGA CACGAAAAAC AAGTTTGGA AGAAAAATAT
TATTTCCAAA GAAAATATCA ATCTATTAAC TGATGGTATG CAACAAGTCG
22074 TAAATAAAAAC ACATAAAGAA GATATTTATA GATCTTATGC AAACTTAATT
GGCAAATCCG GTACTGCAGA ACTCAAAATG AAACAAGGAG AAACTGGCAG
22174 ACA
```

FIG. 5b

Primers for target DNA synthesis

Fwd_T_DNA_mecA

5' – AGTTGTAGTTGTCGGGTTTGGTA – 3'

Rev_T_DNA_mecA

5' – TGTCTGCCAGTTTCTCCTTGT – 3'

FIG. 6

Template sequences for sgRNA synthesis

T_sgRNA(1)
5' - GAAATTAATACGACTCACTATAGGGCGTAAAGATATAAACATTCGTTTTAGAGCTAGAAATAGCAAGTTAAAATAAGGCTAGTCCGTTATCAACTTGAAAAAGTGGCACCGAGTCGGTGCTTTTTT – 3'

T_sgRNA(2)
5' – GAAATTAATACGACTCACTATAGGGATGGTATGTGGAAGTTAGATGTTTTAGAGCTAGAAATAGCAAGTTAAAATAAGGCTAGTCCGTTATCAACTTGAAAAAGTGGCACCGAGTCGGTGCTTTTTT – 3'

T_sgRNA(3)
5' – GAAATTAATACGACTCACTATAGGGAACCTGGTGAAGTTGTAATCGTTTTAGAGCTAGAAATAGCAAGTTAAAATAAGGCTAGTCCGTTATCAACTTGAAAAAGTGGCACCGAGTCGGTGCTTTTTT – 3'

FIG. 7

Primer sequences for sgRNA template synthesis

Fwd_T_sgRNA(1)
5' – GAAATTAATACGACTCACTATAGGGCGTTAAAGATATAAACATTCGTTTTAGAGCTAGAAATAGCAAGTTAAAATAAGGCTAGTCCG –3'

Fwd_T_sgRNA(2)
5' – GAAATTAATACGACTCACTATAGGGATGGTATGTGGAAGTTAGATGTTTTAGAGCTAGAAATAGCAAGTTAAAATAAGGCTAGTCCG –3'

Fwd_T_sgRNA(3)
5' – GAAATTAATACGACTCACTATAGGGAACCTGGTGAAGTTGTAATCGTTTTAGAGCTAGAAATAGCAAGTTAAAATAAGGCTAGTCCG –3'

Rev_T_sgRNA
5' – AAAAAAGCACCGACTCGGTGCCACTTTTTCAAGTTGATAACGGACTAGCCTTATTTTAACTTGC –3'

FIG. 8

SEQUENCE LISTING

```
<160> NUMBER OF SEQ ID NOS: 15

<210> SEQ ID NO 1
<211> LENGTH: 4974
<212> TYPE: DNA
<213> ORGANISM: Artificial Sequence
<220> FEATURE:
<223> OTHER INFORMATION: His_flag_NLS_Cas9_GFPuv sequence

<400> SEQUENCE: 1
atgggcagca gccatcacca tcatcaccac gattacaaag acgatgacga taagatggcc      60
ccaaagaaga agcggaaggt cggtatccac ggagtcccag cagccgacaa gaagtacagc     120
atcggcctgg acatcggcac caactctgtg ggctgggcc tgatcaccga cgagtacaag     180
gtgcccagca agaaattcaa ggtgctgggc aacaccgacc ggcacagcat caagaagaac     240
ctgatcggag ccctgctgtt cgacagcggc gaaacagccg aggccacccg gctgaagaga     300
accgccagaa gaagatacac cagacggaag aaccggatct gctatctgca agagatcttc     360
```

```
agcaacgaga tggccaaggt ggacgacagc ttcttccaca gactggaaga gtccttcctg    420
gtggaagagg ataagaagca cgagcggcac cccatcttcg gcaacatcgt ggacgaggtg    480
gcctaccacg agaagtaccc caccatctac cacctgagaa agaaactggt ggacagcacc    540
gacaaggccg acctgcggct gatctatctg gccctggccc acatgatcaa gttccggggc    600
cacttcctga tcgagggcga cctgaacccc gacaacagcg acgtggacaa gctgttcatc    660
cagctggtgc agacctacaa ccagctgttc gaggaaaaac ccatcaacgc cagcggcgtg    720
gacgccaagg ccatcctgtc tgccagactg agcaagagca cacggctgga aaatctgatc    780
gcccagctgc ccggcgagaa gaagaatggc ctgttcggaa acctgattgc cctgagcctg    840
ggcctgaccc ccaacttcaa gagcaacttc gacctggccg aggatgccaa actgcagctg    900
agcaaggaca cctacgacga cgacctggac aacctgctgg cccagatcgg cgaccagtac    960
gccgacctgt ttctggccgc caagaacctg tccgacgcca tcctgctgag cgacatcctg   1020
agagtgaaca ccgagatcac caaggccccc ctgagcgcct ctatgatcaa gagatacgac   1080
gagcaccacc aggacctgac cctgctgaaa gctctcgtgc ggcagcagct gcctgagaag   1140
tacaaagaga ttttcttcga ccagagcaag aacggctacg ccggctacat tgacggcgga   1200
gccagccagg aagagttcta caagttcatc aagcccatcc tggaaaagat ggacggcacc   1260
gaggaactgc tcgtgaagct gaacagagag gacctgctgc ggaagcagcg gaccttcgac   1320
aacggcagca tcccccacca gatccacctg ggagagctgc acgccattct gcggcggcag   1380
gaagattttt acccattcct gaaggacaac cgggaaaaga tcgagaagat cctgaccttc   1440
cgcatcccct actacgtggg ccctctggcc aggggaaaca gcagattcgc ctggatgacc   1500
agaaagagcg aggaaaccat caccccctgg aacttcgagg aagtggtgga caagggcgct   1560
tccgcccaga gcttcatcga gcggatgacc aacttcgata agaacctgcc caacgagaag   1620
gtgctgccca gcacagcct  gctgtacgag tacttcaccg tgtataacga gctgaccaaa   1680
gtgaaatacg tgaccgaggg aatgagaaag cccgccttcc tgagcggcga gcagaaaaag   1740
gccatcgtgg acctgctgtt caagaccaac cggaaagtga ccgtgaagca gctgaaagag   1800
gactacttca gaaaaatcga gtgcttcgac tccgtggaaa tctccggcgt ggaagatcgg   1860
ttcaacgcct ccctgggcac ataccacgat ctgctgaaaa ttatcaagga caaggacttc   1920
ctggacaatg aggaaaacga ggacattctg gaagatatcg tgctgaccct gacactgttt   1980
gaggacagag agatgatcga ggaacggctg aaaacctatg cccacctgtt cgacgacaaa   2040
gtgatgaagc agctgaagcg gcggagatac accggctggg gcaggctgag ccggaagctg   2100
atcaacggca tccgggacaa gcagtccggc aagacaatcc tggatttcct gaagtccgac   2160
ggcttcgcca cagaaaactt catgcagctg atccaccacg acagcctgac ctttaaagag   2220
gacatccaga aagcccaggt gtccggccag ggcgatagcc tgcacgagca cattgccaat   2280
ctggccggca gccccgccat taagaagggc atcctgcaga cagtgaaggt ggtggacgag   2340
ctcgtgaaag tgatgggccg gcacaagccc gagaacatcg tgatcgaaat ggccagagag   2400
aaccagacca cccagaaggg acagaagaac agccgcgaga gaatgaagcg gatcgaagag   2460
ggcatcaaag agctggcag ccagatcctg aaagaacacc ccgtggaaaa cacccagctg   2520
cagaacgaga gctgtacct gtactacctg cagaatgggc gggatatgta cgtggaccag   2580
gaactggaca tcaaccggct gtccgactac gatgtggacc atatcgtgcc tcagagcttt   2640
ctgaaggacg actccatcga caacaaggtg ctgaccagaa gcgacaagaa ccggggcaag   2700
agcgacaacg tgccctccga agaggtcgtg aagaagatga agaactactg gcggcagctg   2760
```

```
ctgaacgcca agctgattac ccagagaaag ttcgacaatc tgaccaaggc cgagagaggc    2820
ggcctgagcg aactggataa ggccggcttc atcaagagac agctggtgga aacccggcag    2880
atcacaaagc acgtggcaca gatcctggac tcccggatga acactaagta cgacgagaat    2940
gacaagctga tccgggaagt gaaagtgatc accctgaagt ccaagctggt gtccgatttc    3000
cggaaggatt tccagtttta caaagtgcgc gagatcaaca actaccacca cgcccacgac    3060
gcctacctga cgccgtcgt gggaaccgcc ctgatcaaaa agtaccctaa gctggaaagc    3120
gagttcgtgt acggcgacta caaggtgtac gacgtgcgga agatgatcgc caagagcgag    3180
caggaaatcg gcaaggctac cgccaagtac ttcttctaca gcaacatcat gaactttttc    3240
aagaccgaga ttaccctggc caacggcgag atccggaagc ggcctctgat cgagacaaac    3300
ggcgaaaccg gggagatcgt gtgggataag ggccgggatt ttgccaccgt gcggaaagtg    3360
ctgagcatgc cccaagtgaa tatcgtgaaa aagaccgagg tgcagacagg cggcttcagc    3420
aaagagtcta tcctgcccaa gaggaacagc gataagctga tcgccagaaa gaaggactgg    3480
gaccctaaga agtacggcgg cttcgacagc cccaccgtgg cctattctgt gctggtggtg    3540
gccaaagtgg aaaagggcaa gtccaagaaa ctgaagagtg tgaaagagct gctgggatc    3600 accatcatgg aaagaagcag cttcgagaag aatcccatcg actttctgga agccaagggc    3660
tacaaagaag tgaaaaagga cctgatcatc aagctgccta agtactccct gttcgagctg    3720
gaaaacggcc ggaagagaat gctggcctct gccggcgaac tgcagaaggg aaacgaactg    3780
gccctgccct ccaaatatgt gaacttcctg tacctggcca gccactatga aagctgaag    3840 ggctcccccg aggataatga gcagaaacag ctgtttgtgg aacagcacaa gcactacctg    3900
gacgagatca tcgagcagat cagcgagttc tccaagagag tgatcctggc cgacgctaat    3960
ctggacaaag tgctgtccgc ctacaacaag caccggata agcccatcag agagcaggcc    4020
gagaatatca tccacctgtt taccctgacc aatctgggag ccctgccgc cttcaagtac    4080 tttgacacca ccatcgaccg gaagaggtac accagcacca aagaggtgct ggacgccacc    4140
ctgatccacc agagcatcac cggcctgtac gagacacgga tcgacctgtc tcagctggga    4200
ggcgacaaaa ggccggcggc cacgaaaaag gccggccagg caaaaaagaa aaagcttatg    4260
agtaaaggag aagaactttt cactggagtt gtcccaattc ttgttgaatt agatggtgat    4320
gttaatgggc acaaattttc tgtcagtgga gagggtgaag gtgatgcaac atacggaaaa    4380 cttacccta aatttatttg cactactgga aaactacctg ttccatggcc aacacttgtc    4440
actactttct cttatggtgt tcaatgcttt tcccgttatc cggatcatat gaaacggcat    4500
gactttttca agagtgccat gcccgaaggt tatgtacagg aacgcactat atctttcaaa    4560
gatgacggga actacaagac gcgtgctgaa gtcaagtttg aaggtgatac ccttgttaat    4620
cgtatcgagt taaaggtat tgattttaaa gaagatggaa acattctcgg acacaaactc    4680
gagtacaact ataactcaca caatgtatac atcacggcag acaaacaaaa gaatggaatc    4740
aaagctaact tcaaaattcg ccacaacatt gaagatggat ccgttcaact agcagaccat    4800
tatcaacaaa atactccaat tggcgatggc cctgtccttt taccagacaa ccattacctg    4860
tcgacacaat ctgcccttc gaaagatccc aacgaaaagc gtgaccacat ggtccttctt    4920
gagtttgtaa ctgctgctgg gattacacat ggcatggatg agctctacaa ataa         4974
```

<210> SEQ ID NO 2
<211> LENGTH: 1803
<212> TYPE: DNA

<213> ORGANISM: Artificial Sequence
<220> FEATURE:
<223> OTHER INFORMATION: Target DNA mecA (20374-22176)

<400> SEQUENCE: 2

```
agttgtagtt gtcgggtttg gtatatattt ttatgcttca aaagataaag aaattaataa      60
tactattgat gcaattgaag ataaaaattt caaacaagtt tataaagata gcagttatat     120
ttctaaaagc gataatggtg aagtagaaat gactgaacgt ccgataaaaa tatataatag     180
tttaggcgtt aaagatataa acattcagga tcgtaaaata aaaaaagtat ctaaaaataa     240
aaaacgagta gatgctcaat ataaaattaa acaaactac ggtaacattg atcgcaacgt      300
tcaatttaat tttgttaaag aagatggtat gtggaagtta gattgggatc atagcgtcat     360
tattccagga atgcagaaag accaaagcat acatattgaa aatttaaaat cagaacgtgg     420
taaaatttta gaccgaaaca atgtggaatt ggccaataca ggaacagcat atgagatagg     480
catcgttcca aagaatgtat ctaaaaaaga ttataaagca atcgctaaag aactaagtat     540
ttctgaagac tatatcaaac aacaaatgga tcaaaattgg gtacaagatg ataccttcgt     600
tccacttaaa accgttaaaa aatggatga atatttaagt gatttcgcaa aaaaatttca     660
tcttacaact aatgaaacag aaagtcgtaa ctatcctcta gaaaaagcga cttcacatct     720
attaggttat gttggtccca ttaactctga agaattaaaa caaaagaat ataaaggcta      780
taaagatgat gcagttattg gtaaaaaggg actcgaaaaa ctttacgata aaaagctcca     840
acatgaagat ggctatcgtg tcacaatcgt tgacgataat agcaatacaa tcgcacatac     900
attaatagag aaaagaaaa aagatggcaa agatattcaa ctaactattg atgctaaagt      960
tcaaaagagt atttataaca acatgaaaaa tgattatggc tcaggtactg ctatccaccc    1020
tcaaacaggt gaattattag cacttgtaag cacaccttca tatgacgtct atccatttat    1080
gtatggcatg agtaacgaag aatataataa attaaccgaa gataaaaaag aacctctgct    1140
caacaagttc cagattacaa cttcaccagg ttcaactcaa aaatattaa cagcaatgat     1200
tgggttaaat aacaaaacat tagacgataa aacaagttat aaaatcgatg gtaaaggttg    1260
gcaaaaagat aaatcttggg gtggttacaa cgttacaaga tatgaagtgg taaatggtaa    1320
tatcgactta aaacaagcaa tagaatcatc agataacatt ttctttgcta gagtagcact    1380
cgaattaggc agtaagaaat ttgaaaaagg catgaaaaaa ctaggtgttg gtgaagatat    1440
accaagtgat tatccatttt ataatgctca aatttcaaac aaaaaatttag ataatgaaat    1500
attattagct gattcaggtt acggacaagg tgaaatactg attaacccag tacagatcct    1560
ttcaatctat agcgcattag aaaataatgg caatattaac gcacctcact tattaaaga     1620
cacgaaaaac aaagtttgga gaaaaatat tatttccaaa gaaatatca atctattaac      1680
tgatggtatg caacaagtcg taaataaaac acataaagaa gatatttata gatcttatgc    1740
aaacttaatt ggcaaatccg gtactgcaga actcaaaatg aaacaaggag aaactggcag    1800
aca                                                                 1803
```

<210> SEQ ID NO 3
<211> LENGTH: 23
<212> TYPE: DNA
<213> ORGANISM: Artificial Sequence
<220> FEATURE:
<223> OTHER INFORMATION: Forward Primer for synthesis of target DNA mecA

<400> SEQUENCE: 3
agttgtagtt gtcgggtttg gta      23

<210> SEQ ID NO 4
<211> LENGTH: 21
<212> TYPE: DNA
<213> ORGANISM: Artificial Sequence
<220> FEATURE:
<223> OTHER INFORMATION: Reverse Primer for synthesis of target DNA mecA

<400> SEQUENCE: 4
tgtctgccag tttctccttg t                                          21

<210> SEQ ID NO 5
<211> LENGTH: 127
<212> TYPE: DNA
<213> ORGANISM: Artificial Sequence
<220> FEATURE:
<223> OTHER INFORMATION: Template sequence for synthesis of sgRNA(1)

<400> SEQUENCE: 5
gaaattaata cgactcacta gggcgttaa agatataaa cattcgtttt agagctagaa    60
atagcaagtt aaaataaggc tagtccgtta tcaacttgaa aaagtggcac cgagtcggtg  120
cttttttt                                                          127

<210> SEQ ID NO 6
<211> LENGTH: 127
<212> TYPE: DNA
<213> ORGANISM: Artificial Sequence
<220> FEATURE:
<223> OTHER INFORMATION: Template sequence for synthesis of sgRNA(2)

<400> SEQUENCE: 6
gaaattaata cgactcacta gggatggt atgtggaagt tagatgtttt agagctagaa    60
atagcaagtt aaaataaggc tagtccgtta tcaacttgaa aaagtggcac cgagtcggtg  120
cttttttt                                                          127

<210> SEQ ID NO 7
<211> LENGTH: 127
<212> TYPE: DNA
<213> ORGANISM: Artificial Sequence
<220> FEATURE:
<223> OTHER INFORMATION: Template sequence for synthesis of sgRNA(3)

<400> SEQUENCE: 7
gaaattaata cgactcacta gggaacct ggtgaagttg taatcgtttt agagctagaa    60
atagcaagtt aaaataaggc tagtccgtta tcaacttgaa aaagtggcac cgagtcggtg  120
cttttttt                                                          127

<210> SEQ ID NO 8
<211> LENGTH: 87
<212> TYPE: DNA
<213> ORGANISM: Artificial Sequence
<220> FEATURE:
<223> OTHER INFORMATION: Forward Primer for synthesis of sgRNA(1)
      template

<400> SEQUENCE: 8
gaaattaata cgactcacta gggcgttaa agatataaa cattcgtttt agagctagaa    60
atagcaagtt aaaataaggc tagtccg                                      87

<210> SEQ ID NO 9
<211> LENGTH: 87

```
<212> TYPE: DNA
<213> ORGANISM: Artificial Sequence
<220> FEATURE:
<223> OTHER INFORMATION: Forward Primer for synthesis of sgRNA(2)
      template

<400> SEQUENCE: 9
gaaattaata cgactcacta tagggatggt atgtggaagt tagatgtttt agagctagaa      60
atagcaagtt aaaataaggc tagtccg                                         87

<210> SEQ ID NO 10
<211> LENGTH: 87
<212> TYPE: DNA
<213> ORGANISM: Artificial Sequence
<220> FEATURE:
<223> OTHER INFORMATION: Forward Primer for synthesis of sgRNA(3)
      template

<400> SEQUENCE: 10
gaaattaata cgactcacta tagggaacct ggtgaagttg taatcgtttt agagctagaa      60
atagcaagtt aaaataaggc tagtccg                                         87

<210> SEQ ID NO 11
<211> LENGTH: 64
<212> TYPE: DNA
<213> ORGANISM: Artificial Sequence
<220> FEATURE:
<223> OTHER INFORMATION: Reverse Primer for synthesis of sgRNA template

<400> SEQUENCE: 11
aaaaaagcac cgactcggtg ccacttttc aagttgataa cggactagcc ttatttaac       60 ttgc                                                                  64

<210> SEQ ID NO 12
<211> LENGTH: 66
<212> TYPE: DNA
<213> ORGANISM: Artificial Sequence
<220> FEATURE:
<223> OTHER INFORMATION: Forward primer for SpCas9

<400> SEQUENCE: 12
gggcatatgg gcagcagcca tcaccatcat caccacgatt acaaagacga tgacgataag      60
atggcc                                                                66

<210> SEQ ID NO 13
<211> LENGTH: 34
<212> TYPE: DNA
<213> ORGANISM: Artificial Sequence
<220> FEATURE:
<223> OTHER INFORMATION: Reverse primer for SpCas9

<400> SEQUENCE: 13
cccaagcttt ttcttttttg cctggccggc cttt                                 34

<210> SEQ ID NO 14
<211> LENGTH: 28
<212> TYPE: DNA
<213> ORGANISM: Artificial Sequence
<220> FEATURE:
<223> OTHER INFORMATION: Forward primer for GFPuv

<400> SEQUENCE: 14
cccaagctta tgagtaaagg agaagaac                                        28
```

```
<210> SEQ ID NO 15
<211> LENGTH: 29
<212> TYPE: DNA
<213> ORGANISM: Artificial Sequence
<220> FEATURE:
<223> OTHER INFORMATION: Reverse primer for GFPuv

<400> SEQUENCE: 15
cccaagcttt tatttgtaga gctcatcca                                29
```

CRISPR NANOCOMPLEX FOR NONVIRAL GENOME EDITING AND METHOD FOR PREPARING THE SAME

CROSS-REFERENCE TO RELATED APPLICATIONS

This application is a national phase application of PCT Application No. PCT/KR2017/013623 filed on Nov. 27, 2017, which claims priority to Korean Patent Application No. 10-2017-0075053 filed on Jun. 14, 2017. The entire disclosures of the applications identified in this paragraph are incorporated herein by reference.

TECHNICAL FIELD

The present invention was made with the support of the Ministry of Health and Welfare, Republic of Korea, under Project No. HI15C1948, which was conducted in the program entitled "Rapid Detection and Diagnosis of Multidrug Resistant Bacteria by Nanoprobe" in the project named "Development of Infectious Disease Crisis Response Technology", by the Korea Advanced Institute of Science and Technology, under management of the Korea Health Industry Development Institute, from 1 Nov. 2015 to 31 Oct. 2018.

The present invention was also made with the support of the Ministry of Health and Welfare, Republic of Korea, under Project No. HI14C2270, which was conducted in the program entitled "Development of molecular diagnosis of cancer by detection of circulating tumor cells" in the project named "World-leading life scientist raising business", by the Korea Advanced Institute of Science and Technology, under management of the Korea Health Industry Development Institute, from 1 Dec. 2014 to 31 Oct. 2017.

The present invention was also made with the support of the Ministry of Health and Welfare, Republic of Korea, under Project No. 2015R1C1A1A02036647, which was conducted in the program entitled "Development of Ultra-Sensitive Diagnosis Method for Multidrug Resistant Pathogen Infection" in the project named "Rising Researcher Support Project", by the Korea Advanced Institute of Science and Technology, under management of the National Research Foundation of Korea, from 1 Jul. 2015 to 30 Jun. 2018.

This application claims priority to and the benefit of Korean Patent Application No. 10-2017-0075053 filed in the Korean Intellectual Property Office on 14 Jun. 2017, the disclosure of which are incorporated herein by reference.

The present invention relates to a CRISPR nanocomplex for nonviral genome editing and a method for preparing the same. And more specifically, the present invention relates to a nanocomplex formed by complexation of sgRNA and a carrier material chemical conjugated with an enzyme protein of a CRISPR genome editing system, a method for preparing the nanocomplex, and a method for using the nanocomplex as a nonviral genome editing system by delivering the nanocomplex into cells.

BACKGROUND

Over the past several decades, the abuse of antibiotics has significantly increased and, as a result, the emergence and spread of multidrug-resistant bacteria have increased. In many cases, these bacteria may acquire severe pathogenicity, infect humans, and spread to other individuals, communities, health institutions, and hospitals. A majority of these pathogens arise from human commensal bacteria, and cause opportunistic infections in individuals with suppressed immunity or certain medical conditions. The sustained treatment with antibiotics naturally selects the mutant bacterial clones with antibiotic resistance, and such antibiotic resistance is acquired by the intrinsic expression or horizontal spread of genes, involved with enzymatic degradation of drugs or inhibition of drug efficacy.

The types of multidrug-resistant bacteria showing highest incidence rates worldwide include methicillin-resistant *Staphylococcus aureus* (MRSA), carbapenem-resistant Enterobacteriaceae (CRE), multidrug-resistant *Acinetobacter baumannii* (MRAB), multidrug-resistant *Pseudomonas aeruginosa* (MRPA), and vancomycin-resistant Enterococci (VRE), and most recently, vancomycin-resistant *Staphylococcus aureus* (VRSA).

The spread of multidrug-resistant bacteria restricts the choice of therapeutic agents in the treatment of bacterial infections, and requires the use and development of more potent drugs. However, the use of drugs with even higher potency would only result in the emergence of more pathogenic or resistant strains, and may cause higher toxicity in patients during treatment.

Another problem is that most of the drugs that are currently used to treat bacterial infections are low-molecular weight antibiotics with broad spectra. Thus, the use of drugs that can specifically target specific pathogens would provide great advantages in minimizing the selective pressure in the growth of bacteria. Unfortunately, the development of drugs or antibody therapeutic agents with narrow spectra has difficulty due to problems of marketability and technical problems, such as the lack of specific biomarkers and acquisition of resistance.

Gene therapeutic agents have been introduced as an innovative approach compared with conventional low-molecular weight drugs or antibody therapeutic agents due to the simplicity and versatility of designing a drug against a target with high specificity. Genetic drugs in the form of plasmid DNA, antisense oligonucleotide, siRNA, or virus-based vectors may be administered to induce or suppress the expression of disease targets. Viral vectors are advantageous for their high transfection efficiencies, but also may show clinical limitations due to problems such as inducing cellular immune responses or antibody or neutralization.

In the case of mammalian cells as targets, the use of siRNA to silence the expression of certain genes has shown promise as a therapeutic agent, and is currently under clinical trials for treating various types of cancer, glaucoma, hemophilia, and familial amyloid diseases. However, the direct administration of such a gene therapeutic agent would cause poor efficacy due to the immediate enzymatic degradation in the body fluid or low delivery efficiency to a target site. Therefore, carrier materials, such as cationic polymers, lipid-based materials, inorganic nanoparticles, cell penetrating peptides, and dendrimers, have been used to condense the biologically active molecules and deliver the same to the target. However, for bacterial cells, the attempts to use nonviral gene delivery strategies have been severely limited due to the poor delivery efficiency of genes through cell walls as well as low efficacy of gene therapeutic agents.

Recently, the great advances in genome editing technologies have opened a new era for the development of gene therapeutic agents as well as genetic manipulation of model organisms. Current genome editing technologies employ zinc finger nuclease (ZFN), transcription activator-like effector nuclease (TALEN), clustered regularly interspaced short palindromic repeat (CRISPR), and the like according to the recognizing or mutating manner a particular gene. Of these, CRISPR systems, which are known as acquired immune systems of microorganisms, are classified into type I, II, and III. In particular, Cas9 protein (SpCas9) derived from *Streptococcus pyogenes*, which corresponds to the type II CRISPR system, serves as an action of causing double-strand cleavage in DNA by the assistance of a single-guide RNA (sgRNA) that targets a specific gene through complementary binding. Especially, target-specific crRNA (CRISPR RNA) of sgRNA shows high targeting efficiency by recognizing the protospacer-adjacent-motif (PAM) nucleotide sequence having the 5'-NGG-3' sequence, is about 20 nucleotides in length, which is very short compared with the initial gene scissors zinc finger nuclease (ZFN) or transcription activator-like effector nuclease (TALEN), and provides great advantages through the design and manufacture simplified compared with other conventional genome editing strategies. Thus, the CRISPR system is widely used for animal model construction by inducing specific cleavage in a target gene, and research on applying the system as a therapeutic agent by using a function of silencing or editing a target gene has been continuously tried. However, until the present, viral editing with high expression efficiency has been most frequently used for CRISPR, and has limitations in clinical application due to the toxicity of vectors, induction of cellular immune responses, and antibody neutralization responses.

The nonviral intracellular delivery of CRISPR endonuclease protein and sgRNA has been reported to be less efficient than using viral vectors, and overcoming this drawback is a key issue. In particular, the protein-based delivery generally has a poor effect due to in vivo immediate enzymatic degradation or low delivery efficiency to the target site.

Therefore, there is the need for nonviral genome editing having the advantages of safety, simple synthesis step, and high delivery efficiency in the treatment using CRISPR. In addition, for the introduction into therapeutic agents, carrier materials, such as cationic polymers, lipid-based materials (lipid-based carrier materials, e.g., lipofectamine), inorganic nanoparticles, cell penetrating peptides, and dendrimers, have been reported as gene/drug delivery materials. However, these materials can condense biologically active molecules due to cationic or liposoluble properties thereof, and therefore, for the delivery of nonviral CRISPR system, many efforts to improve the delivery and operational efficiency of Cas protein and sgRNA with respect to targets have been reported. The physical and noncovalent encapsulation of Cas protein and sgRNA using the lipid-based materials has a restriction in their practical applications due to the low encapsulating efficacy, and thus the resulting administration at high dosages causes toxicity problems.

Therefore, there is an urgent need to develop a novel CRISPR delivery method capable of efficient intracellular delivery without toxicity.

DETAILED DESCRIPTION

Technical Problem

The present inventors endeavored and researched to develop a novel type nonviral genome editing method capable of overcoming low delivery efficiencies and toxic problems in conventional viral genome editing methods or genome editing methods using lipid-based formulations. As a result, the present inventors confirmed that, when a CRISPR nanocomplex is prepared by conjugating a polymer carrier material onto a CRISPR enzyme protein and mixing the conjugate and sgRNA, the CRISPR nanocomplex is excellent in delivery efficiency of the genome editing enzyme and genome editing effects, and can solve problems such as biotoxicty, and thus completed the present invention.

Therefore, an aspect of the present invention is to provide a polymer carrier material-conjugated clustered regularly interspaced short palindromic repeats (CRISPR) enzyme protein.

Another aspect of the present invention is to provide a method for preparing the polymer carrier material-conjugated CRISPR enzyme protein.

Still another aspect of the present invention is to provide a CRISPR nanocomplex comprising a polymer carrier material-conjugated CRISPR enzyme protein and single guide RNA (sgRNA).

Still another aspect of the present invention is to provide a method for preparing a CRISPR nanocomplex, the method comprising a step for mixing a polymer carrier material-conjugated CRISPR enzyme protein and sgRNA.

Still another aspect of the present invention is to provide a genome editing composition comprising a polymer carrier material-conjugated CRISPR enzyme protein or the CRISPR nanocomplex.

Technical Solution

In accordance with an aspect of the present invention, there is provided a polymer carrier material-conjugated clustered regularly interspaced short palindromic repeats (CRISPR) enzyme protein.

CRISPR is the abbreviation for clustered regularly interspaced short palindromic repeats, and refers to the third generation gene scissors derived from bacterial immune systems. Most virus-infected bacteria die, but some survive and store a part of their viral DNA in their genomes. Thereafter, the occurrence of re-infection generates small guide RNA (sgRNA) based on the stored information, which binds with the Cas9 endonuclease to cleave external DNA. Here, the guide RNA binds to a desired target gene through complementary nucleotide pairs to determine specificity thereof, and Cas9 protein acts as a nuclease that cleaves the target gene. Therefore, the guide RNA can cleave any DNA nucleotide sequence according to the guide RNA nucleotide sequence, and thus active research using CRISPR-Cas9 gene scissors is being currently conducted.

According to an embodiment of the present invention, the CRISPR enzyme protein is an enzyme protein that can cleave or edit a target site on the genome by a CRISPR genome editing procedure, and may be any one selected from: a protein selected from the group consisting of Cas1, Cas2, Cas3, Cas4, Cas5, Cas6, Cas9, Cse1, Cse2, Cse3, Cse4, Cas5d, Cas5e, Csy1, Csy2, Csy3, Csy4, Cpf1, Csn1, Csn2, Csd1, Csd2, Cst1, Cst2, Cas5t, Csh1, Csh2, Cas5h, Csa1, Csa2, Csa3, Csa4, Csa5, Cas5a, Csm1, Csm2, Csm3, Csm4, Csm5, Cmr1, Cmr2, Cmr3, Cmr4, Cmr5, Cmr6, dCas9 (dead Cas9), Cas9, C2c2 (Cas13a), cytidine deaminase enzyme (CDA), apolipoprotein B editing complex (APOBEC) 14, uracil glycosylase inhibitor (UGI), and activation-induced deaminase (AID); or a recombinant protein thereof, but is not limited thereto.

As used herein, the term "carrier" "delivery system", or "vehicle" refers to a polymer, a protein, a lipid, or the like, that is used to allow a material which exhibits physiological activity or can act with activity in vivo, such as proteins, hormones, enzymes, and nucleic acids to pass through a biological membrane, such as a cell membrane, and introducing the material into a cell. According to an aspect of the present invention, the carrier is a biocompatible polymer having no cytotoxicity or histotoxicity, and is a synthetic polymer or a natural polymer.

As used herein, the term "cargo" refers to a material that can act with activity in vivo, for example, a physiologically active material and an enzyme, such as a protein, a hormone, or a nucleic acid, which is to be introduced into a cell by binding or conjugation with the carrier. According to an aspect of the present invention, the term "cargo" used herein means a genetic scissors enzyme protein, and more specifically, CRISPR enzyme protein, and single guide RNA (sgRNA), but is not limited thereto.

According to an embodiment of the present invention, the polymer carrier material may be selected from the group consisting of branched polyethyleneimine, linear polyethyleneimine, polypropyleneimine, polyamidoamine, polyethylene glycol, polyethylene oxide-polypropylene oxide copolymer, poly-lactic acid, poly-glycolic acid, poly(D, L-lactic acid-co-glycolic acid), polycaprolactone, polyphosphoester, polyphosphazene, poly(beta-aminoester), branched poly(amino ester), polyaminobutyl-glycolic acid, polyorthoester, poly(hydroxyproline) ester, polyacrylamide, polyvinylpyrrolidone, polyvinyl alcohol, poly(2-(dimethylamino)ethylmethacrylate) (PDMAEMA), dendrimer, hyaluronic acid, alginate, chitosan, dextran, cyclodextrin, spermine, polyarginine, poly-lysine, and copolymers or mixtures thereof, but is not limited thereto.

According to an embodiment of the present invention, the present invention employed a branched polyethyleneimine as the polymer carrier material.

The polymer carrier material is conjugated with the CRISPR enzyme protein to increase the delivery efficiency of the CRISPR enzyme protein in target cells with respect to prokaryotic cells including bacteria and eukaryotic cells.

As existing methods for the intracellular delivery of CRISPR enzyme proteins, there are a method using a viral vector and a method using a nonviral carrier material such as lipofectamine. However, in the case of using a viral vector, a lot of non-specific reactions occur, and in the case of using a lipid-based nonviral carrier material, such as lipofectamine, the delivery efficiency is favorable in eukaryotic cells, but the delivery efficiency is very poor in prokaryotic cells such as bacteria, and thus the use of the nonviral carrier material is difficult.

The carrier material-conjugated CRISPR enzyme protein of the present invention has a DNA cleaving or editing action in an aqueous solution.

According to an embodiment of the present invention, the polymer carrier material and the CRISPR enzyme protein may be conjugated by a crosslinker selected from the group consisting of succinimidyl 4-(N-maleimidomethyl)cyclohexane-1-carboxylate (SMCC), sulfosuccinimidyl 4-(N-maleimidomethyl)cyclohexane-1-carboxylate (sulfo-SMCC), N-α-maleimidoacet-oxysuccinimide ester (AMAS), N-β-maleimidopropyl-oxysuccinimide ester (BMPS), N-γ-maleimidobutyryl-oxysuccinimide ester (GMBS), m-maleimidobenzoyl-N-hydroxysuccinimide ester (MBS), N-ε-malemidocaproyl-oxysuccinimide ester (EMCS), PEGylated SMCC (SM(PEG)), succinimidyl 3-(2-pyridyldithio)propionate (SPDP), PEGylated SPDP (PEG-SPDP), disuccinimidyl glutarate (DSG), dicyclohexylcarbodiimide (DCC), disuccinimidyl suberate (DSS), bissulfosuccinimidyl suberate (BS3), dithiobis(succinimidyl propionate) (DSP), ethylene glycol bis(succinimidyl succinate) (EGS), dimethyl pimelimidate (DMP), bismaleimidoethane (BMOE), 1,4-bismaleimidobutane (BMB), dithiobismaleimidoethane (DTME), 1-ethyl-3-(3-dimethylaminopropyl) carbodiimide hydrochloride (EDC), N-Hydroxysuccinimide (NHS), propargyl-succinimidyl-ester, dibenzocyclooctyne-maleimide (DBCO-maleimide), dibenzocyclooctyne-PEG4-maleimide (DBCO-PEG-maleimide), dibenzocyclooctyne-S—S—N-hydroxysuccinimidyl ester (DBCO—S—S—NHS ester), dibenzocyclooctyne-N-hydroxysuccinimidyl ester (DBCO-NHS ester), acetylene-PEG-NHS ester, and alkyne-PEG-maleimide.

The listed crosslinkers are chemical crosslinkers, and induce a binding reaction between a reactive group of the crosslinker and an active group of the protein to be conjugated, thereby conjugating the polymer carrier material and the CRISPR enzyme protein of the present invention.

Examples of the reactive groups of the chemical crosslinkers and target active groups are as shown in table 1, but are not limited thereto.

TABLE 1

| Crosslinker reactive group | Target active group | Crosslinker reactive group | Target active group |
|---|---|---|---|
| Arylazide | —NH$_2$ (primary amine or non-specific) | Maleimide | sulfhydryl |
| Carboimide | amine/carboxyl | NHS-ester | amine |
| Hydrazide | carbohydrate (oxidation) | PFP-ester | amine |
| Hydroxymethyl phosphine | amine | Solarene | thymine |
| Imidoester | amine | Pyridyl disulfide | sulfhydryl |
| Isocyanate | Hydroxy (insoluble) | Vinyl sulfone | sulfhydryl, amine, hydroxy |
| Carbonyl | hydrazine | | |

In an example of the present invention, sulfo-SMCC was used as a chemical crosslinker, and sulfo-SMCC was added to a branched polyethyleneimine (bPEI) to activate an amine group of the branched polyethyleneimine through substitution with a maleimide group, and then the activated primary amine group of the polyethyleneimine reacts with a free sulfhydryl group on the cysteine residue of the SpCas9 protein, thereby preparing SpCas9 conjugated with bPEI (SpCas9-bPEI). In addition, it was verified that the conjugation of the polymer carrier material and CRISPR enzyme protein (e.g., SpCas9-bPEI) was successfully attained in the following example.

In the present invention, the polyethyleneimine, which is one of the most widely used carrier materials for gene delivery (e.g., siRNA, plasmid DNA), was selected for modification of cargo since the polyethyleneimine can be used in a branched or linear form with various molecular weights. In addition, a branched form amine was selected since the branched form is rich in amine groups including especially a primary amine compared with linear amines, and thus achieves efficient packaging and delivery. The direct covalent binding modification of the protein, instead of the physical encapsulation, was selected to minimize the amount of the carrier material for administration, in order to attempt to solve the problems of biotoxicity and decreased efficacy due to insufficient release. The bPEI was covalently introduced onto the Cas9 endonuclease, to induce packaging by an electrostatic interaction, thereby improving the delivery of the protein itself as well as sgRNA into bacteria.

In accordance with another aspect of the present invention, there is provided a method for preparing a polymer carrier material-conjugated clustered regularly interspaced short palindromic repeats (CRISPR) enzyme protein, the method including:

(a) reacting a functional group of a polymer carrier material with a bifunctional crosslinker to prepare an activated polymer carrier material; and (b) reacting a functional group of a CRISPR enzyme protein with the activated polymer carrier material to prepare a conjugation material.

The preparation method of the present invention will be described by steps in detail.

Step (a): Step of Reacting Functional Group of Polymer Carrier Material with Bifunctional Crosslinker to Prepare Activated Polymer Carrier Material The functional group of the polymer carrier material is activated by reaction with the bifunctional chemical crosslinker. The polymer carrier material cannot be linked with other molecules until the functional group of the polymer carrier material is activated.

The crosslinker indicates a reagent that chemically links two or more different kinds of molecules, and the term bifunctional indicates a property of inducing the linkage between two molecules having the same or different functional groups.

The activation reaction of the polymer carrier material may be conducted in a solvent selected from the group consisting of dimethylsulfoxide (DMSO), dimethylformamide (DMF), ethanol, methanol, water, methylene chloride, and chloroform, but is not limited thereto, and any solvent that can be used in an activation reaction for an intermolecular conjugation reaction in the art may be used without limitation.

The activation reaction of the polymer carrier material may be conducted under a temperature condition of 4-60° C., specifically 4-50° C., 4-40° C., 4-30° C., or 4-25° C., but is not limited thereto.

In addition, the activation reaction of the polymer carrier material may be conducted for 0.5-24 h, specifically 0.5-12 h, 0.5-6 h, 1-24 h, 1-12 h, or 1-6 h, but is not limited thereto.

In the above step, the contents of the kind of the polymer carrier material overlap those described above with respect to the polymer carrier material-conjugated CRISPR enzyme protein, and thus the description thereof will be omitted.

Step (b): Step of Reacting Functional Group of CRISPR Enzyme Protein with Activated Polymer Carrier Material to Prepare Conjugation Material The functional group of the polymer carrier material activated in step (a) reacts with the functional group of the CRISPR enzyme protein to prepare the conjugation material.

Here, the molar ratio of the polymer carrier material and the CRISPR enzyme protein in step (b) may be, for example, $1:10^{-6}$ to $1:10^{6}$, $1:10^{-5}$ to $1:10^{5}$, $1:10^{-4}$ to $1:10^{4}$, $1:10^{-3}$ to $1:10^{3}$, $1:10^{-2}$ to $1:10^{2}$, or $1:10^{-1}$ to $1:10^{1}$, but is not limited thereto.

In addition, the conjugation reaction between the polymer carrier material and the CRISPR enzyme protein may be conducted under a temperature condition of 4-60° C., specifically 4-50° C., 4-40° C., 4-30° C., or 4-25° C., but is not limited thereto.

The conjugation reaction between the polymer carrier material and the CRISPR enzyme protein may be conducted for 0.5-48 h, specifically 0.5-36 h, 0.5-24 h, 0.5-12 h, more specifically 1-48 h, 1-24 h, 1-12 h, or 4-12 h, but is not limited thereto.

Here, the conjugation reaction between the polymer carrier material and the CRISPR enzyme protein may be conducted in an aqueous solvent with pH 4-10, and any aqueous buffer that can maintain the pH range may be used without limitation.

In addition, the contents of the kind of the CRISPR enzyme protein overlap those described above with respect to the polymer carrier material-conjugated CRISPR enzyme protein of the present invention, and thus the description thereof will be omitted.

According to still another aspect of the present invention, the present invention provides a CRISPR nanocomplex comprising a polymer carrier material-conjugated CRISPR enzyme protein and single guide RNA (sgRNA).

In the present invention, the CRISPR nanocomplex is in a dosage form in which a carrier material-conjugated CRISPR enzyme protein is mixed with sgRNA to a target gene, and means a complex formed by a physical interaction of the above-described carrier material-conjugated CRISPR enzyme protein and sgRNA.

More specifically, the CRISPR nanocomplex means a complex composed of a carrier material-conjugated CRISPR enzyme protein and sgRNA, instead of using virus or DNA vector, and thus is characterized by being a nonviral nanocomplex.

According to an embodiment of the present invention, the CRISPR nanocomplex is a complex that can be dispersed in an aqueous solution, and has a particle size of 1-10,000 nm, but is not limited thereto.

According to another embodiment of the present invention, the CRISPR nanocomplex has a zeta potential of −100 to +100 mV.

The sgRNA of the present invention is a ribonucleic acid that directs a CRISPR enzyme protein to a specific site of a target gene on the genome, and is characterized by including CrRNA (CRISPR RNA) and trans-activating RNA (TracrRNA) sequences with respect to a protospacer, which is a target site close to the protospacer-adjacent motif (PAM) sequence.

As the target gene of the sgRNA, any target gene that is desired by the inventors may be selected. Examples of the target gene may include mecA, mecR1, aph, NDM-1, KPC, oxa, ure, lrg, cap, spl, KPC, GES, IMP, VIM, KRAS, Stk11, TP53, PTEN, BRCA1, BRCA2, Akt, Stat, Stat4, JAK3, JAK2, WT1, ERBB2, ERBB3, ERBB4, NF1, NOTCH1, NOTCH3, ATM, ATR, HIF, HIF1 α, HIF3 α, Met, Bcl2, FGFR1, FGFR2, CDKN2α, APC, RB, MEN1, PPAR α, PPAR γ, AR, TSG101, IGF, Igf1, Igf2, Bax, Bcl2, caspase, Kras, Apc, NF1, MTOR, Grm1, Grm5, Grm7, Grm8, mGlurR1, mGlurR5, mGlurR8, PLC, AMPK, MAPK, Raf, ERK, TLR4, BRAF, PI3K, F8, F8C, F9, HEMB, KIR3DL1, NKAT3, NKB1, AMB1I, KIR3DS1, IFNG, CXCLI2, IL2RG, SCIDX1, SCIDX, IMD4, CCR5, SCYA5, D17S136E, TCP228, CXCR2, CXCR3, CXCR4, CCR4, CCR6, CCR7, CX3CR1, CD4, CFTR, HBB, HBA2, HBD, HBA1, LCRB, SCN1A, CHD8, FMR1, VEGF, EGFR, myc, Bcl-2, survivin, SOX2, Nrgl, Erb4, Cplx1, Tph1, Tph2, GSK3, GSK3α, GSK3 β, El, UBB, PICALM, PSI, SORL1, CR1, UbaI, Uba3, CHIP, UCH, Tau, LRP, CH1P28, Uchl1, Uchl3, APP, Cx3crl, ptpn22, TNF-α, NOD2, IL-1a, IL-1b, IL-6, IL-10, IL-12, IL-1a, IL-1b IL-13, IL-17a, IL-17b, IL-17c, IL-17d, IL-17f, CT1LA4, Cx3c11J, DJ-1, PINK1, Prp, DJ-1, PINK1, LRRK2, ALAS2, ASB, ANH1, ABCB7, ABC7, ASAT, CDAN1, CDA1, DBA, PKLR, PK1, RIPS19, NT5C3, UMPH1, PSN1, RHAG, RH50A, NRAMP2, SPTB, TBXA2R, P2X1P, 2RX1, HF1, CFH, HUS, MCFD2, Drd2, Drd4, ABAT, BCL7A, BCL7, TALI, TCL5, TAL2, FLT3, NBS1, NBS, ZNEN1A1, TYR, ALDH, ALDH1A1, ADH, FASN, PI, ATT, F5, MDC1C, LAMA2, LAMM, LARGE, MDC1D, FCMD, TTID, MYOT, CAPN3, CANP3, DYSF, SGCG, DMDA1, SCG3, SGCA, ADL, DAG2, DMDA2, SGCB, LGMD2B, LGMD2C, LGMD2D, LGMD2E, LGMD2F, LGMD2G, LGMD2H, LGMD2I, SGCD, SGD, CMD1L, TCAP, CMD1N, TRIM32, HT2A, FKRP, POMT1, CAV3, LGMD1C, SEPN1, SELN, RSMD1, PLEC1, PLTN, EBS1, PPP2R1A, PPP2CA, PPP1CC, PPP2R5C, GFP, RFP, YFP, tdTomato, mCherry, and luciferase. These are only for illustration, but are not limited thereto.

According to still another aspect of the present invention, the present invention provides a method for preparing the above-described CRISPR nanocomplex.

The method for preparing the CRISPR nanocomplex includes a step for mixing the above-described polymer carrier material-conjugated CRISPR enzyme protein with sgRNA for a target gene.

According to an embodiment of the present invention, the mixing molar ratio of the carrier material-conjugated CRISPR enzyme protein and the sgRNA in the preparation of the CRISPR nanocomplex is $1:10^{-6}$ to $1:10^{6}$, specifically $1:10^{-5}$ to $1:10^{5}$, $1:10^{-4}$ to $1:10^{4}$, and most specifically $1:10^{-3}$ to $1:10^{3}$, but is not limited thereto.

In addition, the mixing temperature may be 4-37° C., specifically 4-25° C., 15-37° C., or 15-25° C., but is not limited thereto.

The mixing reaction may be conducted for 0.1-12 h, specifically 0.1-6 h, 0.1-3 h, 0.1-1 h, most specifically 0.1-0.5 h for preparation of the nanocomplex, but is not limited thereto.

According to still another aspect of the present invention, the present invention provides a genome editing composition comprising the above-described polymer carrier material-conjugated CRISPR enzyme protein, or the above-described CRISPR nanocomplex.

The polymer carrier material-conjugated CRISPR enzyme protein and the above-described CRISPR nanocomplex contained in the genome editing composition correspond to the invention described in another aspect of the present invention above.

When the composition of the present invention is a pharmaceutical composition, the composition of the present invention contains a pharmaceutically acceptable carrier. The pharmaceutically acceptable carrier is abnormally used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methyl hydroxybenzoate, propyl hydroxybenzoate, talc, magnesium stearate, and mineral oil. The composition of the present invention may further contain, in addition to the above ingredients, a lubricant, a wetting agent, a sweetening agent, a flavoring agent, an emulsifier, a suspending agent, a preservative, and the like.

The pharmaceutical composition of the present invention may be administered orally or parentally, and may be administered through, for example, intravenous injection, subcutaneous injection, muscular injection, intraperitoneal injection, topical administration, intranasal administration, intrapulmonary administration, rectal administration, intrathecal administration, ocular administration, skin administration, transdermal administration, or the like.

The appropriate dose of the pharmaceutical composition of the present invention varies depending on factors such as a formulating method, manner of administration, patient's age, body weight, gender, severity of disease, food, time of administration, route of administration, excretion rate, and response sensitivity, and an ordinarily skilled practitioner can easily judge and prescribe the dose effective for the desired treatment or prevention.

According to a specific embodiment of the present invention, the daily dose of the pharmaceutical composition of the present invention is 0.0001-1000 mg/kg, but is not limited thereto. As used herein, the term "pharmaceutically effective amount" refers to an amount sufficient to induce edition of a desired gene.

The composition of the present invention is formulated using a pharmaceutically acceptable carrier and/or excipient according to the method that is easily conducted by a person having ordinary skills in the art to which the present invention pertains, and the composition of the present invention may be prepared into a unit dosage form or may be inserted into a multi-dose container. Here, the dosage form of the composition may be a solution, a suspension, or an emulsion in an oily or aqueous medium and the composition may further include a dispersing agent or a stabilizer.

According to an embodiment of the present invention, the composition, when administered to separated cells, tissues, or individuals, delivers the above-described polymer carrier material-conjugated CRISPR enzyme protein, or CRISPR nanocomplex, into cells to induce genome editing by a genome editing action of the CRISPR enzyme protein.

Here, examples of the cells allowing the intracellular delivery include: eukaryotic cells, such as HeLa, A549, MDAMB, SK-BR-3, OVCAR, PC3, PC12, HEK293, Jurkat, CD4+ T cells, CD8+ T cells, RAW264.7, macrophages, monocytes, neutrophils, natural killer cells (NK cells), dendritic cells (DCs), myeloid-derived suppressor cells (MDSCs), embryonic stem cells, mesenchymal stem cells, induced pluripotent stem cell (iPSCs), vascular endothelial cells, epidermal cells, hepatocytes, muscular cells, bone cells, fibroblasts, cartilage cells, nerve cells, neural stem cells, adipose-derived stem cells (ADSCs), mouse embryonic fibroblasts (MEFs), fungal cells, and parasite cells; or prokaryotic cells, such as *S. aureus, E. coli, P. aeruginosa, K. pneumoniae, A. baumannii, B. subtilis, S. epidermidis, E. faecalis*, and *S. pneumonia*.

As verified in an example of the present invention, the uptake of the polymer carrier material-conjugated CRISPR enzyme protein and the CRISPR nanocomplex of the present invention into bacterial cells showed a genome editing effect, and showed high delivery efficiency even in mammalian cells.

The polymer carrier material-conjugated CRISPR enzyme protein and the CRISPR nanocomplex of the present invention showed excellent intracellular delivery efficiency compared with existing lipid-based carrier materials, such as lipofectamine, and thus also showed an excellent target gene editing effect.

As described above, the present inventors endeavored to develop a novel delivery method for delivering genome editing by CRISPR into cells including bacterial and mammalian cells at a high efficiency, and confirmed that a polymer-derivatized CRISPR Cas9 protein by direct covalent bond modification and a nano-sized complex using the same were formed, and can be used as a specific killing use targeting multidrug-resistant bacteria.

There have been reports that existing plasmid-based CRISPR genome editing induces escape mutants, but a genetic change does not occur in target loci of these clones and a genome editing function has an error by mutation of delivery vectors, resulting in low bacterial mortality.

The present invention, compared with previously reported lipid-based non-covalent formulations, allowed the binding of each single molecule of the Cas9 protein to a carrier material by inducing a direct conjugation between Cas9 and the polymer, and thus solved a loading efficiency problem found in the case of previous non-covalent formulations, and can use only a minimal amount of a carrier material (2 wt % or less of a protein) since only one or two molecules of polymer carrier material (bPEI) were conjugated with each Cas9 molecule, and thus can minimize toxicity or side effects and can be administered at a higher dose, so that the present invention has higher delivery efficiency and specificity compared with existing plasmid-based formulations.

Advantageous Effects

The CRISPR nanocomplex for nonviral genome editing of the present invention has a size of several nanometers to several microns, enables intracellular delivery without external physical stimulation, and can be utilized for genome editing through nonviral routes with respect to target genes of cells. As a result, when used for preparation of animal model, microbiological engineering, cell engineering for disease treatment, or formulations for biological administration, the CRISPR Nanocomplex shows high intracellular delivery and gene editing efficiency, and can minimize problems, such as nonspecific editing, gene mutation, and induction of cytotoxicity and biotoxicity.

BRIEF DESCRIPTION OF THE DRAWINGS

FIGS. 1a, 1b, 1c, 1d and 1e show the nucleotide sequence of recombinant Cas9 endonuclease (SpCas9) obtained from cloned Streptococcus pyogenes of the present invention. The combined sequence of FIGS. 1a-1e represents SEQ ID NO: 1. The sequence contains 6× His, FLAG, nuclear localization sequence (NLS), SpCas9, and green fluorescent protein (GFPuv) from the N- to C-terminus. The sequence in lower case shows the GFP region.

FIGS. 5a and 5b show the nucleotide sequence of the mecA gene template for preparing the sgRNA sequences targeting the mecA gene. The combined sequence of FIGS. 5a and 5b represents SEQ ID NO:2.

FIG. 6 shows primer sequences (SEQ ID NOs:3 and 4) for amplifying the mecA gene template.

FIG. 7 shows the nucleotide sequences of templates (SEQ ID NOs: 5-7) for sgRNA synthesis.

FIG. 8 shows the primer sequences (SEQ ID NOs: 8-11) for sgRNA template synthesis.

MODE FOR CARRYING OUT THE INVENTION

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1: Preparation of Carrier Material-Conjugated CRISPR Enzyme Protein 1-1. Expression and Purification of SpCas9 Protein The Cr-Nanocomplex (CRISPR nanocomplex) system for the efficient delivery of genome editing cargo into bacteria was developed using a complex of a polymer-derivatized Cas9 protein and sgRNA.

First, for the expression of the SpCas9 protein, the SpCas9 gene obtained from lentiCRISPR (Addgene) was cloned into pET21a (Novagen). The primers 5'-GGG-CATATGGGCAGCAGCCATCACCATCATCACCAC-GATTACAAAGACGATGACGATAAG ATGGCC-3' (SEQ ID NO: 12) and 5'-CCCAAGCTTTTTCTTTTTTGCC-TGGCCG GCCTTT-3' (SEQ ID NO: 13) were used for SpCas9, and 5'-CCCAAGCTTATGAGTAAA GGAGAAGAAC-3' (SEQ ID NO: 14) and 5'-CC-CAAGCTTTTATTTGTAGAGCTCATCCA-3' (SEQ ID NO: 15) were used for the green fluorescent protein (GFPuv).

The SpCas9 contains 6× His, FLAG, nuclear localization sequence (NLS), SpCas9, and green fluorescent protein (GFPuv) from the N- to C-terminus. The cloned sequence was confirmed by DNA sequencing. After transforming the expression vector into BL21-(DE3) *E. coli* competent cells, the cells were inoculated in Luria-Bertani (LB) broth (containing 100 μg/ml ampicillin), grown at 30° C. overnight ($OD_{600}$=0.4), and added with 0.5 mM isopropyl β-D-1-thiogalactopyranoside (IPTG) to induce SpCas9 expression. Cells were harvested after culture for 16 h followed by centrifugation at 5,000 rpm for 10 min, and treated with lysis buffer (50 mM $NaH_2PO_4$, 300 mM NaCl, 10 mM imidazole, 0.05% β-mercaptoethanol, pH 8.0) and with a procedure (41% duty, pulse of 2 s and rest of 5 s for a total of 30 min on ice).

The cell lysate was then incubated with Ni-NTA agarose beads (Qiagen) to bind the His-tagged SpCas9, washed, and eluted with buffer containing 50 mM $NaH_2PO_4$, 300 mM NaCl, 200 mM imidazole, 0.05% β-mercaptoethanol (pH 8.0).

The eluent was then dialyzed against storage buffer (50 mM Tris HCl, pH 8.0, 200 mM KCl, 0.1 mM EDTA, 20% glycerol, 1 mM DTT, and 0.5 mM PMSF) for a total of 12 h with buffer change every 2 h, and stored at −70° C. Recombinant Cas9 endonuclease from *Streptococcus pyogenes* (SpCas9) was obtained by transformation of expression plasmid into *E. coli* competent cells, followed by purification through affinity chromatography. The sequence of cloned SpCas9 is shown in FIG. 1.

Figure 2:
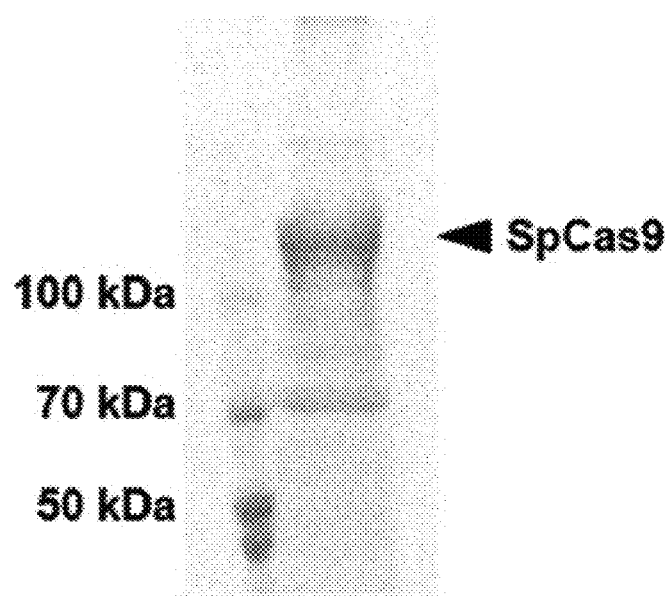
FIG. 2 shows the SDS-PAGE results of the expressed and purified SpCas9 protein of the present invention. The size of SpCas9 was observed to be about 190 kDa.

The purified SpCas9 was analyzed by SDS-PAGE electrophoresis. The SDS-PAGE results of the purified SpCas9 protein of the present invention is shown in FIG. 2. The size of SpCas9 was observed to be about 190 kDa.

Figure 3:
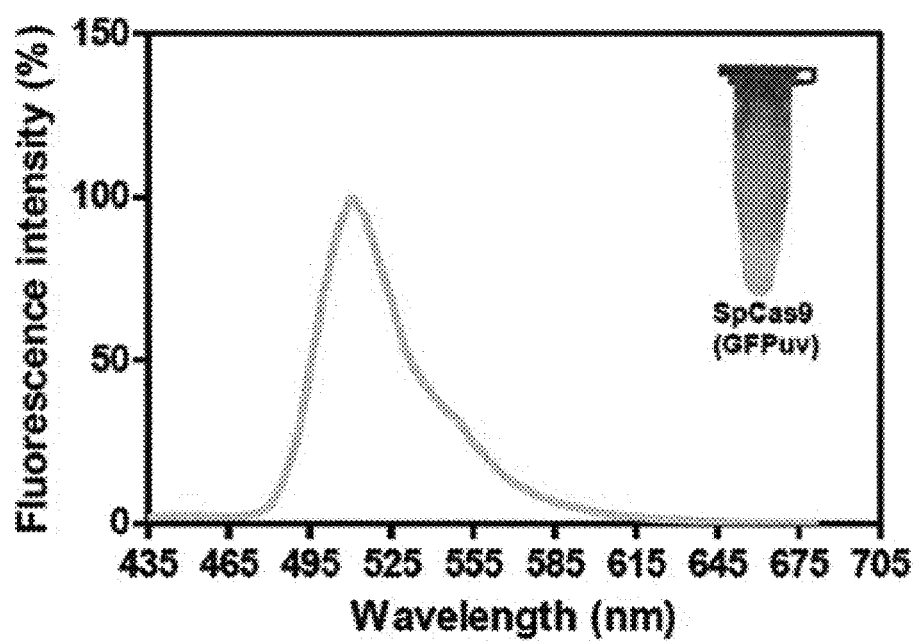
FIG. 3 shows the results of the fluorescence of GFP fused SpCas9 protein of the present invention observed under a UV illuminator.

The GFP fluorescence of the SpCas9 was also confirmed by observation under a UV illuminator (FIG. 3).

1-2. Design and Synthesis of Single Guide RNAs (sgRNAs)

Design of sgRNAs

Figure 4A:
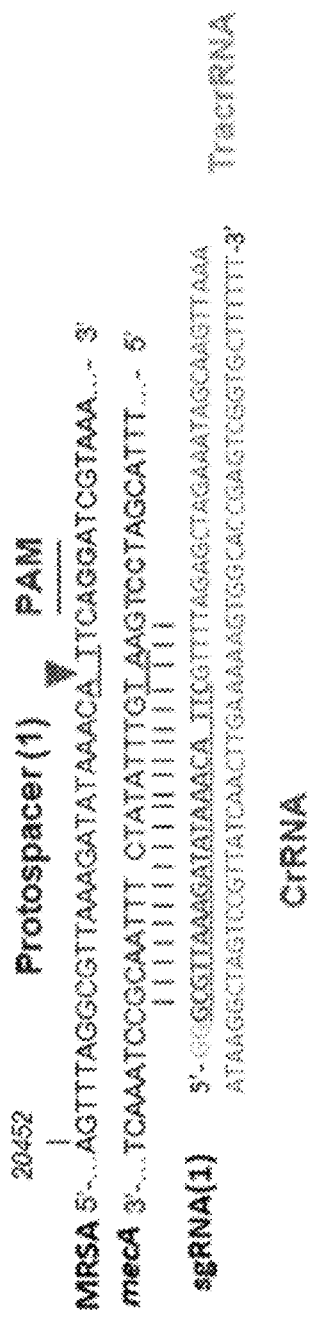
FIGS. 4a, 4b and 4c show single guide RNA (sgRNA) sequences (1 to 3) targeting the mecA gene (SEQ ID NO:12). Portions of sgRNA(1), sgRNA(2), and sgRNA(3) are shown as SEQ ID NOs: 13-15, respectively.
Figure 4B:
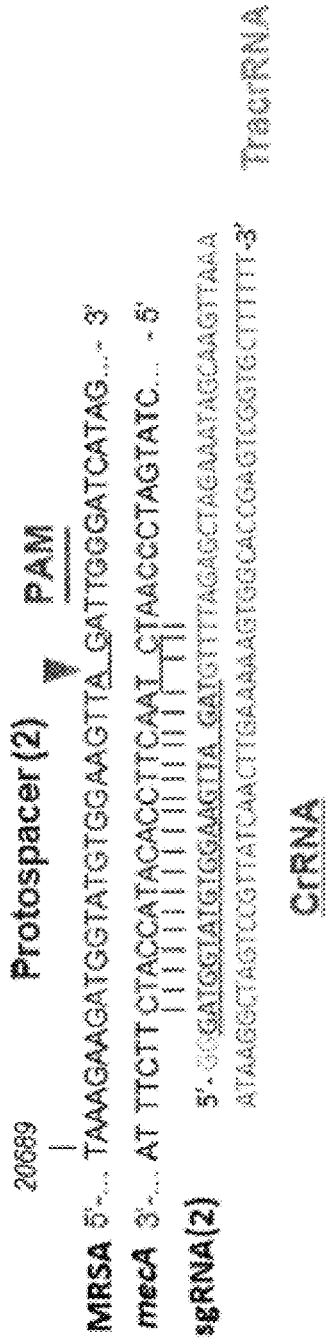
Figure 4C:
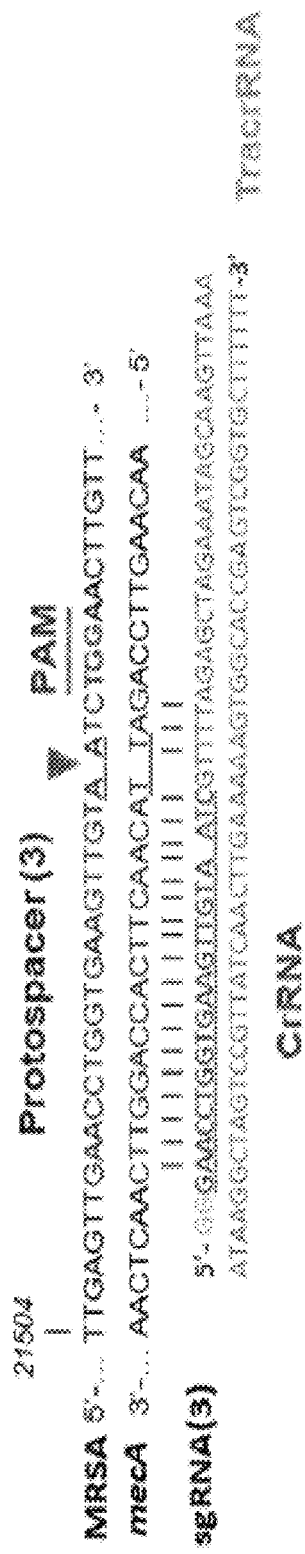

Single guide RNAs (sgRNAs) targeting the mecA gene in MRSA was designed to induce double-strand breakage in the bacterial genome by SpCas9. Three different sgRNA sequences were determined according to various target sites within the mecA gene as protospacers (FIG. 4). The protospacer regions were all adjacent to a protospacer-adjacent motif (PAM) sequence (NGG), from which target cleavage would occur at the site three bases upstream.

sgRNAs included a CrRNA for targeting mecA (CRISPR RNA), and a trans-activating RNA sequence (TracrRNA). A linker (GG) was also included in the 5' end. Templates for the sgRNAs were prepared by repeating 30 cycles of annealing at 60° C. for 40 s and extension at 72° C. for 30 s using the HelixAmp Power-Pfu (NanoHelix) and oligonucleotide primers (Bioneer), followed by gel extraction (QIAquick, Qiagen). In vitro transcription was performed using the phage T7 RNA polymerase (Promega) at 37° C. for 120 m. Sequences of the amplicons and primers are shown in FIG. 4. The transcribed sgRNAs were purified by precipitation using 5 M ammonium acetate, followed by ethanol precipitation.

Figure 9:
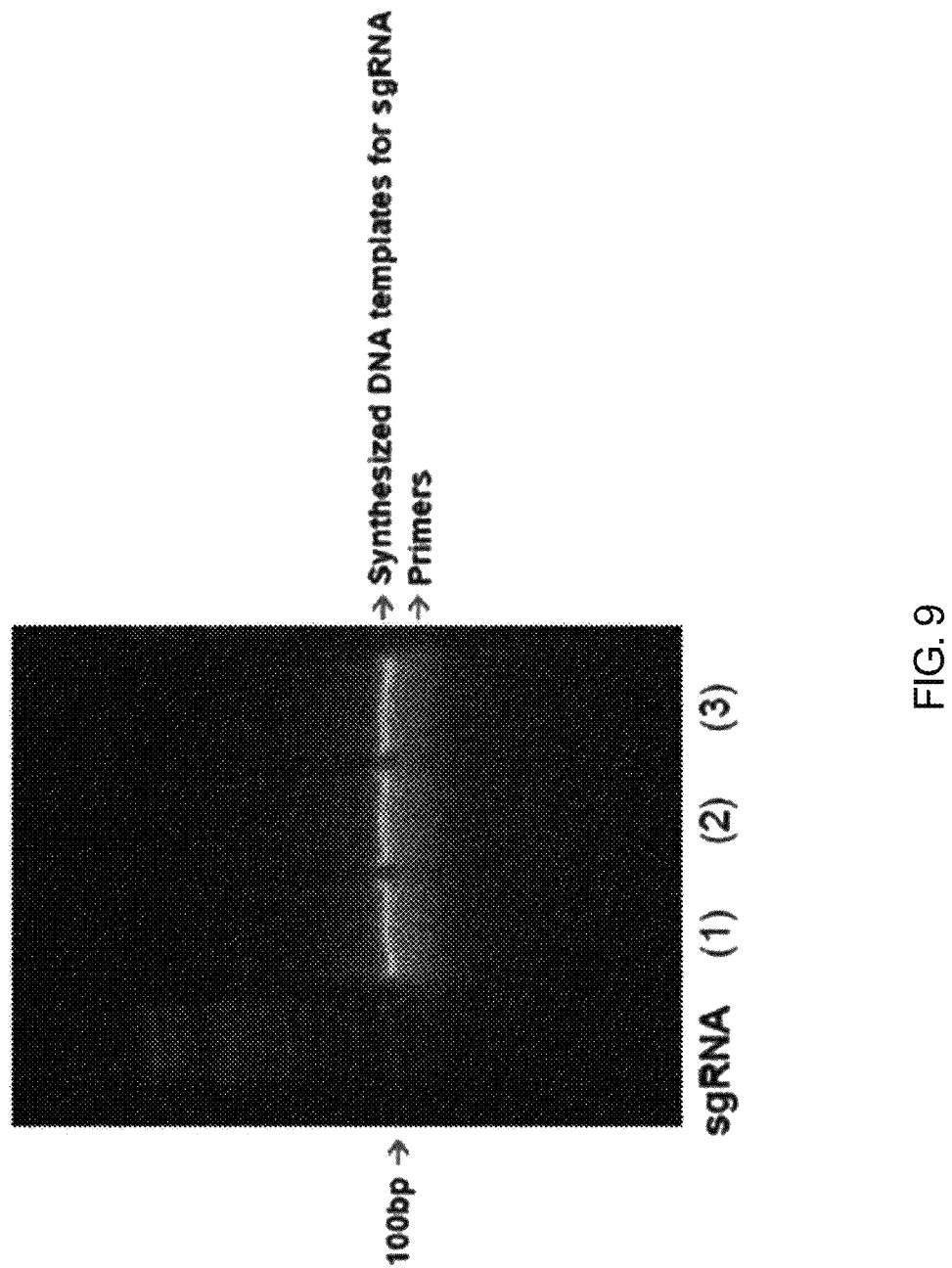
FIG. 9 shows electrophoresis results of the synthesized sgRNAs.

For preparation of sgRNAs, DNA templates for respective sgRNA were first synthesized using the primers shown in FIG. 8 for in vitro transcription. The DNA template for each sgRNA included a T7 promoter region, a template region for CrRNA, and a template region for TracrRNA (FIG. 7). The synthesized DNA templates are shown in FIG. 9.

Figure 10:
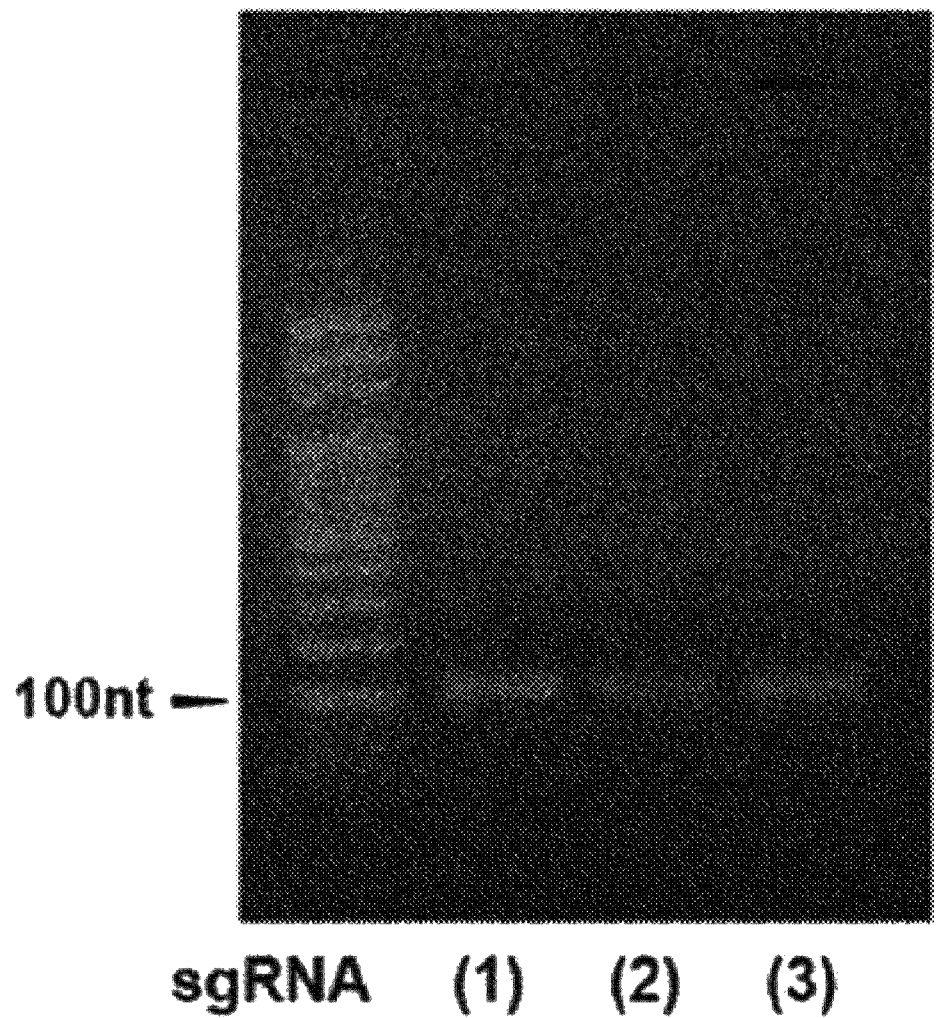
FIG. 10 shows the results of electrophoresis to confirm three kinds of sgRNAs synthesized in the present invention.

In vitro transcription was then performed using the synthesized DNA templates and T7 polymerase to produce the respective sgRNAs. FIG. 10 shows that three different types of sgRNAs—sgRNA(1), sgRNA(2), and sgRNA(3), all targeting different regions of mecA, were successfully synthesized. All three synthesized sgRNAs were shown to have sizes of ~100 nucleotides.

Selection of sgRNA

The functionality of the sgRNAs prepared above to guide double-strand cleavage was also examined. As the target DNA, a pure, cell free DNA solution was prepared by RT-PCR of the 1803 bp region within the mecA gene (FIG. 5) from the total RNA of cultured MRSA. sgRNA(1), sgRNA(2) and sgRNA(3) each were mixed with the purified native SpCas9 protein, and added with the PCR-amplified mecA target DNA, to induce endonuclease cleavage.

The sgRNA(3) exhibited the highest cleavage efficiency, with both fragments (648 bp and 1155 bp) appearing in the gel electrophoresis results. The sgRNA(2) showed a clear fragment right below the uncleaved DNA which corresponds to the 1463 bp fragment, but the other cleaved product was difficult to observe. For the sgRNA(1), neither of the cleaved products were visible, showing that either the efficiency was too low for detection, or the sgRNA was non-functional in inducing specific double-strand breakage. Thus, the sgRNA (3) was used for the formation of nanocomplexes of the present invention and further examination for bacterial delivery.

1-3. Bacterial Strains and Culture

MRSA strains CCARM 3798, 3803, 3877 were obtained from the Culture Collection of Antimicrobial Resistant Microbes (CCARM) and were used as target bacteria with drug resistance. MSSA strain KCTC 3881 was obtained from the Korean Collection for Type Cultures (KCTC), and used as the non-resistant strain. For culture, each bacterial strain was inoculated into tryptic soy broth (TSB, BD Biosciences) and cultured in suspension at 37° C. in a shaking incubator for 12-16 h. Bacterial growth and concentrations were determined by measuring the OD at 600 nm (0.4-0.6).

Example 2: Preparation of Polymer-Derivatized SpCas9

2-1. Preparation of SpCas9-bPEI

For the conjugation of polyethyleneimine as an anionic carrier material to genome editing protein Cas9 endonuclease, the following experiment was conducted.

Branched polyethyleneimine (bPEI, Mw 2,000 and 25,000) were activated by adding 16 mg of bPEI to 5 mg of sulfosuccinimidyl 4-(N-maleimidomethyl)cyclohexane-1-carboxylate (sulfo-SMCC, Thermo Scientific) in ultra-pure water, followed by reaction at 25° C. for 3 h (molar ratio of bPEI:sulfo-SMCC=1:10). The reaction solutions were then dialyzed against deionized water (MWCO 500-1,000, Spectra/Por) for 48 h, and the polyethyleneimine polymer having an amine group substituted with maleimide was freeze-dried (FD8508, IlshinBioBase).

In addition, for the production of Cas9 endonuclease using the genome editing protein as described above, the vector of Cas9 protein (SpCas9) derived from *Streptococcus pyogenes* was expressed in *E. coli*, followed by purification using histidine.

For the conjugation of polyethyleneimine to the genome editing protein (SpCas9), 2 mg of the purified SpCas9 protein was dissolved in 1.2 ml of phosphate buffer saline (PBS); the polyethyleneimine polymer activated by maleimide was reacted therein at a molar ration of 1:100 at pH 6.9 for 4 h at 4° C.; and then the final product (SpCas9-bPEI) was dialyzed against storage buffer (50 mM Tris HCl at pH 8.0, 200 mM KCl, 0.1 mM EDTA, 20% glycerol, 1 mM DTT, and 0.5 mM PMSF) for 24 h, and rapidly frozen in liquid nitrogen, and then stored at 80° C.

Figure 11:
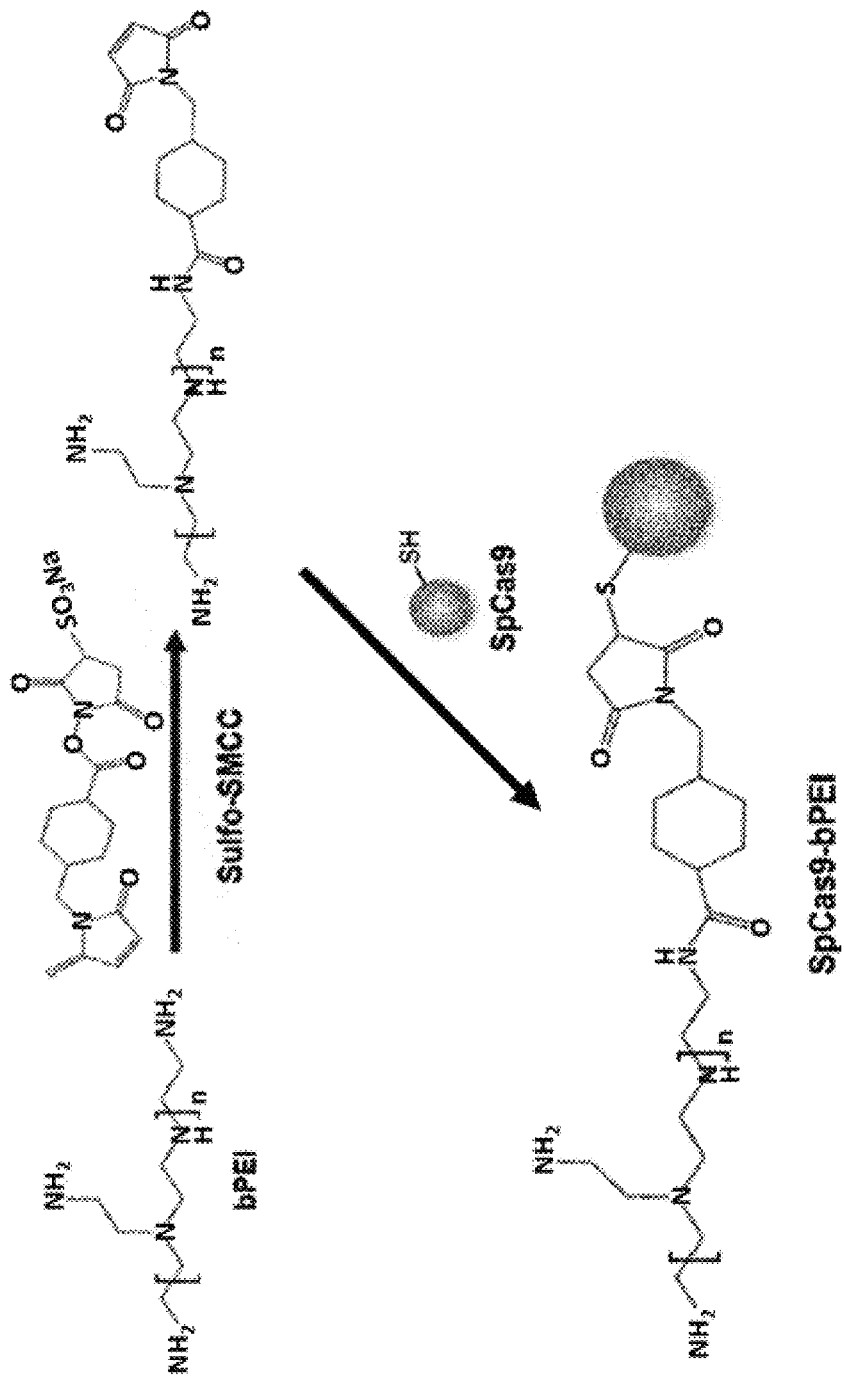
FIG. 11 is a schematic diagram of a conjugation procedure between SpCas9 and bPEI of the present invention.

A schematic diagram for the synthetic procedure of the SpCas9-bPEI is shown in FIG. 11.

The conjugation of bPEI onto Cas9 was confirmed by gel retardation using 0.5% agarose gel and 5% sodium dodecyl sulfate polyacrylamide gel electrophoresis (SDS-PAGE).

Figure 12:
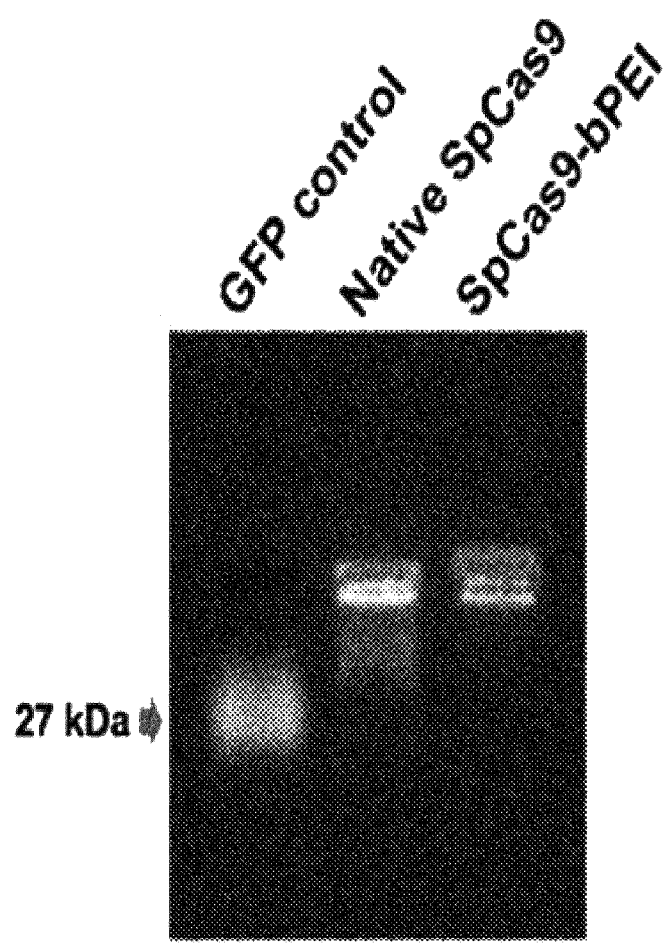
FIG. 12 shows the gel retardation assay results to confirm the successful conjugation of bPEI onto SpCas9.

FIG. 12 shows the gel retardation assay results to confirm the successful conjugation of bPEI onto SpCas9. As shown in FIG. 12, SpCas9 conjugated with bPEI (SpCas9-bPEI) appeared to migrate slightly to the (−) direction, which was opposite to native SpCas9 that showed substantial migration to the (−) direction. The gel retardation assay results for SpCas9-bPEI may be due to the change in mobility and the clustering of protein molecules, due to modification with the polymer. Although a maximum of two bPEI molecules can be conjugated onto each protein molecule by increasing the molecular weight of the protein by only 4,000 Da, such a slight change (1-2%) may substantially affect the mobility of the protein during electrophoresis due to structural or dimensional changes. The theoretical charge of the GFP-fused SpCas9 protein was expected to be highly negative. Since bPEI is highly cationic due to an extremely high density of amine functional groups, the conjugation of bPEI onto SpCas9 may either affect the molecular charge of the protein or induce their clustering by electrostatic protein-polymer interactions.

Figure 13:
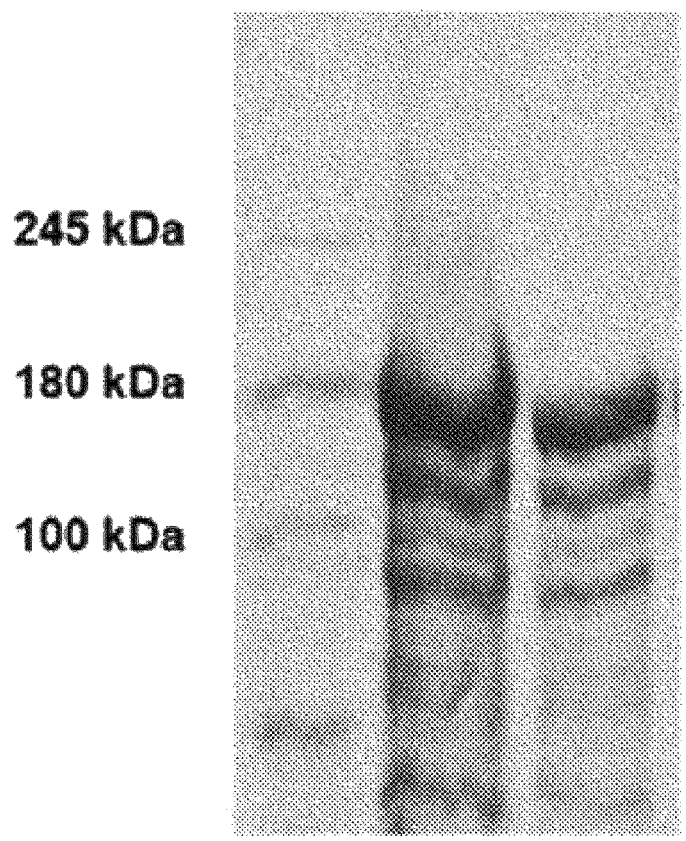
FIG. 13 shows the SDS-PAGE analysis results to confirm the successful conjugation of bPEI onto SpCas9.

In addition, the SDS-PAGE results to confirm the successful conjugation of bPEI onto SpCas9 are shown in FIG. 13. As shown in FIG. 13, SpCas9-bPEI and native SpCas9 appeared at similar regions, showing that covalently cross-linked SpCas9 proteins were not present after the conjugation reaction (FIG. 13). Therefore, it was confirmed that the conjugation of SpCas9 and bPEI was successfully achieved, and no crosslinkage occurred between SpCas9 protein molecules.

Example 3: Preparation and Characterization of CRISPR Genome Editing Nanocomplex (Cr-Nanocomplex)

3-1. Preparation of Cr-Nanocomplex

Figure 14:
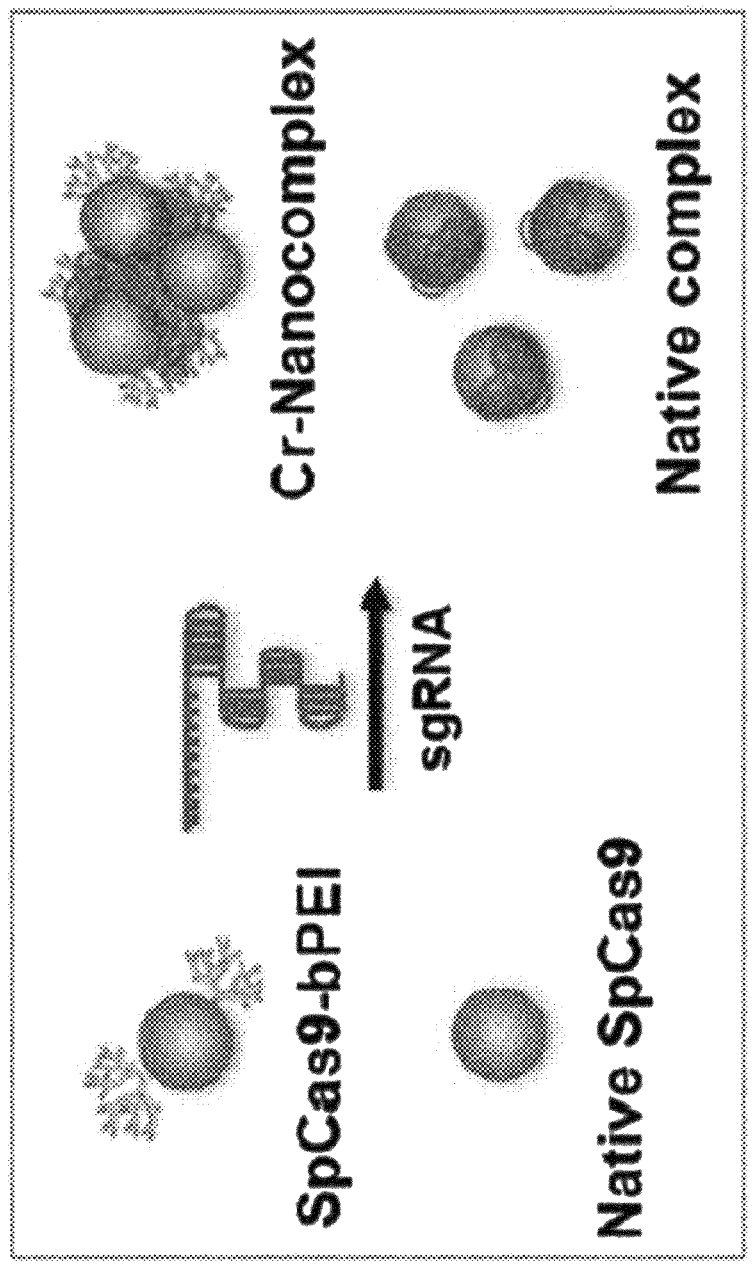
FIG. 14 is a schematic diagram showing the preparation of a complex between SpCas9-bPEI and sgRNA of the present invention (Cr-Nanocomplex) and, as a control, a complex between the unmodified SpCas9 protein and sgRNA (native complex).

For the preparation of Cr-Nanocomplex of the present invention, SpCas9-bPEI (990 nM) and sgRNA(3) (1.8 µM) were mixed in deionized water (pH 6.5), and incubated at 25° C. for 15 min in static condition. As the control, native SpCas9 (990 nM) was mixed with sgRNA(3) (1.8 µM) in the same condition as above. As a result, a nano-sized complex in which Spcas9-bPEI and sgRNA (3) are self-assembled was manufactured (FIG. 14). As the sgRNA, a sequence targeting antibiotic-resistant gene mecA of methicillin-resistant *Staphylococcus aureus* (MRSA) was used. The pH during the complexation was ~6.4, which was lower than the pKa (~8.6) of bPEI (2 kDa), and would protonate their amine functional groups to induce electrostatic binding with the anionic sgRNA.

Size Measurement and Zeta Potential Measurement of Complex

For dynamic light scattering (DLS) and zeta potential measurement, the complexed solutions were diluted in PBS or deionized water to a final concentration of 168 nM SpCas9 and 300 nM sgRNA(3), respectively. The hydrodynamic sizes and zeta potentials of the Cr-Nanocomplexes or native complexes were measured with ELSZ-2000ZS (Otsuka).

Figure 15:
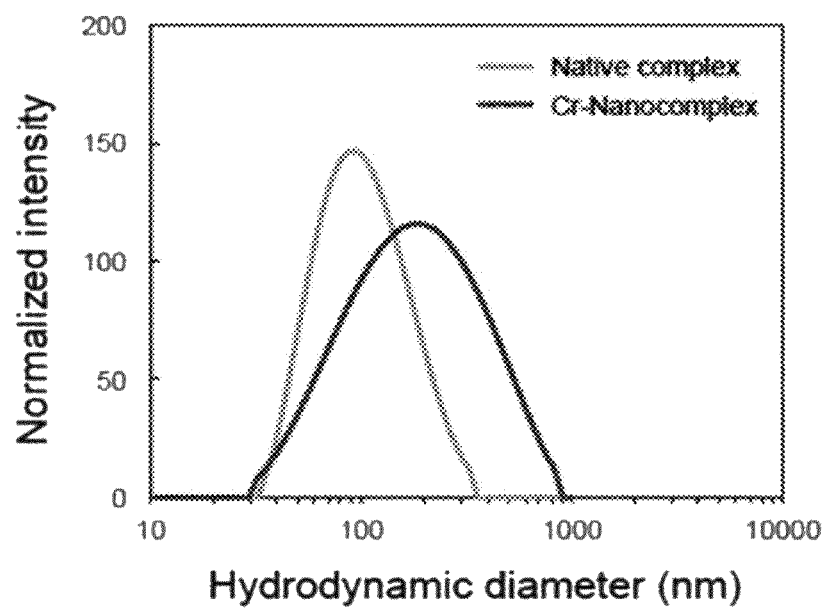
FIG. 15 shows the comparison of the particle size between the Cr-Nanocomplex of the present invention and the native complex.

The dynamic light scattering measurement results showed that the particle size (Z average) was 163.3 nm for the Cr-Nanocomplex, which was greater than 82.6 nm, the size of the native complex of the unmodified Cas9 protein and sgRNA (FIG. 15). These results confirmed that small, nano-sized protein-polymer conjugate/RNA complexes were successfully formed by the charge interaction between the negatively charged sgRNA and positively charged polymer within SpCas9-bPEI. Each complex would include several molecules of SpCas9-bPEI and sgRNAs, forming larger complex structures, unlike unmodified SpCas9 which would mainly exist as a single protein bound to a single sgRNA molecule.

The zeta potential values of the Cr-Nanocomplex and native complex both showed negative values, due to the presence of sgRNA bound to the surface of the protein, while the zeta potential of the Cr-Nanocomplex was relatively less anionic (−12.1 mV) compared to the native complex (−19.0 mV). In addition, the zeta potential of SpCas9-bPEI before complexation showed a positive value (+4.0 mV), which was a significant change from that of native SpCas9 (−17.2 mV), due to the introduction of the cationic polymer. The less anionic property of the Cr-Nanocomplex was expected to help improve the delivery into bacteria.

3-2. Cleavage Assay for Endonuclease Activity

To investigate whether the Cas9 endonuclease after polymer derivatization and Cr-Nanocomplex formation retained the functional activity in inducing double-strand DNA cleavage, an in vitro cleavage assay was performed using PCR-amplified template DNA derived from cultured bacteria.

First, MRSA and MSSA strains were cultured, and the total RNAs were extracted using the Trizol reagent (Invitrogen), and then reverse-transcribed using the amfiRivert cDNA Synthesis Platinum Master Mix (GenDEPOT) at 60° C. for 1 min (denaturation), 25° C. for 5 min (annealing), 55° C. for 60 min (extension), and 85° C. for 1 min (inactivation). cDNAs were then amplified with power pfu polymerase (Nanohelix) and specific primers for the mecA gene (Bioneer), using the following conditions: initiation at 95° C. for 2 min; 35 cycles of 95° C. for 20 s (denaturation), 59° C. for 40 s (annealing), 72° C. for 3 min 38 s (extension); and termination at 72° C. for 5 min.

The amplified template DNAs were then treated with SpCas9-bPEI or native SpCas9 complexed with sgRNA(3) at a 10:10:1 molar ratio of SpCas9:sgRNA:target DNA, followed by incubation in Cas9 nuclease reaction buffer (20 mM HEPES, 100 mM NaCl, 5 mM $MgCl_2$, 0.1 mM EDTA, pH 6.5) at 37° C. for 1 h. The final products were observed by agarose gel electrophoresis to confirm the presence and sizes of the DNA fragments.

Figure 16:
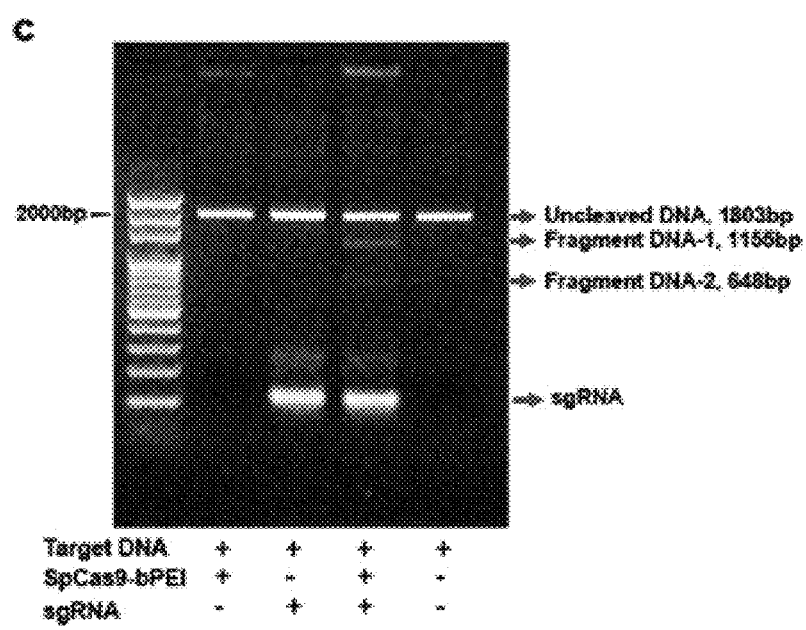
FIG. 16 shows the gel electrophoresis results after adding the synthesized target DNA together with the Cr-Nanocomplex to induce cleavage.

The results are shown FIG. 16.

As shown in FIG. 16, it was confirmed that one larger DNA fragment and one smaller DNA fragment appeared, which correspond to the expected sizes of 1155 bp and 648 bp, showing that SpCas9, even after direct covalent modification with bPEI and complexation with sgRNA, is able to induce double-strand cleavage of the target DNA.

3-3. Bacterial Delivery of Polymer-Derivatized SpCas9 and Confocal Microscopy

The polymer derivatization of Cas9 protein of the present invention was expected to increase the bacterial uptake compared with native Cas9. To demonstrate the delivery efficiency of polymer-derivatized SpCas9 into bacteria, SpCas9-bPEI was treated with in vitro cultured MRSA, followed by observation through confocal microscopy. MRSA strains 3798 and 3803 were cultured prior to treatment as mentioned above.

SpCas9-bPEI (200 nM) or native SpCas9 (200 nM) in PBS were treated to $1 \times 10^7$ of cultured MRSA. As the control, native SpCas9 simply mixed with bPEI was also used by first mixing concentrated SpCas9 with bPEI (Mw 2,000), incubating for 15 min at 25° C., and dilution (7×) in PBS for treatment (final concentration of SpCas9—200 nM, bPEI—3 µg/mL).

After incubation at 37° C. for 2 h with gentle agitation using a shaking incubator, bacteria were repeatedly washed with PBS after centrifugation to remove the residual complexes. Bacteria were then fixed in 4% paraformaldehyde solution, mounted onto microscopic slides using Vectashield (Vector Laboratories), and observed using a laser scanning confocal microscope (LSM780, Carl Zeiss). For quantification of relative uptake, bacteria were treated with the mixtures above at 1.7×107/mL for 4 h. As another control, native SpCas9 was also mixed with Lipofectamine 3000 (Thermo Fisher Scientific) according to the manufacturer's protocol (final concentration of SpCas9 at 400 nM). Low magnification images were obtained by confocal microscopy and the green fluorescence signals (SpCas9) were normalized to red fluorescence (PI stain) using ImageJ (NIH).

Figure 17:
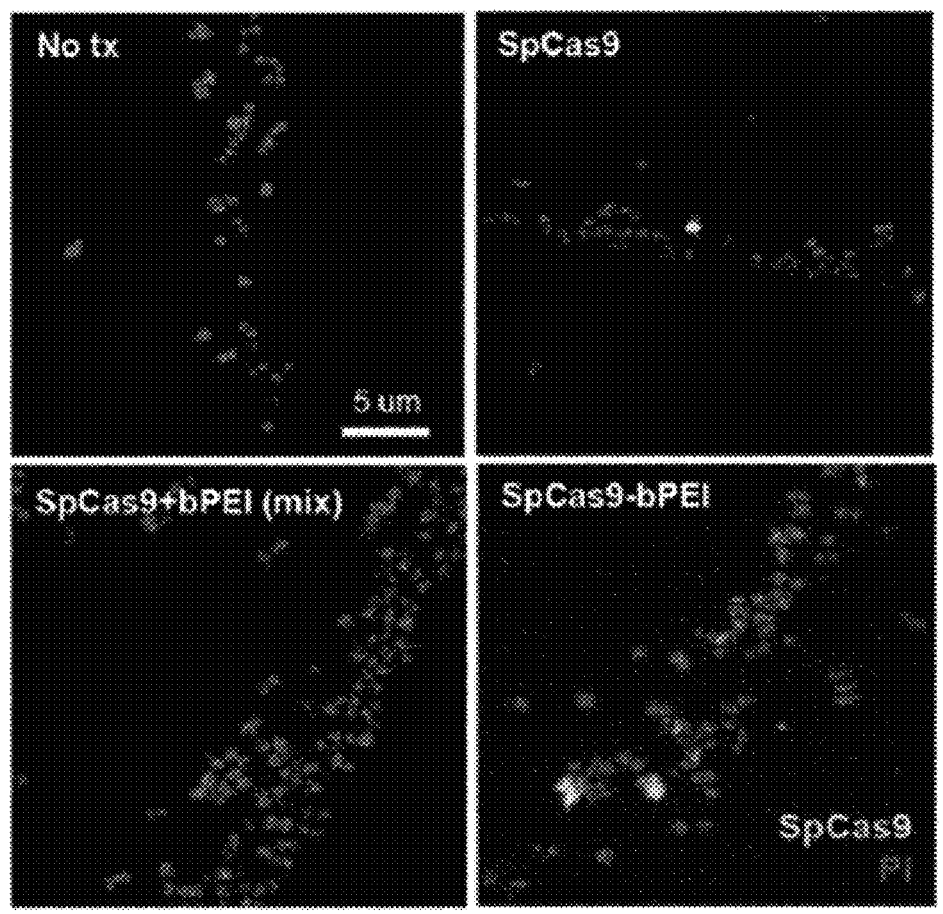
FIG. 17 shows the delivery results of the polymer-derivatized SpCas9 of the present invention into bacteria through observation by confocal microscopy.
Figure 18:
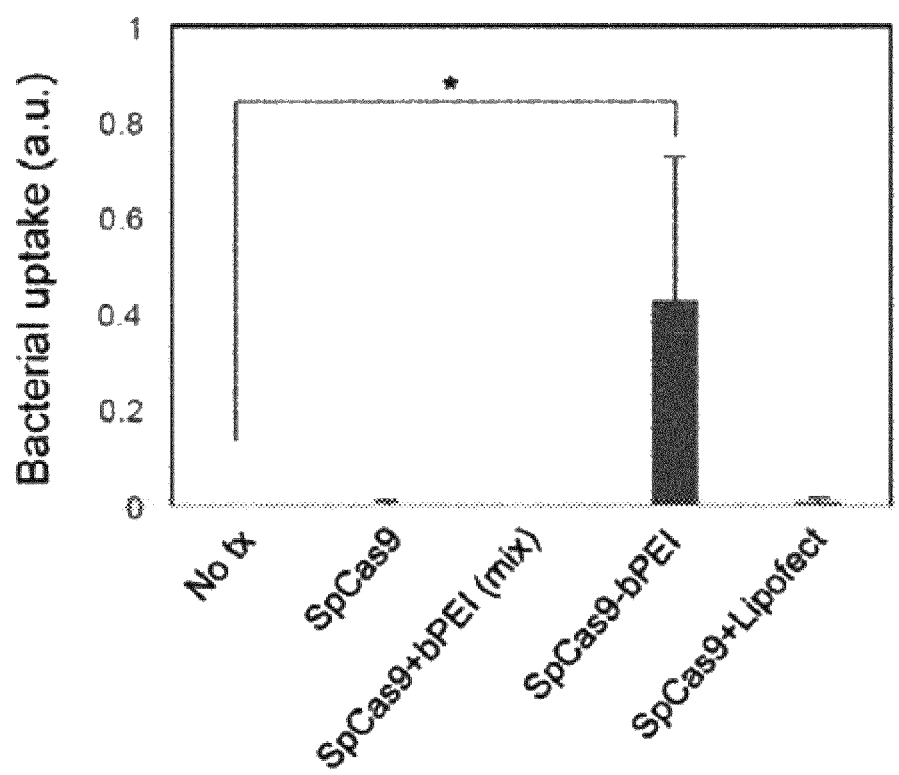
FIG. 18 shows the delivery efficiency of the polymer-derivatized SpCas9 of the present invention into bacteria, compared with a control group.

The results are shown in FIGS. 17 and 18.

As shown in FIG. 17, the Cas9 protein conjugated with polyethyleneimine of the present invention (SpCas9-bPEI) is an unmodified Cas9 protein (SpCas9), but SpCas9-bPEI was uptaken into bacteria at significantly high efficiency compared with a mixture of unreacted polyethyleneimine polymer and Cas9 protein (SpCas9+bPEI (mix)). In the case of SpCas9-bPEI of the present invention, bright green fluorescence from GFPuv was clearly observed adjacent to the nuclear stain, while native SpCas9 did not show any significant uptake. The native SpCas9 simply (noncovalently) mixed with bPEI (SpCas9+bPEI (mix)) as the control also did not show any sign of uptake.

Figure 19:
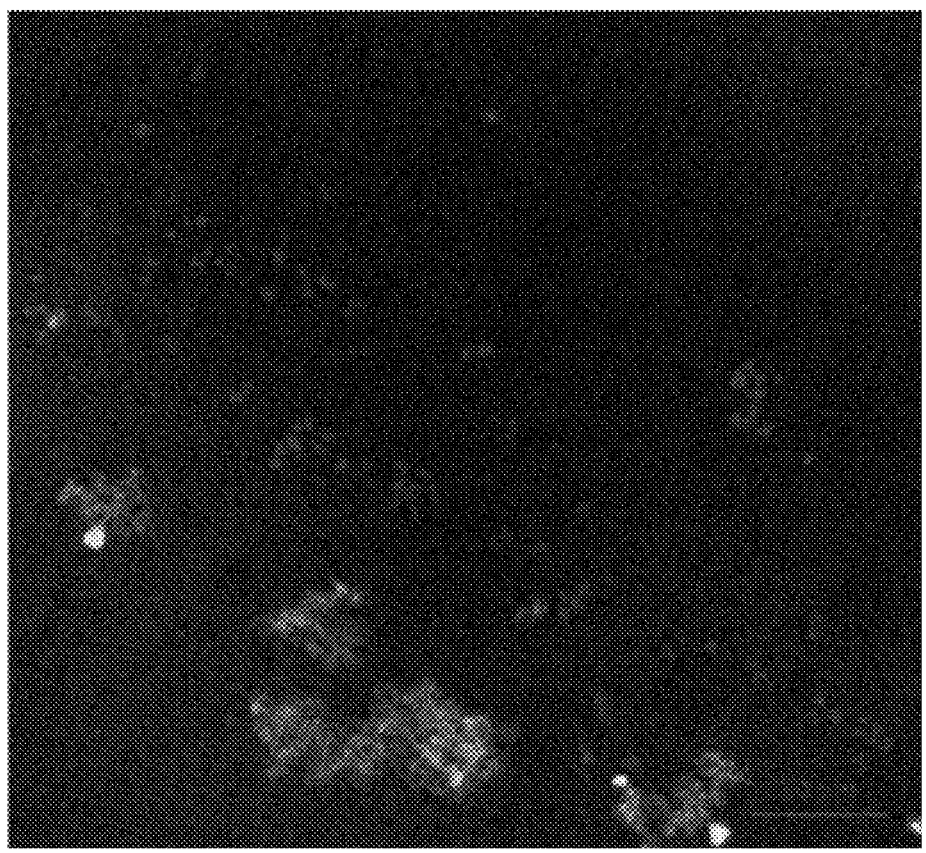
FIGS. 19 and 20 and FIGS. 21a, 21b, and 21c show 3D images reconstructed from confocal image sections showing the presence of SpCas9 in bacterial cells from the overlapping of fluorescence signals from spCas9 and nuclear stain in order to examine the bacterial uptake of the polymer-derivatized SpCas9.
Figure 20:
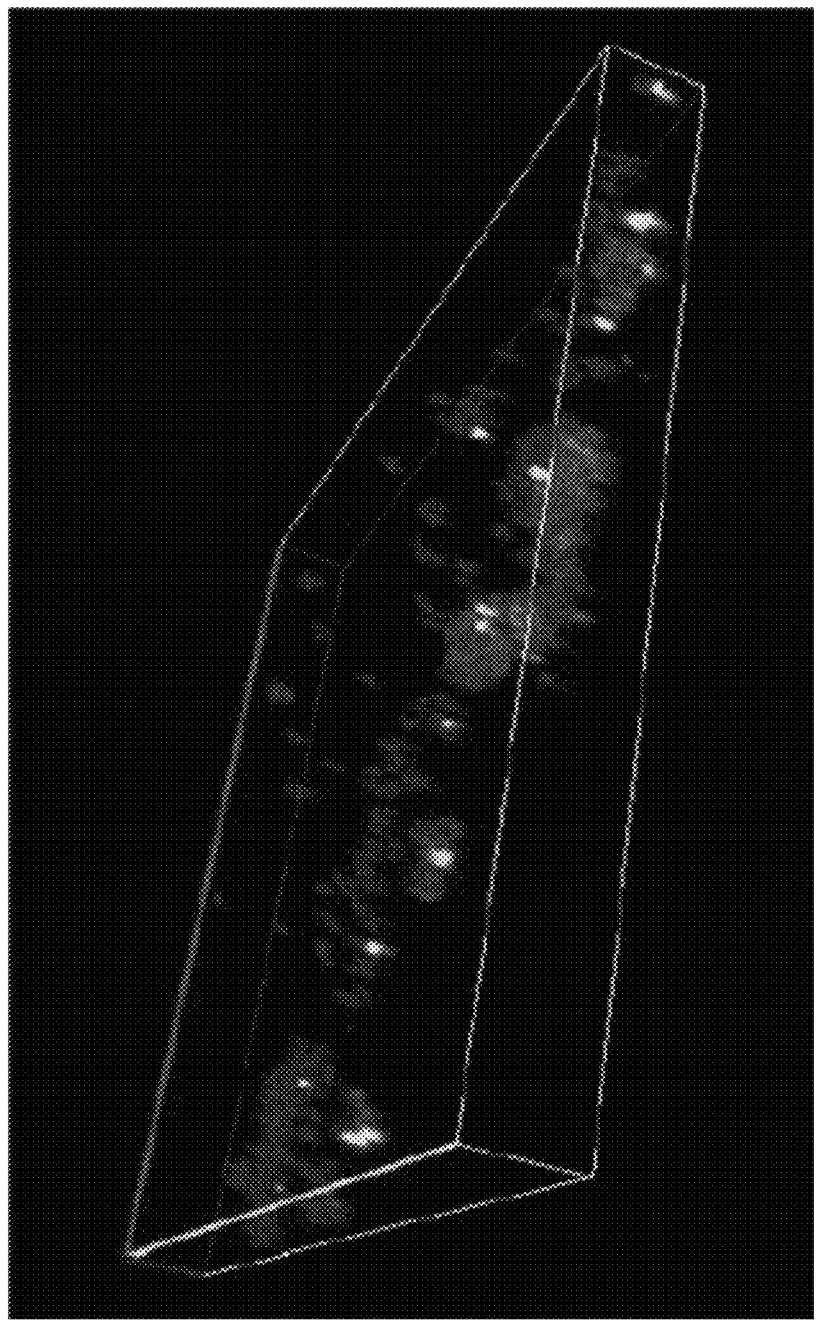

In addition, to further investigate the uptake of the polymer-derivatized SpCas9 into bacteria, confocal image sections were reconstructed into 3D images, showing the presence of SpCas9 within the bacterial cells from the overlap of fluorescence signals from the complex and nuclear stain (FIGS. 19 and 20).

Figure 21A:
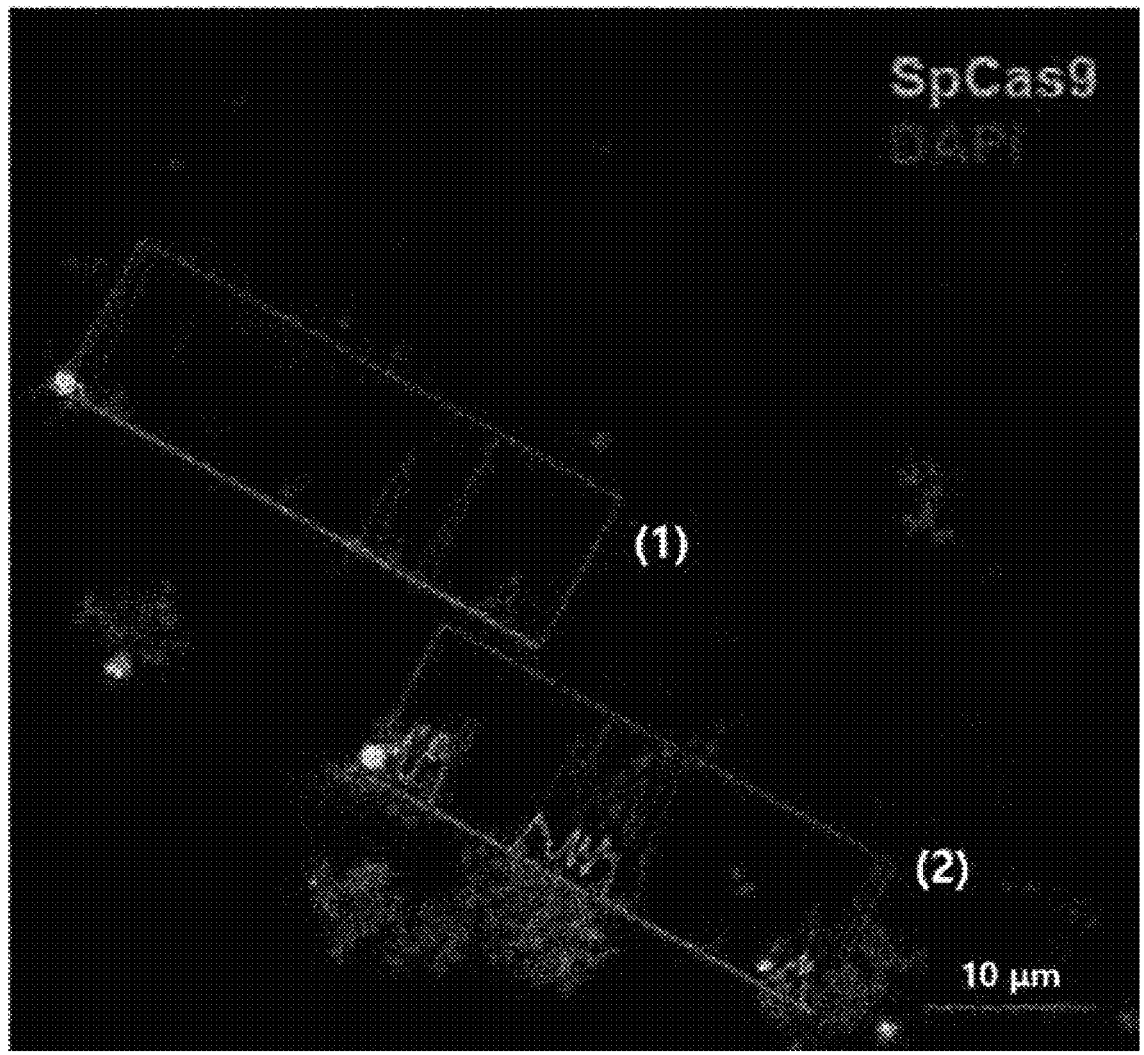
Figure 21B:
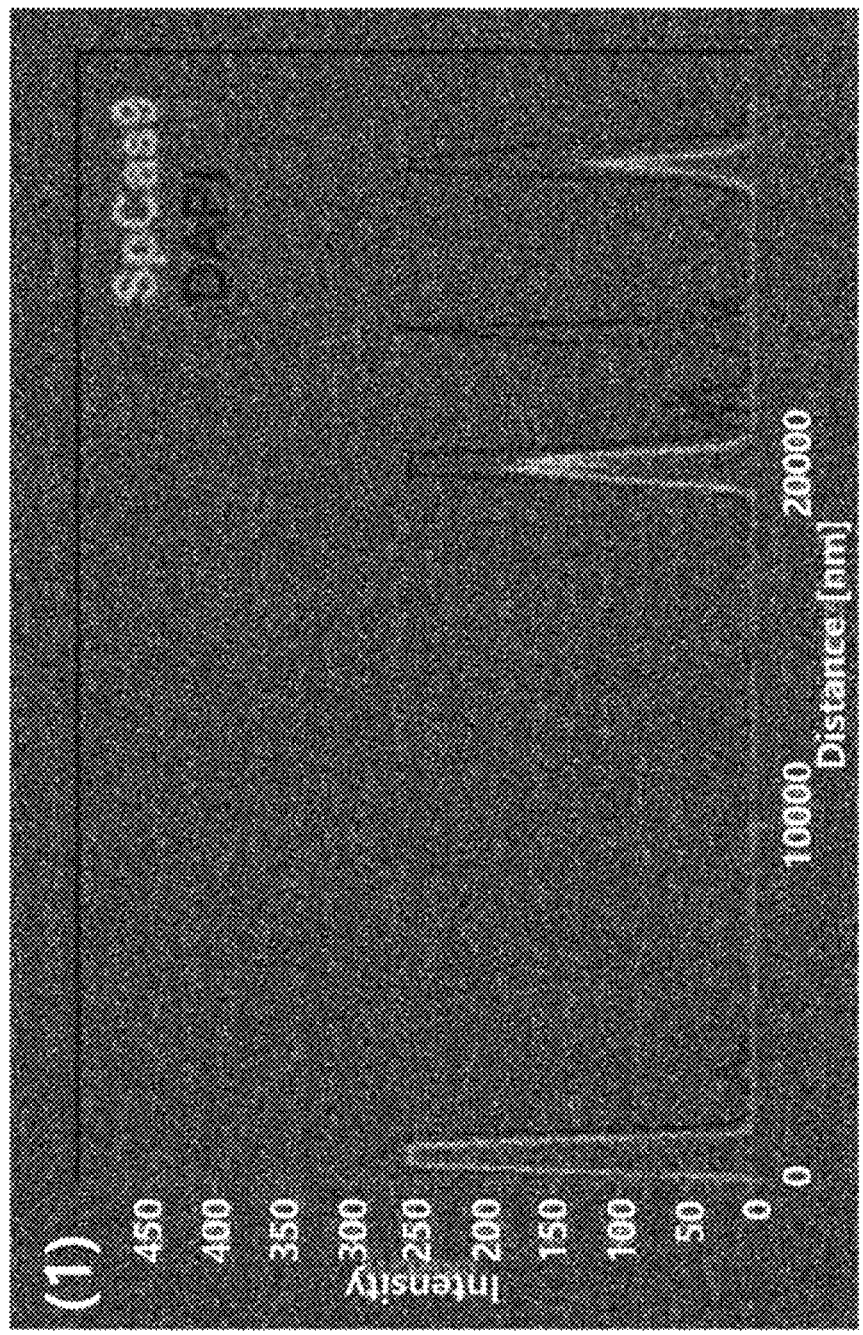
Figure 21C:
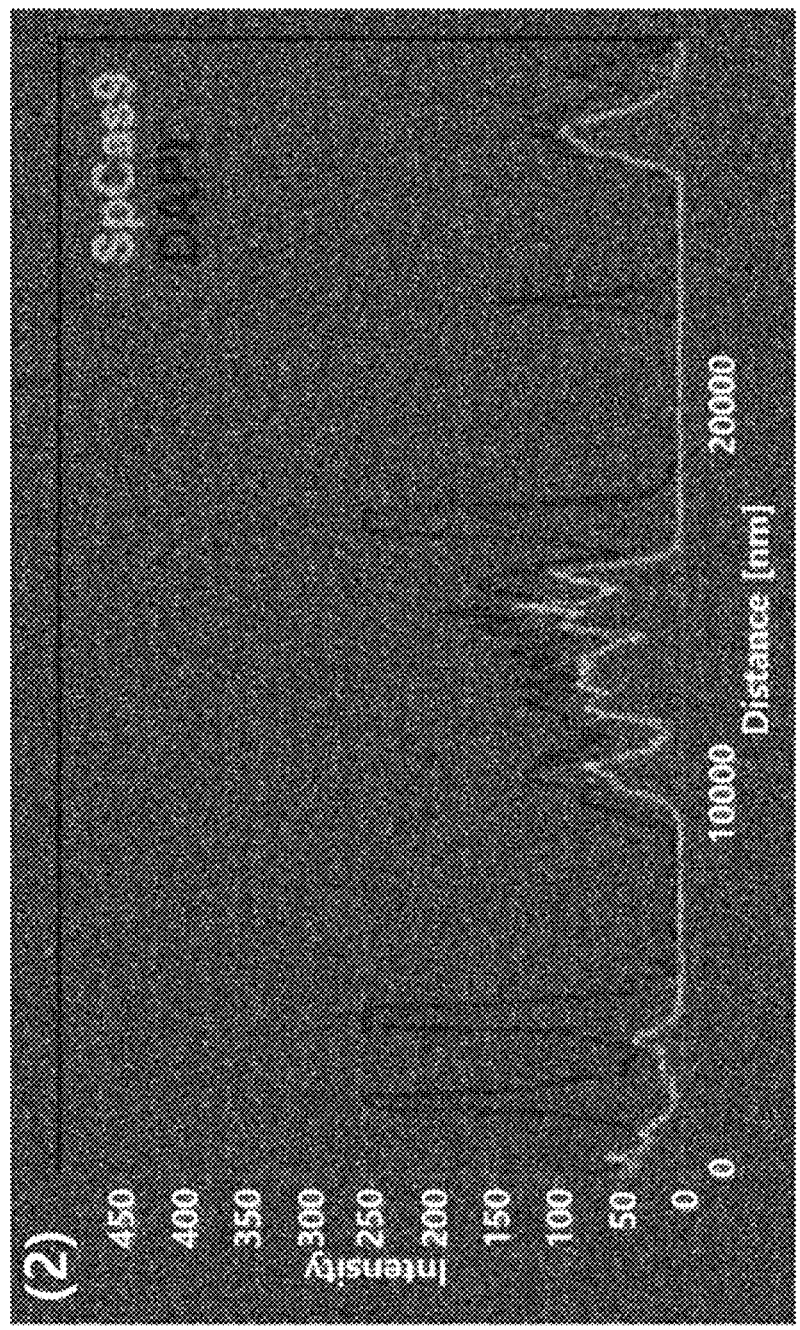

Histograms of the fluorescence signals were also obtained from different regions scanned within the confocal image, and as a result, signals from SpCas9 were present only at points where signals from the nuclear stain were also present (FIG. 21).

As shown in FIG. 19, relative uptake values were shown to be 0.4273 for SpCas9-bPEI, and 0.0041, 0.0001, and 0.0083 for native SpCas9, native SpCas9 simply mixed with bPEI, and native SpCas9 mixed with lipofectamine, respectively. The greatly increased uptake of the Cas9 protein upon bPEI conjugation may be due to the highly cationic property of the polymer, or the resultant increase in polarity of the protein.

Since the bPEI polymer is abundant in tertiary, secondary, and primary amine groups at high molecular densities, the interaction of SpCas9-bPEI to the negatively charged cell wall of gram-positive bacteria would substantially increase compared to native SpCas9. In addition, the presence of bPEI on the surface of SpCas9 allows the formation of clusters or condensation of the molecules. Overall, the enhanced binding of SpCas9 to the bacterial cell wall may be presumably by the penetration through the peptidoglycan and subsequently uptake through the cellular membrane, and thus would result in a higher chance of uptake. In addition, the strong cationic property of bPEI would electrostatically interact with the bacterial DNA, which was expected to allow the molecular attraction of SpCas9 towards the genomic target thereof.

Meanwhile, using conventional lipofectamine as the carrier has been shown to have limitations due to the low loading efficiency of the drug and a difficult release thereof into the cell.

The present inventors anticipated that these problems could be solved by covalent binding of the SpCas9 protein with a cationic polymer. So long as such a modification does not affect functional activity, the cationic polymer would be applied to each single molecule of protein while allowing the use of a minimal amount of carrier material. Another advantage is that an encapsulation process into the carrier material, which is required for a release step of the cargo for delivery, can be avoided.

Figure 22:
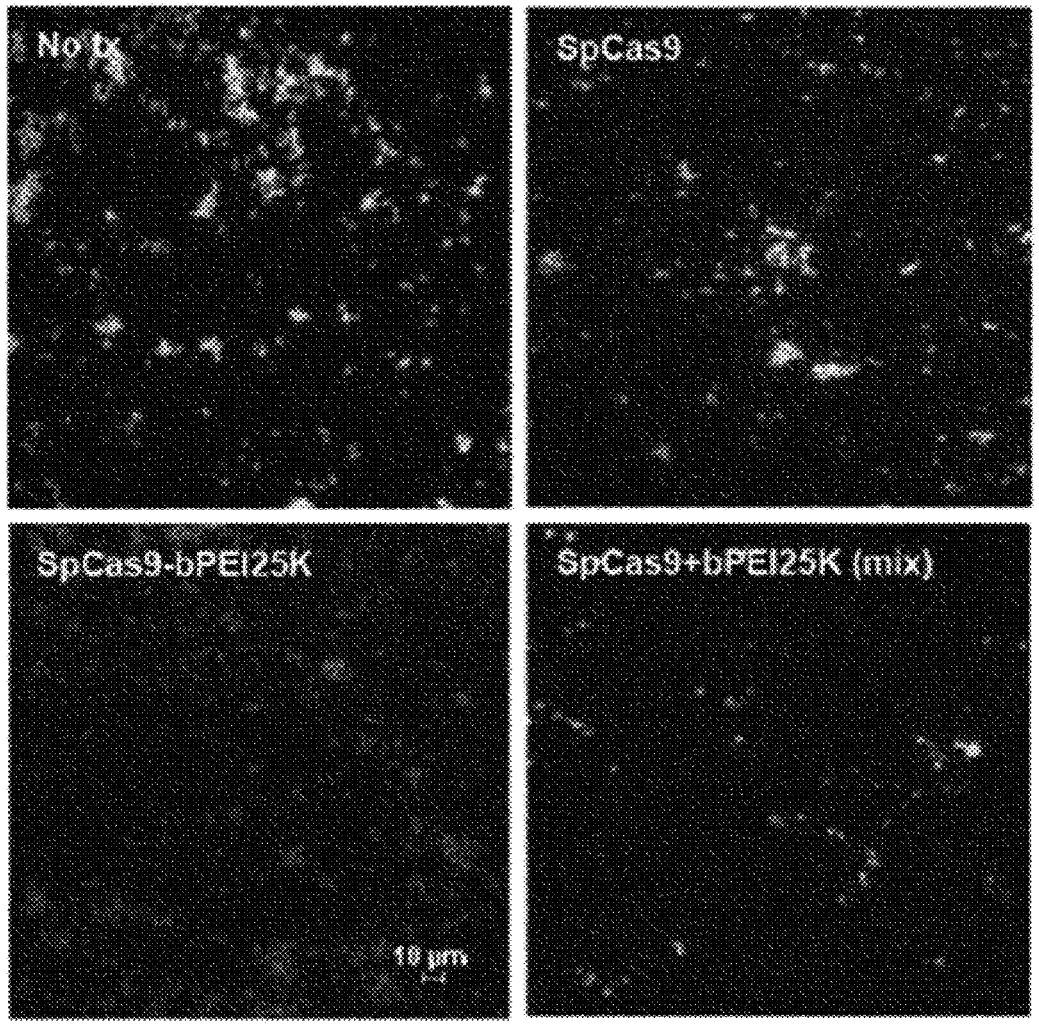
FIG. 22 shows the overlapping of fluorescence signals from SpCas9 and nuclear stain in order to examine the bacterial uptake of SpCas9 polymer-derivatized with a polymer carrier having a different molecular weight (Mw 25,000).

Further evidence could be confirmed in treatment experiments using SpCas9 modified with bPEI Mw 25,000. FIG. 22 shows that when modified with a larger bPEI polymer, the protein did not show any significant uptake when treated to bacteria. Since only modification with the smaller bPEI shows high delivery efficiency, it is evident that using a carrier material with a small molecular weight at an optimal amount is important to maximize delivery efficiency and minimize toxicity.

3-4. Animal Cell Delivery of Cr-Nanocomplex and Microscopy

The polymer derivatization of Cas9 protein of the present invention was expected to increase the uptake into mammalian cells compared with native Cas9. To validate the delivery efficiency of Cr-Nanocomplex into mammalian cells, the in vitro cultured animal cells were treated with SpCas9-bPEI and sgRNA, and observed by confocal microscopy. A549, HaCat, and Raw264.7 animal cells were cultured in the 8-well chamber at $1\times10^4$ cells 30 h before treatment. Jurkat animal cells were cultured in a 48-well cell culture plate.

The cultured mammalian cells were treated with SpCas9-bPEI2000/sgRNA (168 nM), SpCas9-bPEI25000/sgRNA (168 nM), or native SpCas9/sgRNA (168 nM) in PBS. As another control, native SpCas9/sgRNA (168 nM) was mixed with Lipofectamine RNAiMAX (Thermo Fisher Scientific) according to the manufacturer's protocol (final concentration of SpCas9/sgRNA at 168 nM each). Each experiment group was incubated using a cell incubator at 37° C., 5% $CO_2$ for 1-1.6 h, and then repeatedly washed three times with PBS to remove remaining complexes. The cells were then fixed in 4% paraformaldehyde solution, mounted onto microscopic slides using Mounting Medium (Vector Laboratories), and observed using a laser scanning confocal microscope (LSM780, Carl Zeiss). As a result, low magnification images were obtained by confocal microscopy, and green fluorescence signals (SpCas9) and blue fluorescence (DAPI-nuclear stain) could be confirmed.

Figure 23:
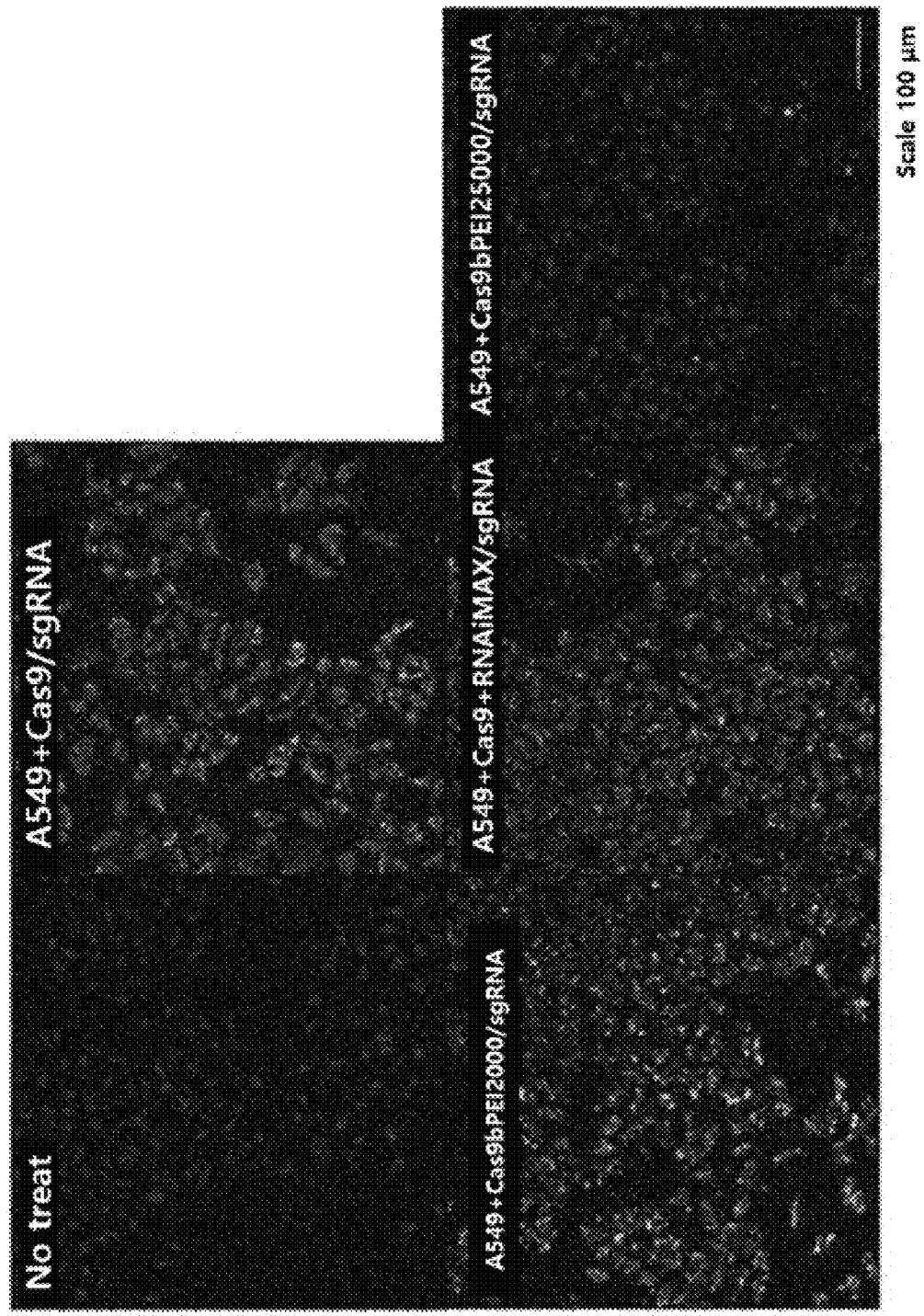
FIG. 23 shows the confocal microscopy observation and analysis results of the uptake efficiency of the Cr-Nanocomplex in A549 cells.
Figure 24:
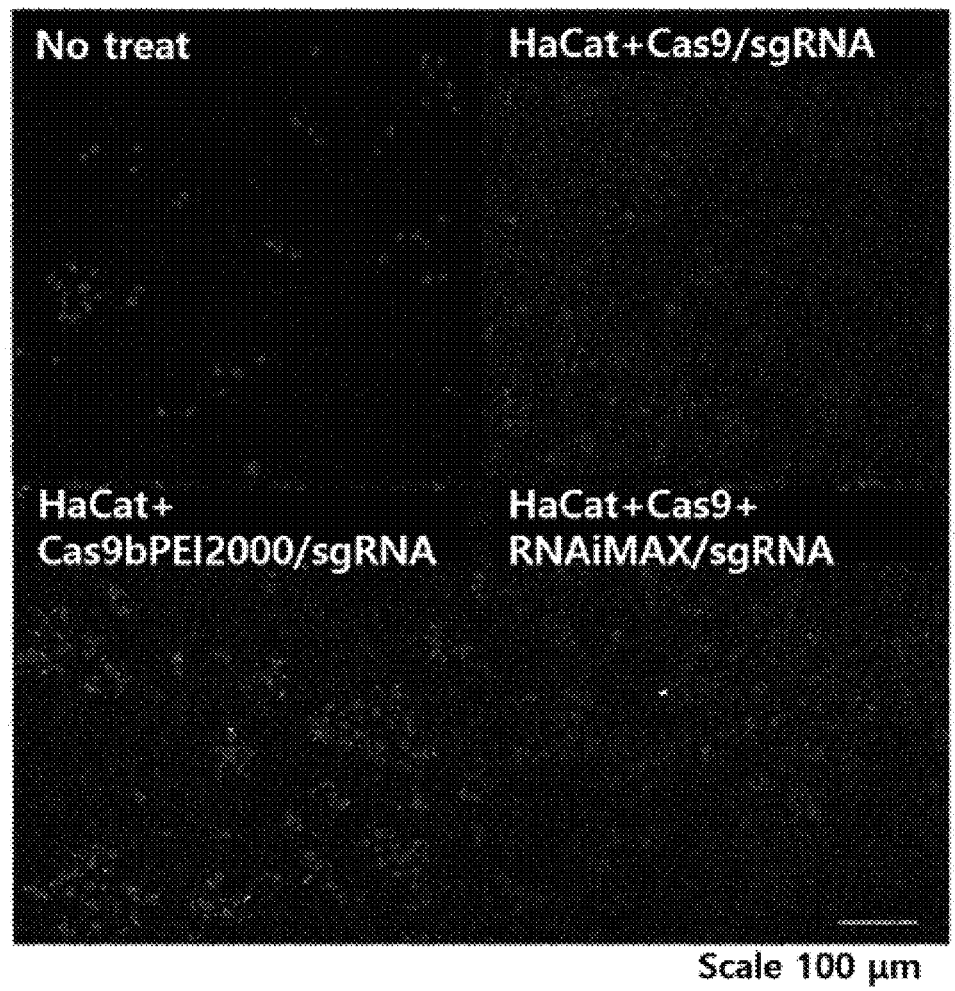
FIG. 24 shows the confocal microscopy observation and analysis results of the uptake efficiency of the Cr-Nanocomplex in HaCat cells.
Figure 25:
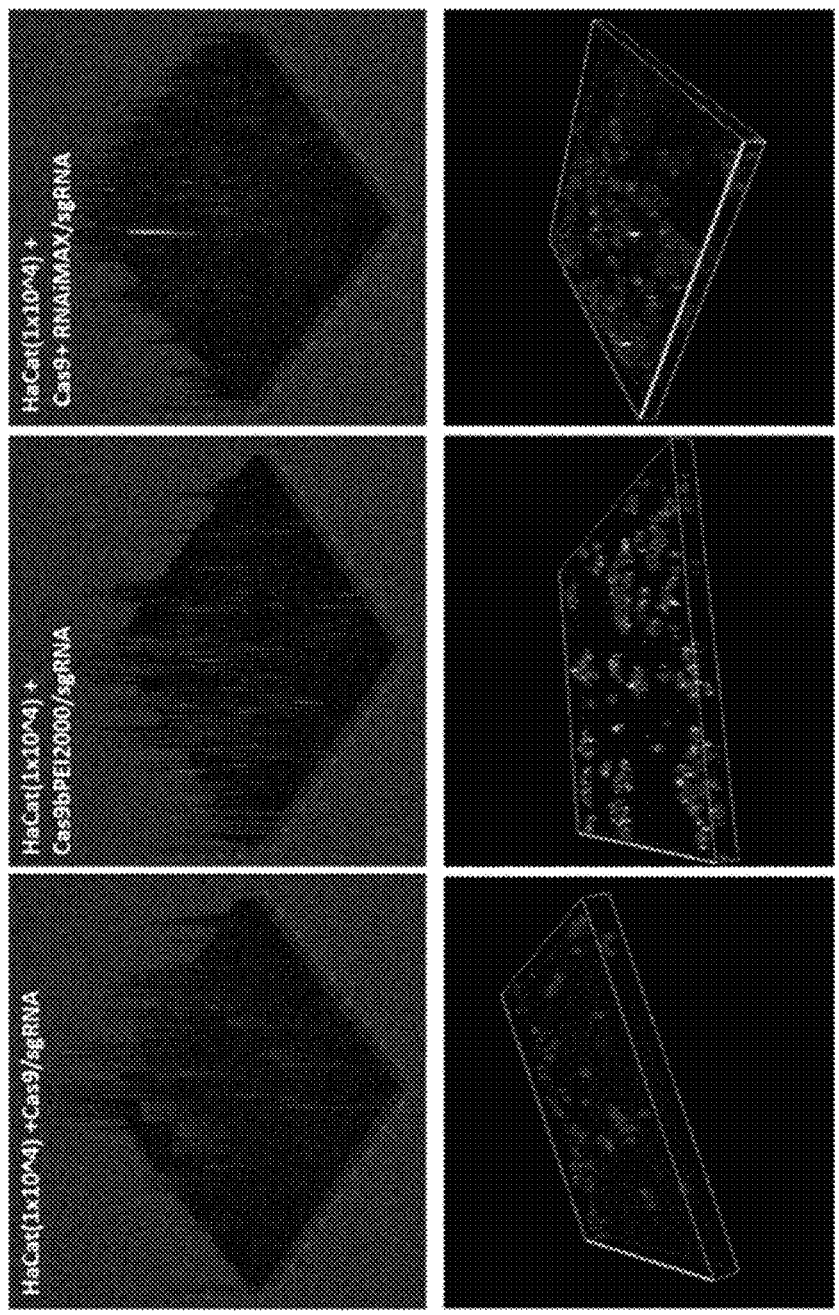
FIG. 25 shows 3D images reconstructed from confocal image sections showing the presence of the complex in animal cells from the overlapping of fluorescence signals from Cr-Nanocomplex and nuclear stain in order to examine the uptake of the Cr-Nanocomplex into HaCat cells.
Figure 26:
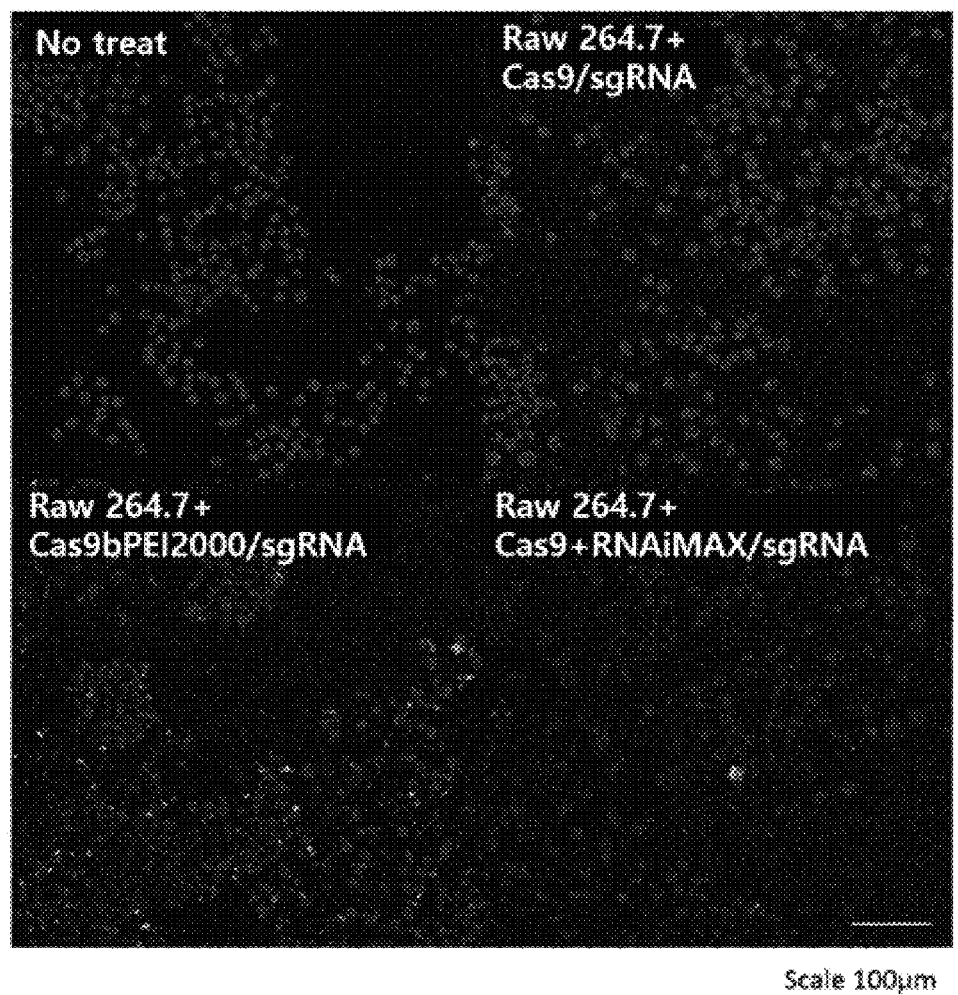
FIG. 26 shows the confocal microscopy observation and analysis results of the uptake efficiency of the Cr-Nanocomplex in Raw 264.7 cells.
Figure 27:
FIG. 27 shows the confocal microscopy observation and analysis results of the uptake efficiency of the Cr-Nanocomplex in Jurkat cells.
Figure 28:
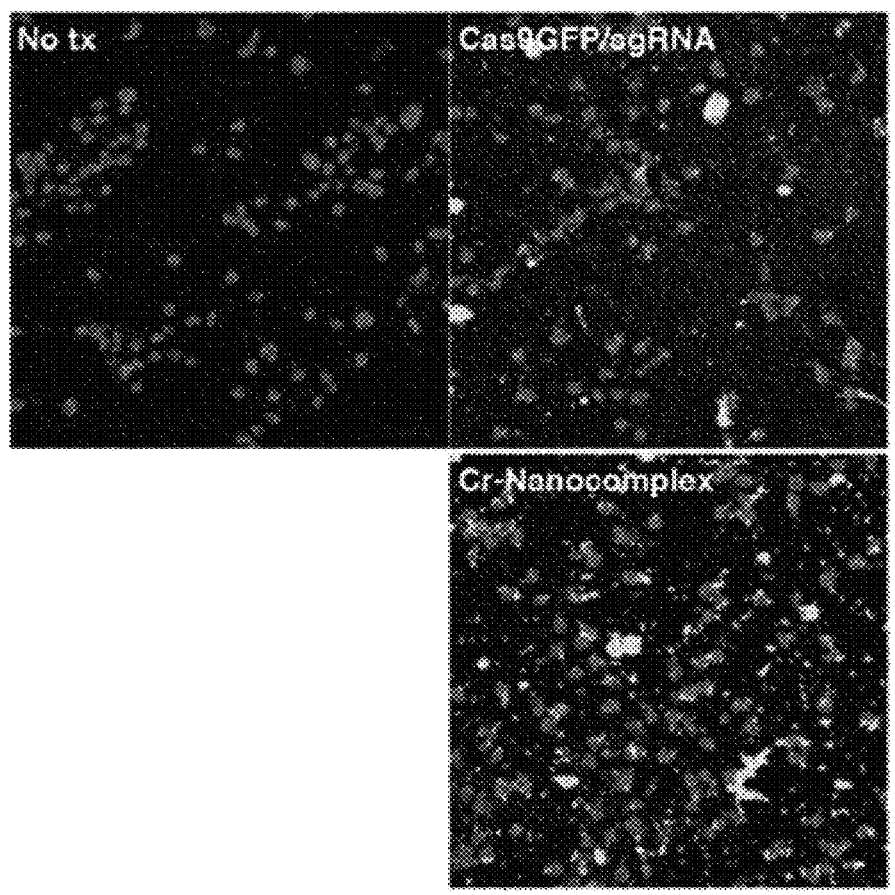
FIG. 28 shows the confocal microscopy observation and analysis results of the uptake efficiency of Cr-Nanocomplex in neural stem cells.
Figure 29:
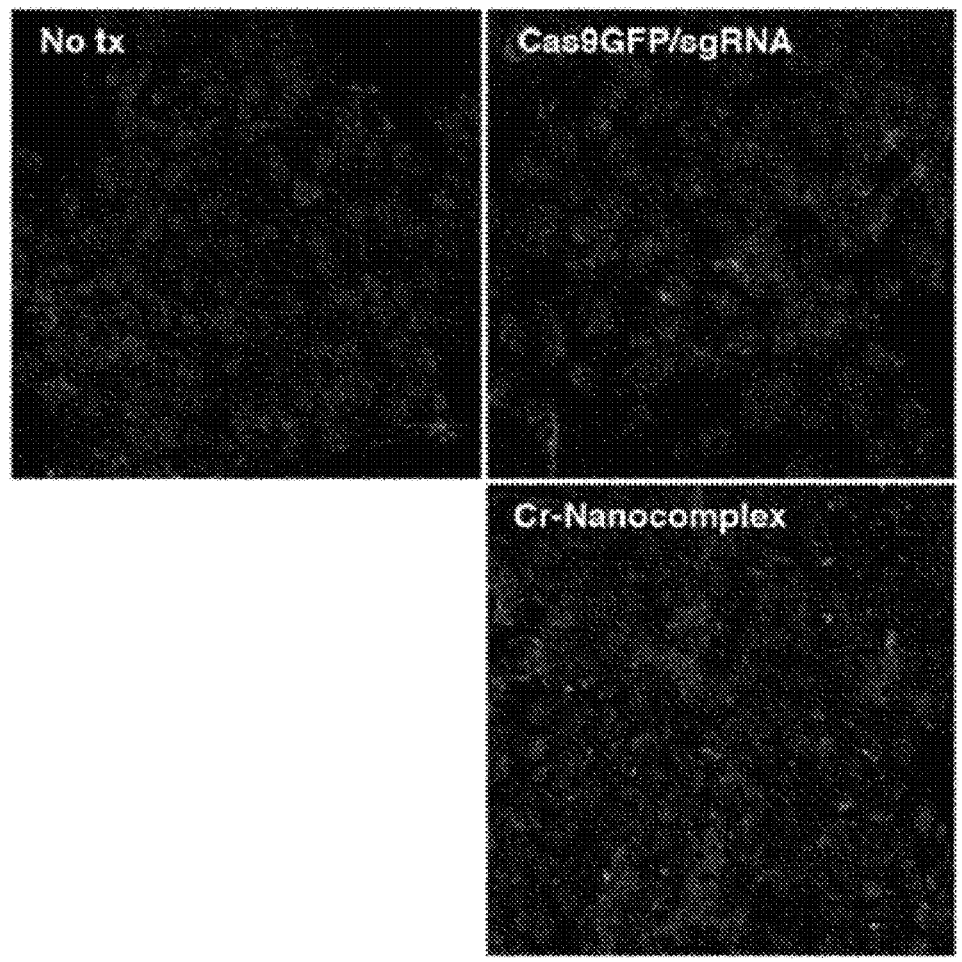
FIG. 29 shows the confocal microscopy observation and analysis results of the uptake efficiency of Cr-Nanocomplex in induced pluripotent stem cells (iPSCs).

As shown in FIG. 23, it can be confirmed that the Cas9 protein conjugate with polyethyleneimine (Mw: 2000) (SpCas9-bPEI)/sgRNA complex of the present invention showed successful uptake into A549 animal cells at significantly high efficiency compared with the unmodified Cas9 protein (SpCas9)/sgRNA complex, and also showed significantly high uptake even compared with a mixture with lipofectamine RNAiMAX. As another control, in the case of the treatment with SpCas9-bPEI25000/sgRNA (bPEI, Mw 25,000, 12.5-fold), clear intracellular uptake was not observed. In addition, also in cases where HaCat animal cells were treated, as shown in FIG. 24, it can be confirmed that Cas9 protein conjugate with polyethyleneimine (SpCas9-bPEI)/sgRNA complex of the present invention showed successful uptake into animal cells at significantly high efficiency compared with the unmodified Cas9 protein (SpCas9)/sgRNA complex and, as another control, the mixture with lipofectamine RNAiMAX. To further investigate the intracellular uptake of the Cr-Nanocomplex, confocal image sections were reconstructed into 3D images, showing the presence of the complexes within HaCat animal cells from the overlap of fluorescence signals from the complex (SpCas9/sgRNA: green fluorescence) and nuclear stain (DAPI: blue fluorescence) (FIG. 25). FIG. 25 confirmed that the Cas9 protein conjugated with polyethyleneimine (SpCas9-bPEI)/sgRNA complex of the present invention showed the most overlapping of green fluorescence signal (SpCas9) and blue fluorescence (DAPI-nuclear stain). The same results were also obtained for Raw 264.7 animal cells, and FIG. 26 confirmed that the GFPuv bright green fluorescence from Cas9 protein was clearly observed adjacent to the nuclear stain for the SpCas9-bPEI/sgRNA complex of the present invention, while native SpCas9 showed relatively weak fluorescence. As shown in FIG. 27, when immunocyte Jurkat animal cells were treated, the SpCas9-bPEI/sgRNA complex of the present invention, compared with the unmodified Cas9 protein (SpCas9)/sgRNA complex, showed greatly increased efficiency, and showed slightly increased intracellular uptake compared with a mixture with lipofectamine RNAiMAX. As shown in FIG. 28, it was observed that, also for human body-derived neural stem cells, the SpCas9-bPEI/sgRNA complex of the present invention showed a significantly high Cas9 fluorescence signal compared with the unmodified SpCas9/sgRNA complex, indicating a significantly high cell uptake effect. Also for human-derived induced pluripotent stem cells (iPSCs), the native SpCas9/sgRNA complex showed no cell uptake effect, but the SpCas9-bPEI/sgRNA complex of the present invention showed a significant cell uptake effect (FIG. 29). The delivery efficiency of SpCas9-bPEI/sgRNA or SpCas9/sgRNA complex can be confirmed by GFP signals of the SpCas9 recombinant protein, and for counterstain for all cells, the nucleus was stained with DAPI, and the cytoplasm was stained with rhodamine-phalloidin in FIGS. 28 and 29.

3-5. Evaluation of Genome Editing Efficiency by the Cr-Nanocomplex

The present inventors investigated whether the Cr-Nanocomplex edits bacterial genome and targets antibiotic resistance. Cultured MRSA (strains 3798 and 3803) were in vitro treated with Cr-Nanocomplex formed of sgRNA targeting mercA and SpCas9-bPEI, and the bacterial growth was examined in subsequent culture in selective media. The cultured MRSA strains were verified to be resistant to both methicillin and oxacillin.

As an experimental group, the Cr-Nanocomplexes of the present invention were prepared by mixing SpCas9-bPEI (990 nM) with sgRNA (3) (1.8 µM) and incubation for 15 min. As the control, native SpCas9 (990 nM) was mixed with sgRNA(3) (1.8 µM) in the same condition as above. A conventional lipid-based formulation as another control was also prepared by adding the native complex (50 µl) with Lipofectamine RNAiMAX (15.8 µL, Thermo Fisher Scientific), according to the manufacturer's protocol. As controls, ones containing protein only (without sgRNA), SpCas9-bPEI only, or native SpCas9 only were also prepared at 990 nM were also prepared.

All samples were diluted 6× in tryptic soy broth (final concentration of SpCas9:sgRNA=165 nM:300 nM), followed by treatment with $5\times10^6$ of MRSA at 37° C. for 4 h with gentle agitation. The treated bacteria were washed with PBS, diluted (100×) in TSB containing 6 µg/mL oxacillin, and incubated at 37° C. for 90 min in a shaking incubator. Bacterial growth was determined by measuring the OD value at 600 nm (Nanophotometer, Implen) after 90 min of incubation.

The bacteria treated with the nanocomplex were also diluted (105×) in PBS, spread onto MRSA agar plates containing 6 µg/mL oxacillin, and incubated at 30° C. for 21 h, and the colony forming unit (CFU) was counted.

In the case where bacteria treated with the Cr-Nanocomplex were cultured in suspension or on an agar medium containing oxacillin (6 µg/mL), the clones with broken double-stranded DNA could not grow and the unaffected clones would form bacterial colonies. A schematic diagram of the experimental procedure is shown in FIG. 28.

The growth rates were determined from the measurement of $OD_{600}$ values, after suspension culture of the bacteria treated with the Cr-Nanocomplex (FIG. 29). As shown in FIG. 29, it is shown that treatment with the Cr-Nanocomplex of the present invention results in significant inhibition of growth, that is, a 32% decrease compared with the treatment with SpCas9-bPEI without sgRNA as the control.

Figure 30:
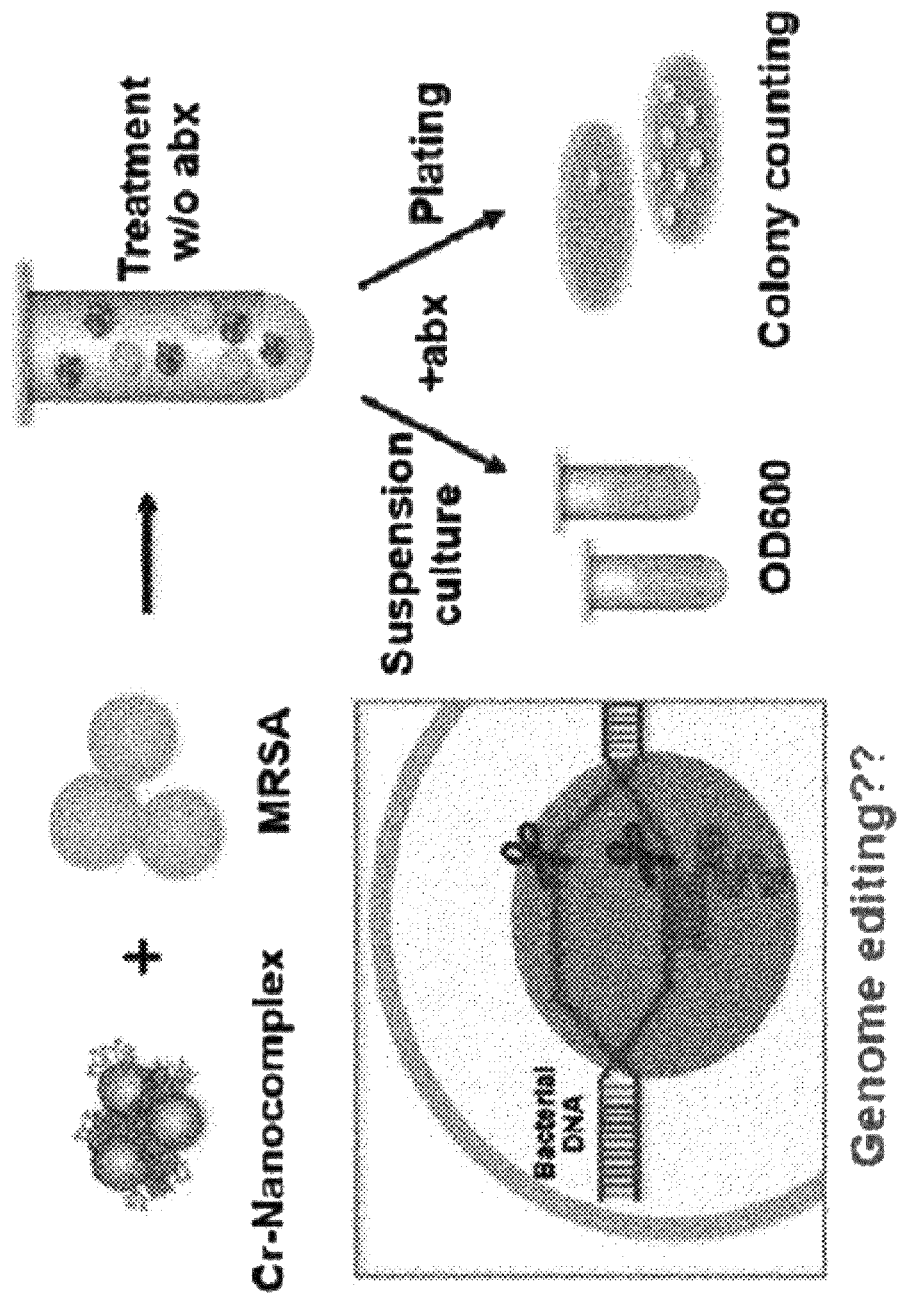
FIG. 30 is a schematic diagram illustrating the experimental procedure for evaluating the genome editing efficiency of the Cr-Nanocomplex of the present invention.

In addition, in order to further assess genome editing patterns, bacteria were treated with the Cr-Nanocomplex or a control, and the number of CFUs was counted in the presence or absence of oxacillin (FIG. 30).

As shown in FIG. 30, the treatment with the Cr-Nanocomplex of the present invention showed a significant decrease in growth under the presence of oxacillin ($65\times10^6$ CFU/ml) compared with the controls ($335\times10^6$ CFU/ml for SpCas9 only; 401×10⁶ CFU/ml for SpCas9-bPEI only), while the treatment with native SpCas9/sgRNA complex showed a smaller decrease in growth (121×10⁶ CFU/ml). In addition, the treatment with SpCas9-bPEI only, without sgRNA, did not show any significant decrease in bacterial growth, demonstrating that reduced bacterial growth when treated with the Cr-Nanocomplex did not result from toxicity by the presence of bPEI. Surprisingly, the lipofectamine formulation of native SpCas9/sgRNA complex showed no significant decrease in bacterial growth (361×10⁶ CFU/ml) compared with the treatment with SpCas9 only as the control. The use of lipofectamine for delivery of SpCas9/sgRNA complex showed substantial delivery efficiency in mammalian cells, but showed poor delivery in the case of bacterial cells. In addition, the fact that the culture of bacteria in the presence of bioactive molecules (e.g., proteins such as Cas9) can influence bacterial growth by acting as a food source or stimulant was considered.

Figure 31:
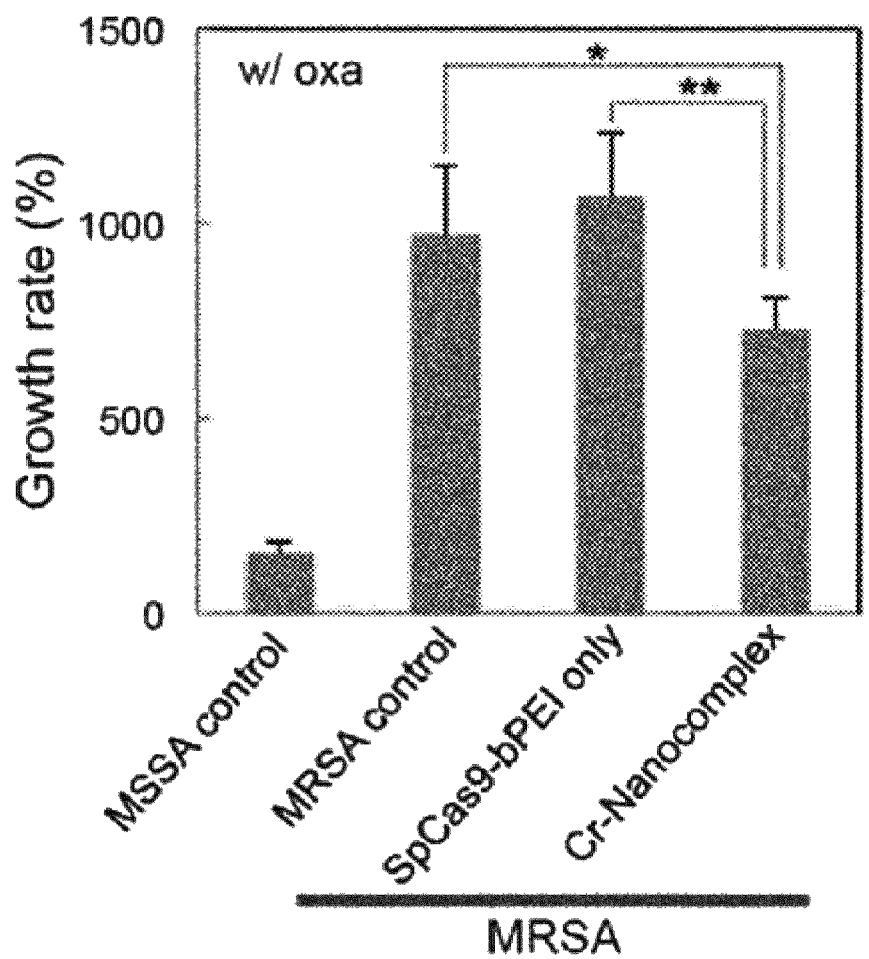
FIG. 31 shows growth rates from the measurement of $OD_{600}$ values after suspension culture of the bacteria treated with the Cr-Nanocomplex of the present invention.

Therefore, the "relative growth" was calculated from (1) number of CFUs when treated with the complex including sgRNA, and normalized with (2) number of CFUs when treated with the complex excluding sgRNA (FIG. 31). As shown in FIG. 31, the treatment with the Cr-Nanocomplex of the present invention showed a relative growth of 16.3% compared with the treatment with SpCas9-bPEI only, while the treatment with SpCas9/sgRNA complex resulted in a relative growth of 35.9% compared with the treatment with SpCas9 only. The treatment with the native SpCas9/sgRNA complex in presence of lipofectamine resulted in a relative growth of 71.6%, compared with SpCas9 with lipofectamine without sgRNA (FIG. 31). These results demonstrate that, compared with the use of native SpCas9 complex regardless of the use of the conventional lipofectamine carrier, the Cr-Nanocomplex of the present invention allows sufficient delivery of the SpCas9 protein and sgRNA into bacteria, thereby enabling the double-strand cleavage of the target DNA at a much higher efficiency.

Figure 32A:
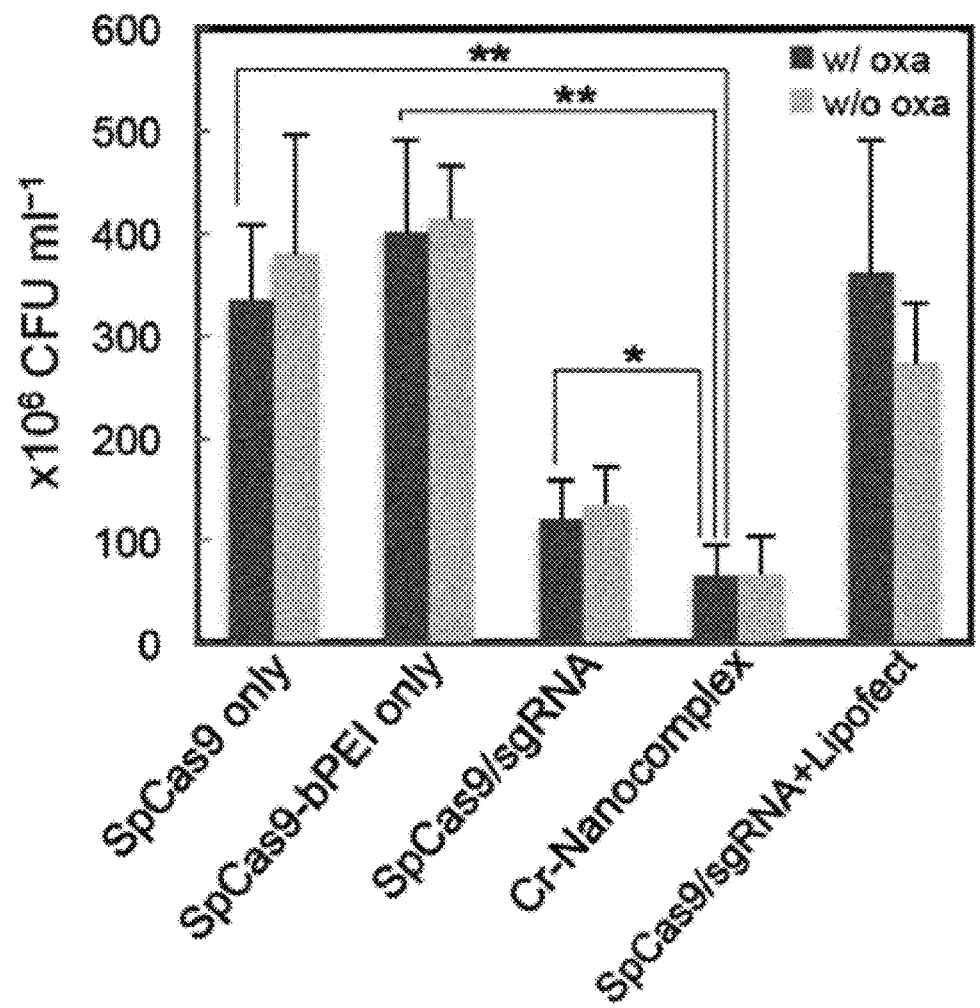
FIGS. 32a and 32b show the results obtained by counting the number of CFUs in the presence or absence of oxacillin after bacteria were treated with the Cr-Nanocomplex or controls, in order to further assess the patterns of genome editing.
Figure 32B:
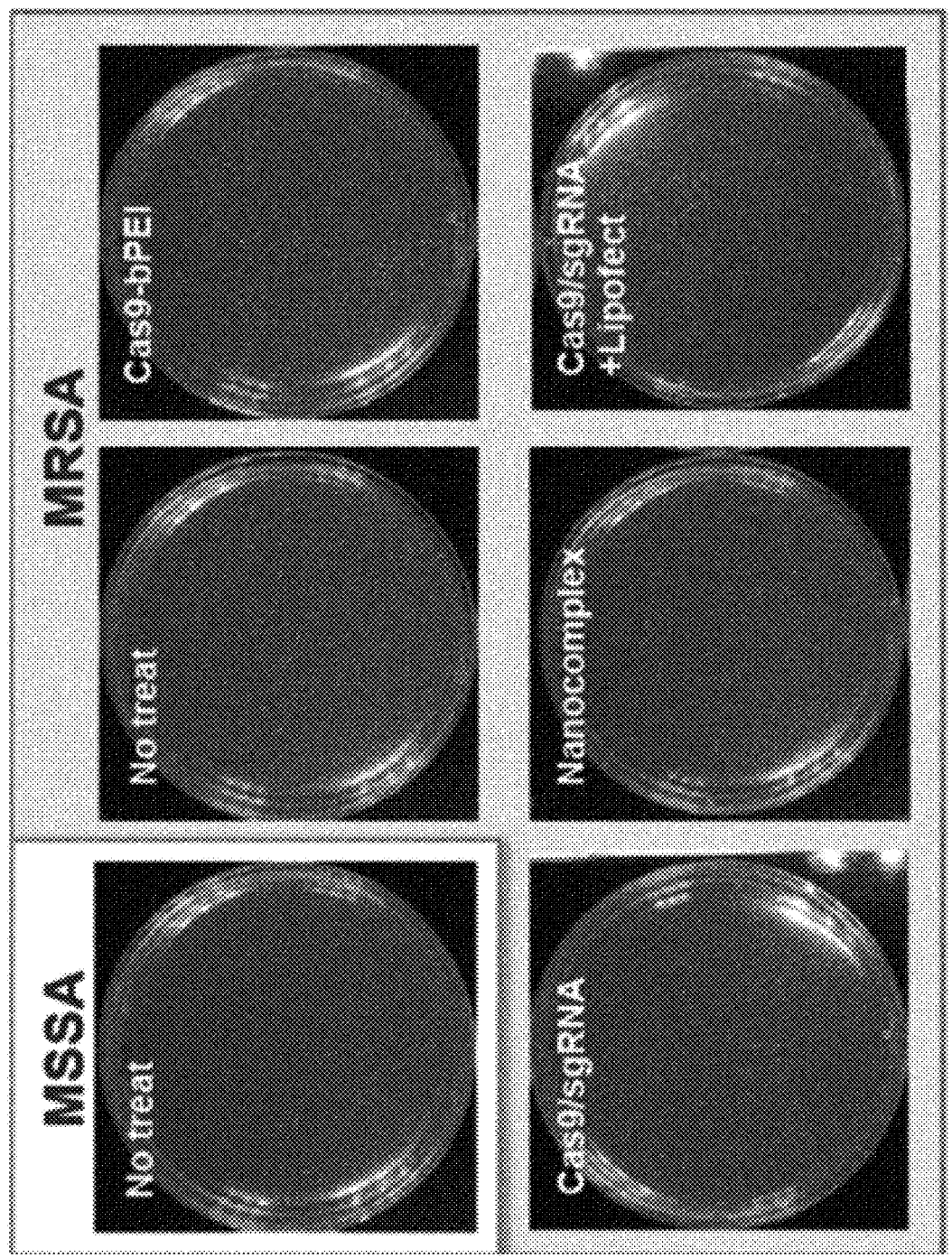

In addition, the dose-dependent genome editing efficiency was determined by treating the bacteria with the Cr-Nanocomplex of various concentrations (FIGS. 32a and 32b). As shown in FIG. 32, when comparing the Cr-Nanocomplex with the native complex, the treatment at a lower concentration resulted in 18.7% inhibition in the relative growth, while the treatment at a higher concentration resulted in 57.7% inhibition in the relative growth. Although the treatment at a higher concentration resulted in a slightly higher mean value in inhibition compared to the treatment at an intermediate concentration, the values were shown to be statistically significant only for the case of intermediate treatment. The treatment with a lower concentration of Cr-Nanocomplex would not be sufficient to exert significant genome editing efficacy, while the treatment with a higher concentration of Cr-Nanocomplex may interfere with the process of genome editing by affecting bacterial function and uptake, or stimulating bacterial growth.

Another critical finding was that the examination of bacterial growth in the absence of oxacillin showed similar results from the values in the presence of oxacillin, with 67×10⁶ CFU/ml for the Cr-Nanocomplex, 135×10⁶ CFU/ml for the native complex, and 414××10⁶ CFU/ml for SpCas9-bPEI only (FIG. 30).

Figure 33:
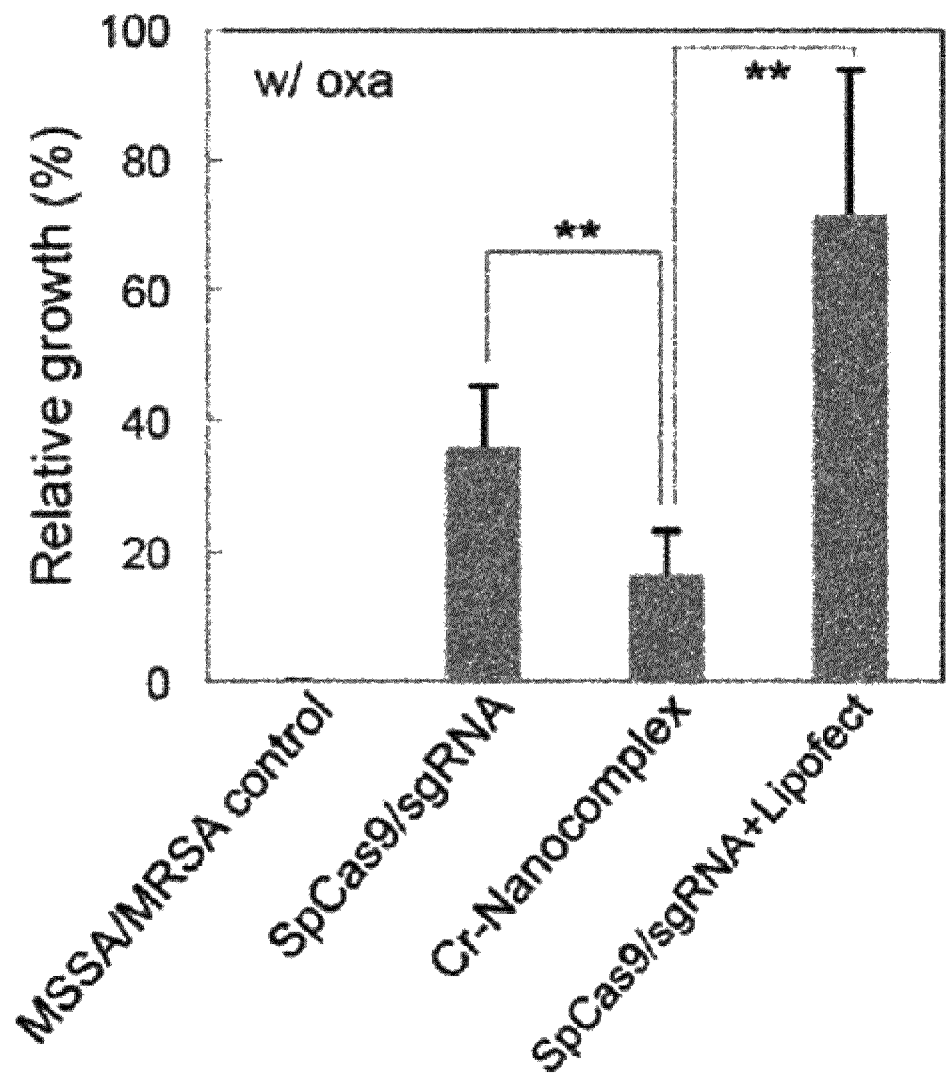
FIG. 33 shows the relative growth (%) of the bacteria treated with the Cr-Nanocomplex of the present invention.
Figure 34:
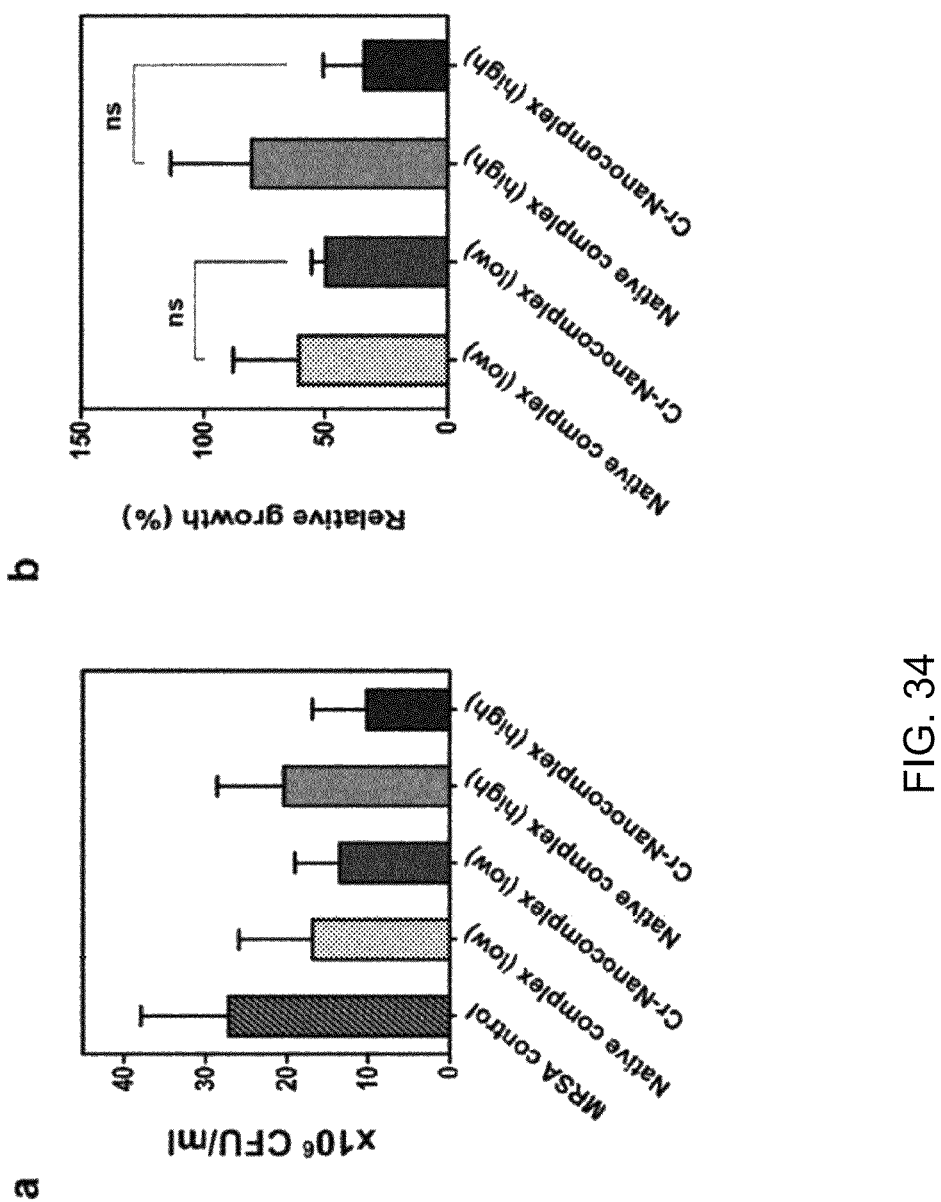
FIG. 34 shows the genome editing efficiency of the Cr-Nanocomplex with different concentrations of the present invention.
Figure 35:
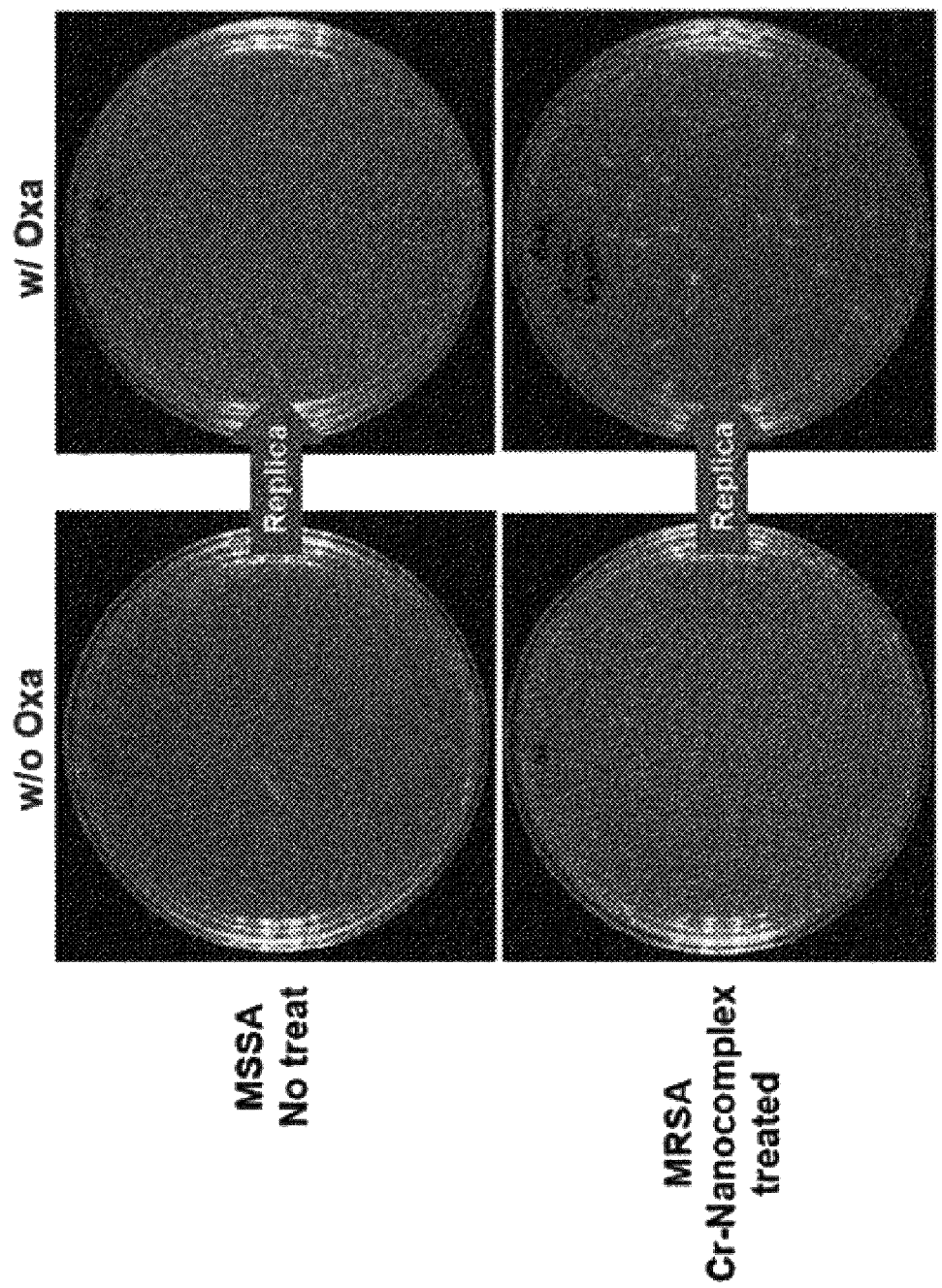
FIG. 35 shows the replica culture experiment results of the bacteria treated with the Cr-Nanocomplex of the present invention.

Replica plating of the bacterial colonies formed from Cr-Nanocomplex-treated bacteria was also performed. Here, primary plates not including oxacillin were replicated on secondary plates including oxacillin, and cultured at 30° C. for 12 h, and then the bacterial colonies were counted. Results showed that all clones which formed colonies in non-selective media also were able to grow in selective media (FIG. 33). These results show that genome editing by the Cr-Nanocomplex resulted in lethality of the bacteria, while the bacteria that tolerated the treatment continued to grow.

Statistical Analysis

All statistical data were calculated and shown as mean±standard deviation. Statistical significance was determined by obtaining the p value using the Student's t test.

SEQUENCE LISTING

This application contains references to amino acid sequences and/or nucleic acid sequences which have been submitted concurrently herewith as the sequence listing text file entitled "000141-US—NP_amended_sequence_listing.TXT", file size 12 KiloBytes (KB), created on 28 Feb. 2022. The aforementioned sequence listing is hereby incorporated by reference in its entirety pursuant to 37 C.F.R. § 1.52(e)(5).

What is claimed is:

1. A polymer carrier material-conjugated clustered regularly interspaced short palindromic repeats (CRISPR)-associated protein 9 (Cas9), wherein the polymer carrier material is a branched polyethyleneimine (PEI), and wherein the branched PEI is conjugated to the Cas9 by a direct covalent bond.

2. A method for preparing a polymer carrier material-conjugated clustered regularly interspaced short palindromic repeats (CRISPR)-associated protein 9 (Cas9), the method comprising:
 (a) reacting a functional group of a polymer carrier material with a bifunctional crosslinker to prepare an activated polymer carrier material; and
 (b) reacting a functional group of a Cas9 with the activated polymer carrier material to prepare a conjugated Cas9, wherein the polymer carrier material is a branched polyethyleneimine (PEI), and wherein the branched PEI is conjugated to the Cas9 by a direct covalent bond.

3. The method of claim 2, wherein the crosslinker in step (a) is selected from the group consisting of succinimidyl 4-(N-maleimidomethyl)cyclohexane-1-carboxylate (SMCC), sulfosuccinimidyl 4-(N-maleimidomethyl)cyclohexane-1-carboxylate (sulfo-SMCC), N-α-maleimidoacetoxysuccinimide ester (AMAS), N-β-maleimidopropyl-oxysuccinimide ester (BMPS), N-γ-maleimidobutyryl-oxysuccinimide ester (GMBS), m-maleimidobenzoyl-N-hydroxysuccinimide ester (MBS), N-ε-malemidocaproyl-oxysuccinimide ester (EMCS), PEGylated SMCC (SM (PEG)), succinimidyl 3-(2-pyridyldithio)propionate (SPDP), PEGylated SPDP (PEG-SPDP), disuccinimidyl glutarate (DSG), dicyclohexylcarbodiimide (DCC), disuccinimidyl suberate (DSS), bissulfosuccinimidyl suberate (BS3), dithiobis(succinimidyl propionate) (DSP), ethylene glycol bis(succinimidyl succinate) (EGS), dimethyl pimelimidate (DMP), bismaleimidoethane (BMOE), 1,4-bismaleimidobutane (BMB), dithiobismaleimidoethane (DTME), 1-ethyl-3-(3-dimethylaminopropyl)carbodiimide hydrochloride (EDC), N-Hydroxysuccinimide (NHS), propargyl-succinimidyl-ester, dibenzocyclooctyne-maleimide (DBCO-maleimide), dibenzocyclooctyne-PEG4-maleimide (DBCO-PEG-maleimide), dibenzocyclooctyne-S—S—N-hydroxysuccinimidyl ester (DBCO—S—S—NHS ester), dibenzocyclooctyne-N-hydroxysuccinimidyl ester (DBCO-NHS ester), acetylene-PEG-NHS ester, and alkyne-PEG-maleimide.

4. The method of claim 2, wherein the activation reaction of the polymer carrier material in step (a) is conducted in a solvent selected from the group consisting of dimethylsulfoxide (DMSO), dimethylformamide (DMF), ethanol, methanol, water, methylene chloride, and chloroform.

5. The method of claim 2, wherein the activation reaction of the polymer carrier material in step (a) is conducted at 4-60° C. for 0.5-24 h.

6. The method of claim 2, wherein the molar ratio of the polymer carrier material and the Cas9 in step (b) is $10^{-1}:1$ to $10^5:1$.

7. The method of claim 2, wherein the conjugation reaction of the functional group of the Cas9 and the activated polymer carrier material in step (b) is conducted at 4-60° C. for 1-48 h.

8. The method of claim 2, wherein the conjugation reaction of the functional group of the Cas9 and the activated polymer carrier material in step (b) is conducted in a water-soluble solvent with pH 4-10.

9. A CRISPR nanocomplex comprising the polymer carrier material-conjugated clustered regularly interspaced short palindromic repeats (CRISPR)-associated protein 9 (Cas9) of claim 1 and single guide RNA (sgRNA).

10. The CRISPR nanocomplex of claim 9, wherein the CRISPR nanocomplex has a particle size of 1-10,000 nm in an aqueous solution dispersion state.

11. The CRISPR nanocomplex of claim 9, wherein the CRISPR nanocomplex has a zeta potential of −100 to +100 mV.

12. A method for preparing the CRISPR nanocomplex of claim 9, the method comprising mixing the polymer carrier material-conjugated clustered regularly interspaced short palindromic repeats (CRISPR)-associated protein 9 (Cas9) and single guide RNA (sgRNA).

13. The method of claim 12, wherein the molar ratio of the polymer carrier material-conjugated Cas9 and the sgRNA is $1:10^{-6}$ to $1:10^6$.

14. A genome editing composition comprising a polymer carrier material-conjugated clustered regularly interspersed short palindromic repeats (CRISPR)-associated protein 9 (Cas9), wherein the polymer carrier material is a branched polyethyleneimine (PEI), wherein the branched PEI is conjugated to the Cas9 by a direct covalent bond, and an excipient.

15. The composition of claim 14, wherein the composition delivers the polymer carrier material-conjugated Cas9 into cells to induce genome editing.

16. The composition of claim 15, wherein the cells are eukaryotic cells or prokaryotic cells.

* * * * *